United States Patent
Briscoe et al.

(10) Patent No.: US 12,397,037 B2
(45) Date of Patent: Aug. 26, 2025

(54) METHODS AND COMPOSITIONS FOR IMMUNOMODULATION

(71) Applicant: CHILDREN'S MEDICAL CENTER CORPORATION, Boston, MA (US)

(72) Inventors: David M. Briscoe, Sharon, MA (US); Michael Klagsbrun, Newton, MA (US); Sarah Bruneau, Boston, MA (US); Nora Kochupurakkal, Boston, MA (US); Hironao Nakayama, Boston, MA (US)

(73) Assignee: CHILDREN'S MEDICAL CENTER CORPORATION

( * ) Notice: Subject to any disclaimer, the term of this patent is extended or adjusted under 35 U.S.C. 154(b) by 86 days.

(21) Appl. No.: 18/296,510

(22) Filed: Apr. 6, 2023

(65) Prior Publication Data

US 2023/0256053 A1  Aug. 17, 2023

Related U.S. Application Data

(62) Division of application No. 16/561,177, filed on Sep. 5, 2019, now abandoned, which is a division of application No. 15/314,970, filed as application No. PCT/US2015/033510 on Jun. 1, 2015, now Pat. No. 10,456,445.

(60) Provisional application No. 62/006,441, filed on Jun. 2, 2014.

(51) Int. Cl.
| | |
|---|---|
| *C07K 14/475* | (2006.01) |
| *A61K 38/17* | (2006.01) |
| *A61K 38/18* | (2006.01) |
| *A61K 38/48* | (2006.01) |
| *A61K 45/06* | (2006.01) |
| *A61P 29/00* | (2006.01) |
| *A61P 37/00* | (2006.01) |
| *C07K 16/18* | (2006.01) |
| *C07K 16/28* | (2006.01) |
| *A61K 39/00* | (2006.01) |

(52) U.S. Cl.
CPC ........ *A61K 38/1709* (2013.01); *A61K 38/177* (2013.01); *A61K 38/18* (2013.01); *A61K 38/482* (2013.01); *A61K 45/06* (2013.01); *A61P 29/00* (2018.01); *A61P 37/00* (2018.01); *C07K 14/475* (2013.01); *C07K 16/18* (2013.01); *C07K 16/28* (2013.01); *C07K 16/2803* (2013.01); *C12Y 304/21* (2013.01); *C12Y 304/21075* (2013.01); *A61K 2039/505* (2013.01); *C07K 2317/76* (2013.01)

(58) Field of Classification Search
CPC ... A61K 38/1761; A61K 38/18; C07K 14/475
See application file for complete search history.

(56) References Cited

U.S. PATENT DOCUMENTS

| | | |
|---|---|---|
| 7,407,766 B1 | 8/2008 | Fujisawa et al. |
| 9,896,490 B2 | 2/2018 | Neufeld et al. |
| 2007/0054852 A1 | 3/2007 | Lin et al. |
| 2010/0150919 A1 | 6/2010 | Appleton et al. |
| 2010/0172921 A1 | 7/2010 | Wu et al. |
| 2010/0247516 A1 | 9/2010 | Neufeld et al. |
| 2011/0064739 A1 | 3/2011 | Borlak et al. |
| 2013/0287726 A1 | 10/2013 | Neufeld et al. |
| 2014/0066360 A1 | 3/2014 | Gounni |
| 2016/0311873 A1 | 10/2016 | Neufeld et al. |
| 2017/0173111 A1 | 6/2017 | Toleando et al. |
| 2024/0092845 A1 | 3/2024 | Briscoe et al. |

FOREIGN PATENT DOCUMENTS

| | | |
|---|---|---|
| WO | 2005030240 A2 | 4/2005 |
| WO | 2005090573 A2 | 9/2005 |
| WO | 2007020075 A1 | 2/2007 |
| WO | WO-2014199364 A1 * | 12/2014 |

OTHER PUBLICATIONS

"Alzheimer's disease", ninds.nih.gov/disorders/alzheimersdisease/alzheimersdisease.htm; Jan. 4, 2012; 3 total pages.*
Bhattacharya et al. Impact of genetic variation on three dimensional structure and function of proteins. PLoS ONE 12(3): e0171355, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
"Cystic fibrosis", www.nhlbi.nih.gov/health/health-topics/cf/; accessed Feb. 3, 2017.*
Doerks et al. Protein annotation: detective work for function prediction. Trends in Genetics 14:248-250, 1998.*
Elgert, K. Immunology, understanding the immune system. New York: Wiley-Liss, Inc., 1996; pp. 323-326.*
Fenton et al. Rheostat positions: a new classification of protein positions relevant to pharmacogenomics. Medicinal Chem Res 29: 1133-1146, 2020.*
Guo et al. Protein tolerance to random amino acid change. Proc Natl Acad Sci USA 101(25): 9205-9210, 2004.*

(Continued)

*Primary Examiner* — Bridget E Bunner
(74) *Attorney, Agent, or Firm* — NIXON PEABODY LLP; David S. Resnick; Nicole D. Kling

(57) ABSTRACT

The methods and uses described herein relate to the modulation of the immune system by modulation of Sema3F levels and/or activity, e.g. suppressing allograft rejection or inflammation by administering a Sema3F agonist or increasing an immune response by administering a Sema3F inhibitor.

13 Claims, 43 Drawing Sheets

Specification includes a Sequence Listing.

(56) References Cited

OTHER PUBLICATIONS

"Human Immunodeficiency Virus (HIV)", www.ncbi.nlm.nih.gov/pubmedhealth/PMHT0025049/; accessed Feb. 3, 2017.*
Kotan et al. Loss-of-function variants in SEMA3F and PLXNA3 encoding semaphorin-3F and its receptor plexin-A3 respectively cause idiopathic hypogonadotropic hypogonadism. Genetics Med 23: 1008-1016, 2021.*
Kunath et al. Blockade of the neuropilin-2/plexin A2 receptor—A new therapeutic approach towards rheumatoid arthritis? Brain, Behavior, and Immunity 29: S5, 2013.*
Neufeld et al. The semaphorins: versatile regulators of tumour progression and tumour angiogenesis. Nature Rev 8: 632-645, 2008.*
Ngo et al. "Computational complexity, protein structure prediction, and the Levinthal paradox" in The Protein Folding Problem and Tertiary Structure Prediction, pp. 492-495, 1994.*
Skolnick et al. From genes to protein structure and function: novel applications of computational approaches in the genomic era. Trends Biotechnol 18(I):34-39 2000.*
Smith et al. The challenges of genome sequence annotation or "the devil is in the details". Nature Biotechnol 15: 1222-1223, 1997.*
Tokuriki et al. Stability effects of mutations and protein evolvability. Curr Opin Structural Biol 19: 596-604, 2009.*
Wells, J.A. Additivity of mutational effects in proteins. Biochemistry 29(37): 8509-8517, 1990.*
Nakayama et al. Novel effects of semaphorin 3F on the regulation of intracellular PI3K-Akt signaling. Transplant 98(Suppl 1): 318, abstract #B1157; July 2014.*
Adams et al., "The chemorepulsive activity of secreted semaphorins is regulated by furin-dependent proteolytic processing." The EMBO journal 16.20 (1997): 6077-6086.
Appleton et al. "Structural studies of neuropilin/antibody complexes provide insights into semaphorin and VEGF binding." The EMBO Journal 26: 4902-4912 (2007).
Bielenberg et al. Semaphorin 3F, a chemorepulsant for endothelial cells, induces a poorly vascularized, encapsulated, nonmetastatic tumor phenotype. J Clin Invest. Nov. 2004;114(9):1260-71.
Borriello et al. "Structure-based discovery of a small non-peptidic Neuropilins antagonist exerting in vitro and in vivo anti-tumor activity on breast cancer model." Cancer letters 349.2 (2014): 120-127.
Casazza et al. "Tumour growth inhibition and anti-metastatic activity of a mutated furin-resistant Semaphorin 3E isoform." EMBO molecular medicine 4(3): 234-250 (2012).
Chabbert-De Ponnat et al., "Antiproliferative effect of semaphorin 3F on human melanoma cell lines." The Journal of Investigative Dermatology 126(10):2343-2345 (2006).
Caunt et al. "Blocking neuropilin-2 function inhibits tumor cell metastasis." Cancer cell 13.4 (2008): 331-342.
Data Sheet. Recombinant Human Semaphorin 3F Fc Chimera Catalog No. 9878-S3. R&D Systems a bio-techne brand. URL: https://resources.mdsystems.com/pdfs/datasheets/9878-s3.pdf pp. 1-2 (2018).
Delgoffe et al., Stability and function of regulatory T cells is maintained by a neuropilin-1-semaphorin-4a axis. Nature. Sep. 12, 2013;501(7466):252-6.
Geretti et al. "A mutated soluble neuropilin-2 B domain antagonizes vascular endothelial growth factor bioactivity and inhibits tumor progression." Molecular Cancer Research 8.8 (2010): 1063-1073.
Gray et al. "Therapeutic targeting of neuropilin-2 on colorectal carcinoma cells implanted in the murine liver." Journal of the National Cancer Institute 100.2 (2008): 109-120.
Guo et al. "Mechanistic basis for the potent anti-angiogenic activity of semaphorin 3F." Biochemistry 52(43):7551-7558 (2013).
Hansen et al., Neuropilin 1 deficiency on CD4+Foxp3+ regulatory T cells impairs mouse melanoma growth. J Exp Med. Oct. 22, 2012;209(11):2001-16.
HIDA "Neuropilins as Common Targeting Molecules on Tumor and Endothelial Cells to Inhibit Metastasis." Biotherapy 22(2):80-86 (2008) [Partial English Translation Included].
Janssen et al. "Neuropilins lock secreted semaphorins onto plexins in a ternary signaling complex." Nature structural & molecular biology 19.12 (2012): 1293-1299.
Kawakaki et al. "Control of intracellular localization and function of Cx43 by SEMA3F." Journal of Membrane Biology 217.1 (2007): 53-61.
Kochupurakkal et al. "A Novel Immunomodulatory Function for Semaphorin3F and Neuropilin-2 in Allograft Rejection.: Abstract# 1491." Transplantation 98 (2014): 33.
Kessler et al., "Semaphorin-3F is an inhibitor of tumor angiogenesis." Cancer Research 64(3):1008-1015 (2004).
Klagsbrun et al. "A role for axon guidance receptors and ligands in blood vessel development and tumor angiogenesis." Cytokine & growth factor reviews 16(4-5): 535-548 (2005).
Kumanogoh et al., "Immunological functions of the neuropilins and plexins as receptors for semaphorins." Nature Reviews Immunology 13(11):802-814 (2013).
Lepelletier et al., "Immunosuppressive role of semaphorin-3A on T cell proliferation is mediated by inhibition of actin cytoskeleton reorganization." European Journal of Immunology 36(7):1782-1793 (2006).
Mendes-Da-Cruz et al., "Semaphorin 3F and neuropilin-2 control the migration of human T-cell precursors." PLoS One 9(7):e103405 (2014).
Nakayama et al., "Regulation of mTOR signaling by semaphorin 3F-neuropilin 2 interactions in vitro and in vivo." Scientific Reports 5(1):11789 (2015).
Parker et al., "Effect of C-terminal sequence on competitive semaphorin binding to neuropilin-1." Journal of molecular biology 425.22 (2013): 4405-4414.
Parker et al., "Furin processing of semaphorin 3F determines its anti-angiogenic activity by regulating direct binding and competition for neuropilin." Biochemistry 49(19):4068-4075 (2010).
Sakurai et al., "Semaphorin signaling in angiogenesis, lymphangiogenesis and cancer." Cell Research 22(1):23-32 (2012).
Shimizu et al., "ABL2/ARG tyrosine kinase mediates SEMA3F-induced RhoA inactivation and cytoskeleton collapse in human glioma cells.", Journal of Biological Chemistry 283(40): 27230-27238 (2008).
Tang et al. "Blocking neuropilin-2 enhances corneal allograft survival by selectively inhibiting lymphangiogenesis on vascularized beds." Molecular vision 16 (2010): 2354.
Varshavsky et al., "Semaphorin-3B is an angiogenesis inhibitor that is inactivated by furin-like pro-protein convertases." Cancer research 68.17 (2008): 6922-6931.
Weiss et al., Neuropilin 1 is expressed on thymus-derived natural regulatory T cells, but not mucosa-generated induced Foxp3+ T reg cells.J Exp Med. Sep. 24, 2012;209(10):1723-42, S1. Epub Sep. 10, 2012.
Chen et al. "Cross-Species Array Comparative Genomic Hybridization Identifies Novel Oncogenic Events in Zebrafish and Human Embryonal Rhabdomyosarcoma" PLoS Genetics 9(8): e1003727 (2013).
Ji et al. "Expression and Function of Semaphorin 3A and Its Receptors in Human Monocyte-derived Macrophages" Hum Immunol 70(4):211-217 (2009).

* cited by examiner

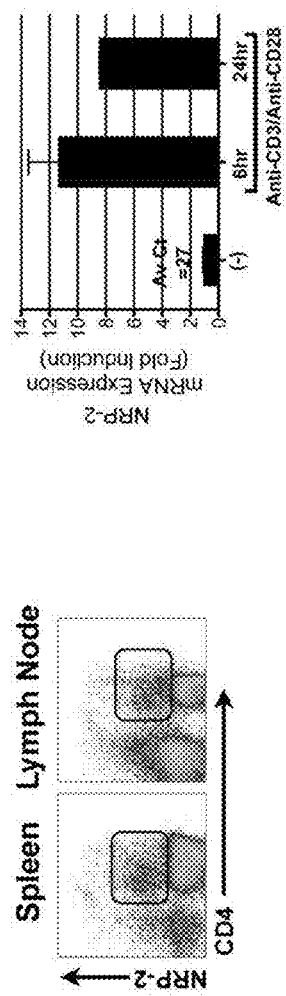
FIG. 27A
FIG. 27B
FIG. 27D
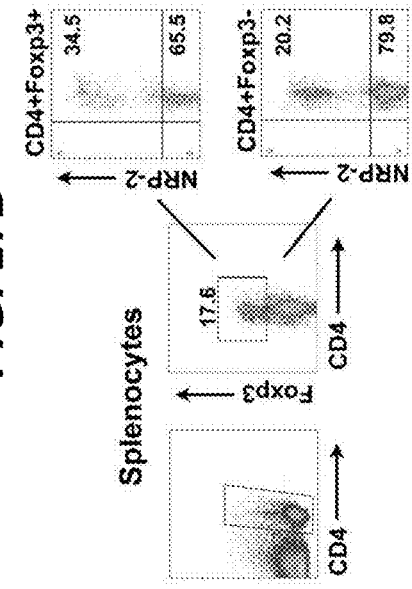
FIG. 27E
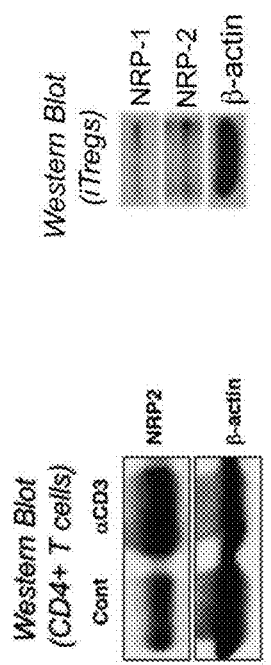
FIG. 27F
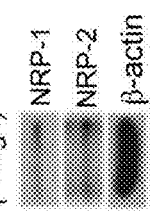

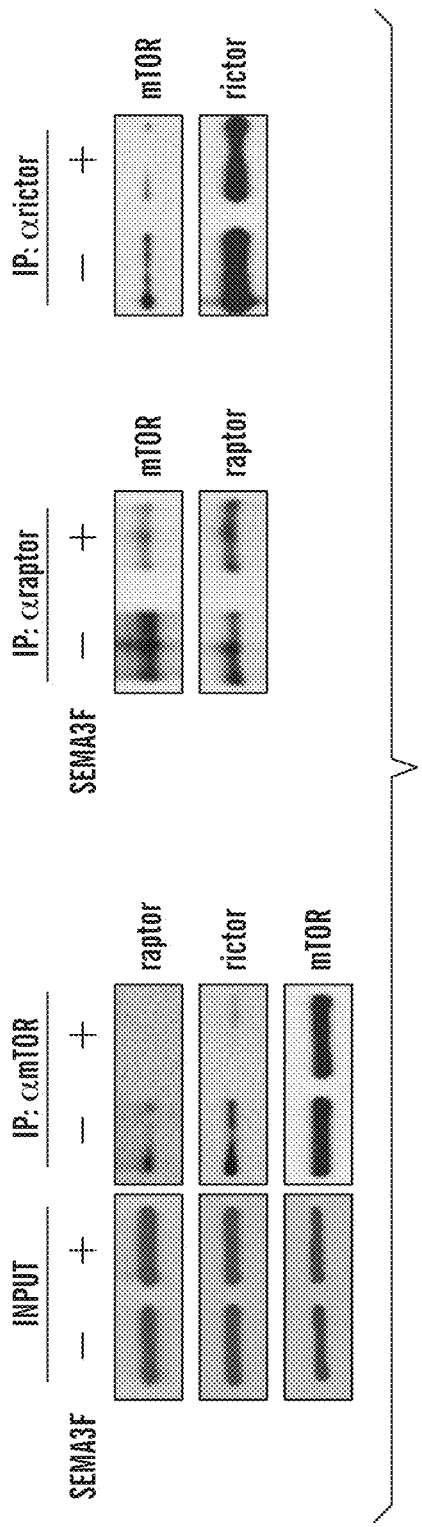
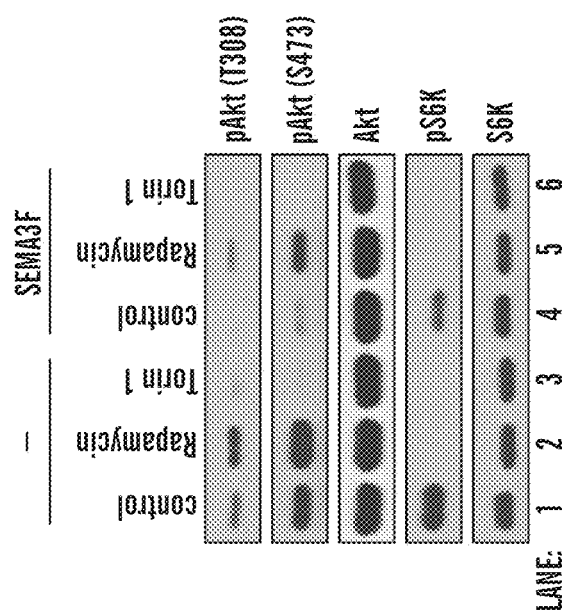
FIG. 29A
FIG. 29B

A

B

C

D

A  B

Day 5 Post Transplantation, n=6 mice

SEQUENCE LISTING

```
Sequence total quantity: 7
SEQ ID NO: 1            moltype = AA   length = 785
FEATURE                 Location/Qualifiers
source                  1..785
                        mol_type = protein
                        organism = Homo sapiens
SEQUENCE: 1
MLVAGLLLWA SLLTGAWPSF PTQDHLPATP RVRLSFKELK ATGTAHFFNF LLNTTDYRIL   60
LKDEDHDRMY VGSKDYVLSL DLHDINREPL IIHWAASPQR IEECVLSGKD VNGECGNFVR  120
LIQPWNRTHL YVCGTGAYNP MCTYVNRGRR AQATPWTQTQ AVRGRGSRAT DGALRPMPTA  180
PRQDYIFYLE PERLESGKGK CPYDPKLDTA SALINEELYA GVYIDFMGTD AAIFRTLGKQ  240
TAMRTDQYNS RWLNDPSFIH AELIPDSAER NDDKLYFFFR ERSAEAPQSP AVYARIGRIC  300
LNDDGGHCCL VNKWSTFLKA RLVCSVPGED GIETHFDELQ DVFVQQTQDV RNPVIYAVFT  360
SSGSVFRGSA VCVYSMADIR MVFNGPFAHK EGPNYQWMPF SGKMPYPRPG TCPGGTFTPS  420
MKSTKDYPDE VINFMRSHPL MYQAVYPLQR RPLVVRTGAP YRLTTIAVDQ VDAADGRYEV  480
LFLGTDRGTV QKVIVLPKDD QELEELMLEE VEVFKDPAPV KTMTISSKRQ QLYVASAVGV  540
THLSLHRCQA YGAACADCCL ARDPYCAWDG QACSRYTASS KRRSRRQDVR HGNPIRQCRG  600
FNSNANKNAV ESVQYGVAGS AAFLECQPRS PQATVKWLFQ RDPGDRRREI RAEDRFLRTE  660
QGLLLRALQL SDRGLYSCTA TENNFKHVVT RVQLHVLGRD AVHAALFPPL SMSAPPPPGA  720
GPPTPPYQEL AQLLAQPEVG LIHQYCQGYW RHVPPSPREA PGAPRSPEPQ DQKKPRNRRH  780
HPPDT                                                              785

SEQ ID NO: 2            moltype = DNA   length = 3531
FEATURE                 Location/Qualifiers
source                  1..3531
                        mol_type = unassigned DNA
                        organism = Homo sapiens
SEQUENCE: 2
ccgcggcgcc gatcccggct gaggcgcagc ggcgagaggt cgcgggcagg gccatggccc    60
cggggggccg ctagcgcgga ccggcccaac gggagccgct ccgtgccgcc gccgccgccc   120
gggcgcccag gccccgccgc tgcggaagag gtttctagag agtggagcct gcttcctggg   180
ccctaggccc ctcccacaat gcttgtcgcc ggtcttcttc tctgggcttc cctactgacc   240
ggggcctggc catccttccc cacccaggac cacctcccgg ccacgcccg gtccggctc    300
tcattcaaag agctgaaggc cacaggcacc gcccacttct tcaacttcct gctcaacaca   360
accgactacc gaatcttgct caaggacgag gaccacgacc gcatgtacgt gggcagcaag   420
gactacgtgc tgtccctgga cctgcacgac atcaaccgcg agcccctcat tatacactgg   480
gcagcctccc cacagcgcat cgaggaatgc gtgctctcag gcaaggatgt caacggcgag   540
tgtgggaact cgtcaggct catccagccc tggaaccgaa cacacctgta tgtgtgcggg    600
acaggtgcct acaaccccat gtgcacctat gtgaaccgcg gacgccgcgc ccaggccaca   660
ccatggaccc agactcaggc ggtcagaggc cgcggcagca gagccacgga tggtgccctc   720
cgcccgatgc ccacagcccc acgccaggat tacatcttct acctggagcc tgagcgactc   780
gagtcaggga agggcaagtg tccgtacgat cccaagctgg acacagcatc ggccctcatc   840
aatgaggagc tctatgctgg tgtgtacatc gatttttatg gcactgatgc agccatcttc   900
cgcacacttg gaaagcagac agccatgcgc acggatcagt acaactcccg gtggctgaac   960
gacccgtcgt tcatccatgc tgagctcatt cctgacagtg cggagcgcaa tgatgataag  1020
ctttacttct tcttccgtga gcggtcggca gaggcgccgc agagcccgc ggtgtacgcc   1080
cgcatcgggc gcatttgcct gaacgatgac ggtggtcact gttgcctggt caacaagtgg  1140
agcacattcc tgaaggcgcg gctcgtctgc tctgtccgtg gcgaggatgg cattgagact  1200
cactttgatg agctccagga cgtgtttgtc cagcagaccc aggacgtgag gaaccctgtc  1260
atttacgctg tctttacctc ctctggctcc gtgttccgag gctctgccgt gtgtgtctac  1320
tccatgctg atattcgcat ggtcttcaac gggccctttg cccacaaaga ggggcccaac  1380
taccagtgga tgccccttctc agggaagatg ccctacccac ggcgggcac gtgccctggt  1440
ggaaccttca cgccatctat gaagtccacc aaggattatc ctgatgaggt gatcaacttc  1500
atgcgcagcc acccactcat gtaccaggcc gtgtaccctc tgcagcggcg gcccctggta  1560
gtccgcacag tgctcccta ccgccttacc actattgccg tggaccaggt ggatgcagcc   1620
gacgggcgct atgaggtgct ttttcctggc acagaccgcg ggacagtgca aaggtcatt   1680
gtgctgccca aggatgacca ggagttggag gagctcatgc tggaggagt gaggttcttc   1740
aaggatccag cacccgtcaa gaccatgacc atctcttcta agaggcaaca actctacgtg  1800
gcgtcagccg tgggtgtcac acacctgagc ctgaccgct gccaggcgta tggggctgcc  1860
tgtgctgact gctgccttgc ccgggaccct tactgtgcct gggatggcca ggcctgctcc  1920
cgctatacag catcctccaa gaggcggagc cgccggcagg atcgccgca cggaaaccct  1980
atcaggcagt gccgtgggtt caactccaat gccaacaaga atgccgtgga gtctgtgcag  2040
tatggcgtgg ccggcagcgc agccttcctt gagtgccagc ccgctcgcc ccaagccact   2100
gttaagtggc tgttccagcg agatcctggt gaccggcgcc gagagattcg tgcagaggac  2160
cgcttcctgc gcacagagca gggcttgttg ctccgtgcac tgcagctcag cgatcgtggc  2220
ctctactcct gcacagccac tgagaacaac tttaagcacg tcgtcacacg agtgcagctg  2280
catgtactgg gccgggacgc cgtccatgct gcccttcttcc caccactgtc catgagcgcc  2340
ccgccacccc caggcgcagg ccccccaacg cctccttacc aggagttagc ccagctgctg  2400
gcccagccag aagtgggcct catccaccag tactgccaag gttactggcg ccatgtgccc  2460
cccagcccca ggggaggctcc aggggcaccc cggtctcctg agcccaggga ccagaaaaag  2520
ccccggaacc gccggcacca ccctccggac acatgaggcc agctgctgt gctgccatg   2580
ggccagccta gcccttgtcc ctttaatat aaaagatata tatatatata tatatatata   2640
aaatatctat attctataca cacccctgccc ctgcaaagat aatatttatt ggtgggttga  2700
atatagcctg cctcagtggc agcatcctcc aaaacttaga cccatgctgg tcagagacgg  2760
cagaaaacag agcctgccta accaggccca gccagttggt ggggcaggc caggaccaca   2820
cagtccccag actcagctgg aagtctacct gctggacagc ctcgccaag atctacagga   2880
caaagggagg gagcaagccc tactcggatg gggcacggac tgtccacctt ttctgatgtg  2940
tgttgtcagc ctgtgctgtg gcatagacat ggatgcgagg accactttgg agactggggt  3000
```

```
ggcctcaaga gcacacagag aagggaagaa ggggccatca caggatgcca gcccctgcct  3060
gggttggggg cactcagcca cgaccagccc cttcctgggt atttattctc tatttattgg  3120
ggataggaga agaggcatcc tgcctgggtg ggacagcctc ttcagcccct tctcccctcc  3180
ccgcctggcc agggcagggc caccccactc tacctcctta gctttccctg tgccactttg  3240
actcagaggc tgggagcata gcagaggggc caggcccagc cagagctgac gggaggcccc  3300
agctctgagg ggaggggtc cgtggtagag gcctgggcc ggtagaggct ccccagggct  3360
cccttatgtc caccacttca ggggatgggt gtggatgtaa ttagctctgg ggggcagttg  3420
ggtagatggg tgggggctcc tggtggcctt ctgctgccca ggccacagcc gcctttgggt  3480
tccatcttgc taataaacac tggctctggg actagaaaaa aaaaaaaaaa a          3531
```

```
SEQ ID NO: 3           moltype = DNA   length = 6671
FEATURE                Location/Qualifiers
source                 1..6671
                       mol_type = unassigned DNA
                       organism = Homo sapiens
SEQUENCE: 3
cagagatcgc gagcgaggca ccagcctgca gccggccccc agcacatcct cagccgcaca   60
gacactcggc gaggtggagg tgagggcggg cgccagcgaa ctcggagagg ggctcgctca  120
ctcccaggcg atcccagccg ccaccgccgc cgcaccagca gcagcaacag cagcagcagc  180
ttccttcctc agactcccct cgagaggctg ccaagcgggg tgtagccgtt gggggaggct  240
cccgccgggg gaacccggcg aggacaagag cagggcggcc gccttccact cgggctgtcc  300
ggcggcggct gcctccgccc gtgtgtccgt caagggtgcg gcgggatgtg tgtcagttta  360
cgcctctgag atcacacagc tgcctggggg ccgtgtgatg cccaaggcaa gtcttggttt  420
taattattat tattatcatt attgttacgc ttggctttcg ggaaatactc gtgatatttg  480
taggataaag gaaatgacac tttgaggaac tggagaaac atatatgcgt tttgttttta  540
agaggaaaac cgtgttctct tcccggcttg ttccctcttt gctgatttca ggagctactc  600
tcctcctggt gaggtggaaa ttccagcaag aatagaggtg aagacaagcc accaggactc  660
aggaggggaaa cgctgaccat tagaaacctc tgcataagac gttgtaagga ggaaaataaa  720
agagagaaaa acacaaagat ttaaacaaga aacctacgaa cccagctctg gaagagccaa  780
ccttctccaa aatggatatg tttcctctca cctgggtttt cttagccctc tactttttcaa  840
gacaccaagt gagaggccaa ccagaccac cgtgcggagg tcgtttgaat tccaaagatg  900
ctggctatat cacctctccc ggttacccc aggactaccc ctcccaccag aactgcgagt  960
ggattgttta cgccccgaa cccaaccaga agattgtcct caacttcaac cctcactttg 1020
aaatcgagaa gcacgactgc aagtatgact ttatcgagat tcgggatggg gacagtgaat 1080
ccgcagacct cctgggcaaa cactgtggga acatcgcccc gcccaccatc atctcctcgg 1140
gctccatgct ctacatcaag ttcacctccg actacgcccg gcagggggca ggcttctctc 1200
tgcgctacga gatcttcaag acaggctctg aagattgctc aaaaaacttc acaagcccca 1260
acgggaccat cgaatctcct gggtttcctg agaagtatcc acacaacttg gactgcacct 1320
ttaccatcct ggccaaaccc aagatggaga tcatcctgca gttcctgatc tttgacctgg 1380
agcatgaccc tttgcaggtg ggagagggg actgcaagta cgattggctg gacatctggg 1440
atggcattcc acatgttggc ccctgattg gcaagtactg tgggaccaaa acaccctctg 1500
aacttcgttc atcgacgggg atcctctcc tgacctttca cacggacatg gcggtggcca 1560
aggatgcttt ctctgcgcgt tactacctgg tccaccaaga gccactagag aacttttcagt 1620
gcaatgttcc tctgggcatg gagtctggcc ggattgctaa tgaacagatc agtgcctcat 1680
ctacctactc tgatgggagg tggacccctc aacaaagccg gctccatggt gatgacaatg 1740
gctggacccc caacttggat tccaacaagg agtatctcca ggtggacctg cgcttttaa 1800
ccatgctcac ggccatcgca acacaggag cgatttccag ggaaacacag aatggctact 1860
atgtcaaatc ctacaagctg gaagtcagca ctaatgagga ggactggatg gtgtaccggc 1920
atggcaaaaa ccacaaggta tttcaagcca acaacgatgc aactgaggtg ttctgaaca 1980
agctccacgc tccactgctg acaaggtttg ttagaatccg ccctcagacc tggcactcag 2040
gtatcgccct ccggctggag ctcttcggct gccgggtcac agatgctccc tgctccaaca 2100
tgctggggat gctctcaggc ctcattgcag actcccagat ctccgcctct tccacccagg 2160
aatacctctg gagcccagt gcagcccgcc tggtcagcag ccgctcgggc tggttccctc 2220
gaatccctca ggcccagccc ggtgaggagt ggcttcaggt agatctggga cacccaaga 2280
cagtgaaagg tgtcatcatc cagggagccc gcggaggaga cagtatcact gctgtggaag 2340
ccagagcatt tgtgcgcaag ttcaaagtct cctacagcct aaacggcaag gactgggaat 2400
acattcagga ccccaggacc cagcagccaa agctgttcga agggaacatg cactatgaca 2460
ccctgacat ccgaaggttt gaccccattc cggcacagta tgtgcgggta cccggagac 2520
ggtggtcgcc ggcgggatt gggatgcggc tggaggtgct gggctgtgac tggacagact 2580
ccaagcccac ggtagacg ctgggaccca ctgtgaagag cgaagagaca accaccccct 2640
accccaccga agaggaggcc acagagtgtg gggagaactg cagctttgag gatgacaaag 2700
atttgcagct cccttcggga ttcaattgca acttcgattt cctcgaggag ccctgtggtt 2760
ggatgtatga ccatgccaag tggctccgga ccacctgggc cagcagctcc agcccaaacg 2820
accggacgtt tccagatgac aggaattttct tgcggctgca ggtgacagc cagagagagg 2880
gccagtatgc ccggctcatc agcccccctg tccacctgcc ccgaagcccg gtgtgcatgg 2940
agttccagta ccaggccacg ggcggccgcg gggtggcgct gcaggtggtg cgggaagcca 3000
gccaggagag caagttgctg tgggtcatcc gtgaggacca gggcggcgag tggaagcacg 3060
gcggggatcat cctgccagc tacgcacatgg agtaccagat tgtgttcgag ggagtgatag 3120
ggaaaggacg ttccggagag attgccattg atgacattcg gataagcact gatgtccaca 3180
tggagaactg catggaaccc atctcggctt ttgcaggtga gaatttttaaa gtggacatcc 3240
cagaaataca tgagagagaa ggatatgaag atgaaattga tgatgaatac gaggtggact 3300
ggagcaattc ttcttctgca acctcagggt ctggcgcccc ctcgaccgac aaagaaaaga 3360
gctggctgta caccctggat cccatcctca tcaccatcat cgccatgagc tcactgggcg 3420
tcctcctggg cgccaccctg t gcaggctcc tgtctactcg cacctgttcc ctcgggg 3480
tgagctcccg aagctgcacc acactggaga actacaactt cgagctctac gatggccttg 3540
agcacaaggt caagatgaac caccaaaagt gctgctccga ggcatgacgg attgcacctg 3600
aatcctatct gacgtttcat tccagcaaga ggggctgggg aagattacat tttttttttcc 3660
tttgaaaact gaatgccata atctcgatca aaccgatcca gaataccgaa ggtatggaca 3720
ggacagaaaa gcgagtcgca ggaggaaggg agatgcagcc gcacagggga tgattaccct 3780
```

```
cctaggaccg cggtggctaa gtcattgcag gaacggggct gtgttctctg ctgggacaaa   3840
acaggagctc atctctttgg ggtcacagtt ctattttgtt tgtgagtttg tattattatt   3900
attattatta ttattattat atttttatttc tttggtctgt gagcaactca aagaggcaga   3960
agaggagaat gacttttcca gaatagaagt ggagcagtga tcattattct ccgctttctc   4020
tttctaatca acacttgaaa agcaaagtgt cttttcagcc tttccatctt tacaaataaa   4080
actcaaaaaa gccgtccagc ttatcccatc ctctgattgt cttctgactt aagggattta   4140
ctgtggtgta ggttctgcca gccaacccta caagctgcca tttccagtcc tagcatttaa   4200
gtaggatgtt gttgccttta acttttctta tccaggggaa aattgccatt ttagggtcag   4260
catgaacagc tctttcttgt atgcgattta aaacaaactg gaaaggaaac ttcacacgtc   4320
aaaatccata gaagcgcctg gacgaggctt aaagtgcttt gtgagtgaat aggagccatt   4380
cgctaattct agaccacag tgtcctggtgg tgggcttcc cttgtggggc ttctggtggt   4440
ggttttgcct tttcttttcc ctcctccatg ttccttctaaa acatatacat atatacatac   4500
acacatacac atattcttca ggtctctaag ccccctggaag cagcattgtg tgatattctc   4560
agaggcaggg gaaaatagag ggaaaaatag agactattgg tatgttctcc ccatcagcga   4620
gttattgtaa ctggtcacca ctggacggga aggagaacag aggagaggga aagagaagcc   4680
caacctctgt gatcatatga gggccaaggc tgagcagtgt agacagagac cctttgaaat   4740
gcatttgtct ctcaaataga ctagtaaaca ccgacttctc ctttgggtta caaacaccat   4800
ttcaaccttt cgggagagtc agagctagga tgtacaagaa ctgattctaa ccagaagtcc   4860
gcaagtactg tggacaagaa tgcttaacca tgctgcttca gccttgagag acctaggttc   4920
ttacacatat gcacacacgc atacacacat gcacgcacac acacatacac acatgcacgc   4980
acgcacgcat gcacaccaat ttatgttttt attaagtgcc ttgaaaaaat gaagaaaaat   5040
gtattttccc tttatgtaaa aattagtgaa tatcttatga attaaggcat tcctcttttcc   5100
ctaaccccga tggctccatt cccaagtacc ccaactcact gctgatccta ttaaaggaat   5160
gagtcctgct acccgagtgg tagtcatagc cctagatgac tctcaactac tcttcaaagg   5220
gaggcatcag gaatagaatg aaactgtgtg aaggataaga ttgttcgcat caagatccaa   5280
atcttgattt catattaacg cctaaggatt gcctgtgtgc tggaaatata tttgaaactc   5340
aaccagtatg cccagcctat tgcatatcat tgtcagacca tttttgctgc tgtggtcacc   5400
cacgatttca tttgtcttat acccaggtga aaggggaagg gtgaatggga ctggctggtt   5460
cctttaaatg ttaacttatg gaaatgctag ttcaaatggt aatgtcacag tgttttgtat   5520
gcagagagca agagttcaac caacagctgt ttattcatgt gtgtgtgtct ttgctgcttt   5580
gagttctctg tatctactgt gtatgtgaat ggtcatgtgg gactcagtgg tggtgttgtg   5640
actttgacct aggggtccgag tgtcacagct gatcttggca ctcggcactc attggcacag   5700
tggtagttag aggtgaaaag tagagctgtc aagcccaagg gcttagcttt agggctcctc   5760
ctgagttcgg cccacagtag aagcaagatt ttaactagcc ccttttcctc ttcaccctcc   5820
catgatgcgc agtgttcaga aagctggtaa gtcctaggga tttccagaag tagcctgcag   5880
aagaaggtaa gtttgaaagc cactccaggg gtcctgatgc tgtcatgctc agtgagccat   5940
tttacagttc tccaaagtct agccctgttt cggacctgca cttcacctct aagttatgta   6000
caactcaacc tgcatccctc taaaagtcct atatccatat tcaccattgg ctaatttgag   6060
gccctgactg ggccttgaat gctaaaaaga agcagggtac gcagggctac atgtagatac   6120
cacaccaagg ctggaggctg gtctgtcata agacagaaag aaagacgctg ggcccaattt   6180
tgacttggcc aggggacacc ttggtgtgtt tgttatcttt atctgtgggt aggctagctg   6240
acccatctcc ttgagtcatt cccttttggga aaccccactg ccagtattga tctccttttt   6300
gccttgtact gaatgacaca ttacctccac actctcccgg acaacagggcc   6360
acagggttgc tttctgtctt tggtgggggca ggggagttga cagggatgag ggtccaagga   6420
ataagcatga atgacaagaa aacaaggagaa gagttaacc tgtcacatag caggttaact   6480
ttttcagggt ttgcagttag aggtattcga ccattcactg gctgagccag atcacgggaa   6540
cttgagagct tttactgtga ttcttcaatg taaaaaataa acaacaatgt caaactgtgt   6600
ttatatgatt tgtataaagc cttttttaaga ttactattta aataaacatt ataccagaga   6660
taaaaaaaaa a                                                        6671

SEQ ID NO: 4         moltype = AA   length = 931
FEATURE              Location/Qualifiers
source               1..931
                     mol_type = protein
                     organism = Homo sapiens
SEQUENCE: 4
MDMFPLTWVF LALYFSRHQV RGQPDPPCGG RLNSKDAGYI TSPGYPQDYP SHQNCEWIVY    60
APEPNQKIVL NFNPHFEIEK HDCKYDFIEI RDGDSESADL LGKHCGNIAP PTIISSGSML   120
YIKKSTDYAR QGAGFSLRYE IFKTGSEDCS KNFTSPNGTI ESPGFPEKYP HNLDCTFTIL   180
AKPKMEIILQ FLIFDLEHDP LQVGEGDCKY DWLDIWDGIP HVGPLIGKYC GTKTPSELRS   240
STGILSLTFH TDMAVAKDGF SARYYLVHQE PLENFQCNVP LGMESGRIAN EQISASSTYS   300
DGRWTPQQSR LHGDDNGWTP NLDSNKEYLQ VDLRFLTMLT AIATQGAISR ETQNGYYVKS   360
YKLEVSTNGE DWMVYRHGKN HKVFQANNDA TEVVLNKLHA PLLTRFVRIR PQTWHSGIAL   420
RLELFGCRVT DAPCSNMLGM LSGLIADSQI SASSTQEYLW SPSAARLVSS RSGWFPRIPQ   480
AQPGEEWLQV DLGTPKTVKG VIIQGARGGD SITAVEARAF VRKFKVSYSL NGKDWEYIQD   540
PRTQQPKLFE GNMHYDTPDI RRFDPIPAQY VRVYPERWSP AGIGMRLEVL GCDWTDSKPT   600
VETLGPTVKS EETTTPYPTE EEATECGENC SFEDDKDLQL PSGFNCNFDF LEEPCGWMYD   660
HAKWLRTTWA SSSSPNDRTF PDDRNFLRLQ SDSQREGQYA RLISPPVHLP RSPVCMEFQY   720
QATGGRGVAL QVVREASQES KLLWVIREDQ GGEWKHGRII LPSYDMEYQI VFEGVIGKGR   780
SGEIAIDDIR ISTDVPLENC MEPISAFAGE NFKVDIPEIH EREGYEDEID DEYEVDWSNS   840
SSATSGSGAP STDKEKSWLY TLDPILITII AMSSLGVLLG ATCAGLLLYC TCSYSGLSSR   900
SCTTLENYNF ELYDGLKHKV KMNHQKCCSE A                                  931

SEQ ID NO: 5         moltype = AA   length = 766
FEATURE              Location/Qualifiers
source               1..766
                     mol_type = protein
                     organism = Homo sapiens
SEQUENCE: 5
```

```
FPTQDHLPAT PRVRLSFKEL KATGTAHFFN FLLLNTTDYRI LLKDEDHDRM YVGSKDYVLS    60
LDLHDINREP LIIHWAASPQ RIEECVLSGK DVNGECGNFV RLIQPWNRTH LYVCGTGAYN   120
PMCTYVNRGR RAQATPWTQT QAVRGRGSRA TDGALRPMPT APRQDYIFYL EPERLESGKG   180
KCPYDPKLDT ASALINEELY AGVYIDFMGT DAAIFRTLGK QTAMRTDQYN SRWLNDPSFI   240
HAELIPDSAE RNDDKLYFFF RERSAEAPQS PAVYARIGRI CLNDDGGHCC LVNKWSTFLK   300
ARLVCSVPGE DGIETHFDEL QDVFVQQTQD VRNPVIYAVF TSSGSVFRGS AVCVYSMADI   360
RMVFNGPFAH KEGPNYQWMP FSGKMPYPRP GTCPGGTFTP SMKSTKDYPD EVINFMRSHP   420
LMYQAVYPLQ RRPLVVRTGA PYRLTTIAVD QVDAADGRYE VLFLGTDRGT VQKVIVLPKD   480
DQELEELMLE EVEVFKDPAP VKTMTISSKR QQLYVASAVG VTHLSLHRCQ AYGAACADCC   540
LARDPYCAWD GQACSRYTAS SKRRSRRQDV RHGNPIRQCR GFNSNANKNA VESVQYGVAG   600
SAAFLECQPR SPQATVKWLF QRDPGDRRRE IRAEDRFLRT EQGLLLRALQ LSDRGLYSCT   660
ATENNFKHVV TRVQLHVLGR DAVHAALFPP LSMSAPPPPG AGPPTPPYQE LAQLLAQPEV   720
GLIHQYCQGY WRHVPPSPRE APGAPRSPEP QDQKKPRNRR HHPPDT                  766

SEQ ID NO: 6            moltype = AA  length = 1896
FEATURE                 Location/Qualifiers
source                  1..1896
                        mol_type = protein
                        organism = Homo sapiens
SEQUENCE: 6
MPLPPRSLQV LLLLLLLLLL LPGMWAEAGL PRAGGGSQPP FRTFSASDWG LTHLVVHEQT    60
GEVYVGAVNR IYKLSGNLTL LRAHVTGPVE DNEKCYPPPS VQSCPHGLGS TDNVNKLLLL   120
DYAANRLLAC GSASQGICQF LRLDDLFKLG EPHHRKEHYL SSVQEAGSMA GVLIAGPPGQ   180
GQAKLFVGTP IDGKSEYFPT LSSRRLMANE EDADMFGFVY QDEFVSSQLK IPSDTLSKFP   240
AFDIYYVYSF RSEQFVYYLT LQLDTQLTSP DAAGEHFFTS KIVRLCVDDP KFYSVEFPI    300
GCEQAGVEYR LVQDAYLSRP GRALAHQLGL AEDEDVLFV VRAGQKNRVK PPKESALCLF    360
TLRAIKEKIK ERIQSCYRGE GKLSLPWLLN KELGCINSPL QIDDDFCGQD FNQPLGGTVT   420
IEGTPLFVDK DDGLTAVAAY DYRGRTVVFA GTRSGRIRKI LVDLSNPGGR PALAYESVVA   480
QEGSPILRDL VLSPNHQYLY AMTEKQVTRV PVESCVQYTS CELCLGSRDP HCGWCVLHSI   540
CSRRDACERA DEPQRFAADL LQCVQLTVQP RNVSVTMSQV PLVLQAWNVP DLSAGVNCSF   600
EDFTESESVL EDGRIHCRSP SAREVAPITR GQGDQRVVKL YLKSETGKK FASVDFVFYN    660
CSVHQSCLSC VNGSFPCHWC KYRHVCTHNV ADCAFLEGRV NVSEDCPQIL PSTQIYVPVG   720
VVKPITLAAR NLPQPQSGQR GYECLFHIPG SPARVTALRF NSSSLQCQNS SYSYEGNDVS   780
DLPVNLSVVW NGNFVIDNPQ NIQAHLYKCP ALRESCGLCL KADPRFECGW CVAERRCSLR   840
HHCAADTPAS WMHARHGSSR CTDPKILKLS PETGPRQGGT RLTITGENLG LRFEDVRLGV   900
RVGKVLCSPV ESEYISAEQI VCEIGDASSV RAHDALVEVC VRDCSPHYRA LSPKRFTFVT   960
PTFYRVSPSR GPLSGGTWIG IEGSHLNAGS DVAVSVGGRP CSFSWRNSRE IRCLTPPGQS  1020
PGSAPIIINI NRAQLTNPEV KYNYTEDPTI LRIDPEWSIN SGGTLLTVTG TNLATVREPR  1080
IRAKYGGIER ENGCLVYNDT TMVCRAPSVA NPVRSPPELG ERPDELGFVM DNVRSLLVLN  1140
STSFLYYPDP VLEPLSPTGL LELKPSSPLI LKGRNLLPPA PGNSRLNYTV LIGSTPCTLT  1200
VSETQLLCEA PNLTGQHKVT VRAGGFEFSP GTLQVYSDSL LTLPAIVGIG GGGGLLLLVI  1260
VAVLIAYKRK SRDADRTLKR LQLQMDNLES RVALECKEAF AELQTDIHEL TNDLDGAGIP  1320
FLDYRTYAMR VLFPGIEDHP VLKEMEVQAN VEKSLTLFGQ LLTKKHFLLT FIRTLEAQRS  1380
FSMRDRGNVA SLIMTALQGE MEYATGHVLKQ LLSDLIEKNL ESKNHPKLLL RRTESVAEKM  1440
LTNWFTFLLY KFLKECAGEP LFMLYCAIKQ QMEKGPIDAI TGEARYSLSE DKLIRQQIDY  1500
KTLTLNCVNP ENENAPEVPV KGLDCDTVTQ AKEKLLDAAY KGVPYSQRPK AADMDLEWRQ  1560
GRMARIILQD EDVTTKIDND WKRLNTLAHY QVTDGSSVAL VPKQTSAYNI SNSSTFTKSL  1620
SRYESMLRTA SSPDSLRSRT PMITPDLESG TKLWHLVKNH DHLDQREGDR GSKMVSEIYL  1680
TRLLATKGTL QKFVDDLFET IFSTAHRGSA LPLAIKYMFD FLDEQADKHQ IHDADVRHTW  1740
KSNCLPLRFW VNVIKNPQFV FDIHKNSITD ACLSVVAQTF MDSCSTSEHK LGKDSPSNKL  1800
LYAKDIPNYK SWVERYYADI AKMPAISDQD MSAYLAEQSR LHLSQFNSMS ALHEIYSYIT  1860
KYKDEILAAL EKDEQARRQR LRSKLEQVVD TMALSS                            1896

SEQ ID NO: 7            moltype = DNA  length = 9071
FEATURE                 Location/Qualifiers
source                  1..9071
                        mol_type = unassigned DNA
                        organism = Homo sapiens
SEQUENCE: 7
atgccgctgc caccgcggag cctgcaggtg ctcctgctgc tgctgctgtt gctgctgctg    60
ctgccgggca tgtgggctga ggcaggcttg cccagggcag gcgggggttc acagcccccc   120
ttccgcacct tctcggccag cgactggggc ctcacccacc tagtggtgca tgagcagaca   180
ggcgaggtgt atgtgggcgc agtgaaccgc atctataagc tgtcggggaa cctgacactg   240
ctgcgggccc acgtcacggg ccctgtggag gacaacgaga agtgctaccc gccgccgtcc   300
gtgcagtcct gccccacgg cctgggcagt actgacaacg tcaacaagct gctgctgctg   360
gactatgccg ctaaccgcct gctggcctgt ggcagcgcct cccagggcat ctgccagttc   420
ctgcgtctgg acgatctctt caaactgggt gagccacacc accgtaagga gcactacctg   480
tccagctgtg aggaggcagg cagcatggcg ggcgtgctca ttgccggggc cccgggccag   540
ggccaggcca agctcttcgt gggcacaccc atcgatgcca agtccgagta cttccccaca   600
ctgtccagcc gtcggctcat ggccaacgag gaggatgccg acatgttcgg cttcgtgtac   660
caggatgagt ttgtgtcatc acagctcaag atcccttcgg acacgctgtc caagttcccg   720
gcctttgaca tctactatgt gtacagcttc cgcagcgagc agtttgtcta ctacctcacg   780
ctgcagctag acacacagct gacctcgcct gatgccgccg gcgagcactt cttcacgtcc   840
aagatcgtgc gcctgtgcgt ggacgacccc aaattctact cggtcgttga gttccccatt   900
ggctgcgagc aggccggtgt ggagtaccgc ctggtgcagg atgcctacct gagccggccc   960
ggccgtgccc tggcccacca gctgggcctg gctgaggacg aggacgtgct gttcactgtg  1020
ttcgcccagg gccagaagaa ccgcgtgaag ccaccaaagg agtcagcact gtgcctgttc  1080
acgctcaggg ccatcaagga gaagattaag gagcgcatcc agtcctgcta ccgtggtgag  1140
ggcaagctct ccctgccgtg gctgctcaac aaggagctgg gctgcatcaa ctcgcccctg  1200
```

```
cagatcgatg acgacttctg cgggcaggac ttcaaccagc ccctgggggg cacagtcacc  1260
attgagggga cgcccctgtt cgtgacaag gatgatggcc tgaccgccgt ggctgcctat   1320
gactatcggg gccgcactgt ggtattcgcc ggcacgcgaa gtggccgcat ccgcaagatc  1380
ctggtggacc tctcaaaccc cggtggccgg cctgccctgg cctacgagag cgtcgtggcc  1440
caggagggca gccccatcct gcgagacctc tcctcagcc ccaaccacca gtacctctac   1500
gccatgaccg agaagcaggt gacgcgggtg cctgtggaga gctgtgtgca gtacacgtcc  1560
tgtgagctgt gtctggggtc acgggacccc cactgtggct ggtgtgtcct gcacagcatc  1620
tgctcgcggc gggacgcctg tgagcgagca gacgagcccc agcgctttgc tgcggacctg  1680
ctgcagtgtg tgcagcccc cgcaatgtgt ctgtcaccat gtcccaggtc                1740
ccacttgtgc tgcaggcctg gaacgtgcct gacctctcag ctggcgtcaa ctgctccttc   1800
gaggacttca cggaatctga gagcgtcctg gaggatggcc ggatccactg ccgctcaccc  1860
tccgcccggg aggtggcgcc catcacgcgg ggccagggag accagcgggt ggtgaaactc   1920
tacctaaagt ccaaggagac agggaagaag tttgcgtctg tggacttcgt cttctacaac  1980
tgcagcgttc accagtcctg cctgtcctgt gtcaacggct cctttccctg ccactggttc  2040
aaataccgcc acgtgtgcac acacaacgtg gctgactgcg ccttcctgga gggccgtgtc  2100
aacgtgtctg aggactgccc acagatcctg ccctccacgc agatctacgt gccagtggga  2160
gtggtaaaac ccatcaccct ggccgcacgg aacctgccac agccacagtc aggccagcgt  2220
ggatatgagt gcctcttcca catcccgggc agcccggccc gtgtcaccgc cctgcgcttc  2280
aacagctcca gcctgcagtg ccagaattcc tcgtactcct acgaggggaa cgatgtcagc  2340
gacctgccag tgaacctgtc agtcgtgtgg aacggcaact ttgtcattga caacccacag  2400
aacatccagg cgcacctcta caagtgcccg gccctgcgcg agagctgcgg cctctgcctc  2460
aaggccgacc cgcgcttcga gtgcggatgg tgcgtgacgg cgccgcgtc ctccctgcga    2520
caccactgcg ctgccgacac acctgcatcg tggatgcacg cgcgtcacgg cagcagtcgc  2580
tgcaccgacc ccaagatcct caagctgtcc ccgagacgg gcccgaggca gggcggcacg    2640
cggctcacta tcacaggcga gaacctgggc ctgcgattcg aagacgtgcg tctgggcgtg   2700
cgcgtgggca aggtgctgtg cagccctgtg gagagcgagt acatcagtgc ggagcagatc  2760
gtctgtgaga tcggggacgc cagctccgtg cgtgcccatg acgccctggt ggaggtgtgt  2820
gtgcgggact gctcaccaca ctaccgcgcc ctgtcaccca agcgcttcac cttcgtgaca  2880
ccaaccttct accgtgtgag cccctcccgt gggcctctgt caggggggcac ctggattggc  2940
atcgagggaa gccacctgaa cgcaggcagt gatgtggctg tgtcggtcgg tggccggccc  3000
tgctccttct cctggaggaa ctcccgtgag atccggtgcc tgacaccccc cgggcagagc  3060
cctggcagcg ctcccatcat catcaacatc aaccgcgccc agctcaccaa ccctgaggtg  3120
aagtacaact acaccgagga ccccaccatc ctgaggatcg accccgagtg gagcatcaac  3180
agcggtggga ccctcctgac ggtcacaggc accaaacctgg ccactgtccg tgaaccccga  3240
atccgggcca agtatggagg cattgagagg gagaacggct gcctggtgta caatgacacc   3300
accatggtat gccgcgcccc gtctgtggcc aaccctgtgc gcagcccacc agagctgggg  3360
gagcggccgg atgagctggg cttcgtcatg gacaacgtgc gctccctgct tgtgctcaac   3420
tccacctcct tcctctacta ccctgacccc gtactggagc cactcagccc cactggcctg  3480
ctggagctga agcccagctc cccactcatc ctcaagggcc ggaacctctt gccacctgca   3540
cccggcaact cccgactcaa ctacacggtg ctcatcggct ccacaccctg taccctcacc  3600
gtgtcggaga cgcaactgct gtgcgaggcg cccaacctca ctgggcagca caaggtcacg    3660
gtgcgggcag gtggcttcga gttctcgcca gggacactgc aggtgtactc ggacagcctg   3720
ctgacgctgc ctgccattgt gggcattggc ggaggcgggg gtctcctgct gctggtcatg   3780
gtggctgtgc tcatcgccta caagcgcaag tcacgagatg ctgaccgcac actcaagcgg  3840
ctgcagctcc agatggacaa cctggagtcc cgcgtggccc tcgaatgcaa ggaagccttt  3900
gcagagctgc agacagacat ccacgagctg accaatgacc tggacggtgc cggcatcccc  3960
ttcctttgact accggacata tgccatgcgg gtgctctttc tgggatcga gacccaccct    4020
gtgctcaagg agatggaggt gcaggccaat gtggagaagt cgctgacact gttcgggcag  4080
ctgctgacca agaagcactt cctgctgacc ttcatccgca cgctggaggc acagcgcagc  4140
ttctccatgc gcgaccgcgg gaatgtggcc tcgctcatca tgacgccct gcagggcgag  4200
atggaatacg ccacaggcgt gctcaagcag ctgctttccg acctcatcga gaagaacctg  4260
gagagcaaga accaccccaa gctgctactg cgccggactg agtcggtggc agagaagatg  4320
ctaactaact ggttcacctt cctcttgtat aagttcctca aggagtgcgc tggggagccg  4380
ctgttcatgc tgtactgcgc catcaagcag cagatggaga agggcccat tgacgccatc    4440
acgggtgcagc cacgctactc cctgagtgag gacaagctca tccggcagca gattgactac   4500
aagacactga ccctgaactg tgtgaaccct gagaatgaga atgcacctga ggtgccggtg  4560
aagggggctgg actgtgacac ggtcacccag gccaaggaga agctgctgga cgctgcctac  4620
aagggcgtgc cctactccca gcggcccaag gccgcggaca tggacctgga gtggcgccag  4680
ggccgcatcat cctgcaggac gaggacgtca ccaccaagat tgacaacgat                4740
tggaagaggc tgaacacact ggctcactac caggtgacag acgggtcctc ggtggcactg   4800
gtgcccaagc agacgtccgc ctacaacatc tccaactcct ccaccttcac caagtccctc  4860
agcagatacg agagcatgct gcgcacggcc agcagcccg acagcctgcg ctcgcgcacg    4920
cccatgatca cgcccgacct ggagagcggc accaagctgt ggcacctggt gaagaaccac  4980
gaccacctga ccagcgtgtga gggtgaccgc ggcagcagga gtgtctcgga gatctacttg  5040
acacggctac tggccaccaa gggcacactg cagaagtttg tggacgacct gtttgagacc  5100
atcttcagca cggcacaccg gggctcagcc ctgccgctgg ccatcaagta catgttcgac  5160
ttcctggatg agcaggccga caagcaccag atccacgatg ctgacgtgcg ccacacctgg  5220
aagagcaact gcctgccccct cgcgcttctgg gtgaacgtga tcaagaaccc acagtttgtg  5280
ttcgacattc acaagaacag catcacggac gcctgctttg cggtggtggc ccagaccttc  5340
atggactcct gctccaccctc tgagcacaag ctgggcaagg actcacctcc aacaagctg   5400
ctctacgcca aggacatccc caactacaag agctgggtgg agaggtacta tgcagacatc  5460
gccaagatgc cagccatcag cgaccaggac atgagtgcgt atctggctga gcagtcccgc  5520
ctgcacctga gccagttcaa cagcatgagc gccttgcacg agatctactc ctacatcacc  5580
aagtacaagg atgagatcct ggcagcctg gagaaggatg agcaggcggg cggcagcgg     5640
ctgcggagca agctggagca ggtggtggac acgatggccc tgagcagctg agccccagct  5700
gtgatcatcc agcatgatgc agcgtgagga cagctgagca gggaccggga cagccctcac   5760
cgcatgcgtg tggagtgtcc ggtggtgctc gggccgccgc agtgcagcga ctgcccggcc   5820
ctccctcccc tgcctcaccc ggtcgggtcc cggctcttcc tgtgtggagg tgatggtacc   5880
tgccacacca cagctgcgca cacagctgct tgctcagggg ccgggacagc actgggtgct   5940
```

```
caggctggcc aaggaccttc attgcctggc aagagctgcc cagtggcctt catgggagaa 6000
gggctgacct ctgaggggct gagggggtgag gccagggccc tccagggggga ggggtagcca 6060
gcttgggctg tcccccttgag accaggacaa gaggctgggg gtgtcagcat tcccagcttt 6120
ccaagctgcc cccaggcggc agagtctgag ggtcccgggg cccggttggc agctggagaa 6180
agaggcaaaa agcccgtagc cgggcaagag gagctcaagt cggtctgggc ccgttgccac 6240
cgactcccac ctccagcacc catgcccgct gcaccgctgc catcctcaga ttcaccgcgt 6300
gctctgcgcg gccgaggccg gagcaccaca tccacctcgc cccagagagg ctctgctccc 6360
tcctatggag gggctgtggg ccaggctgct cagactcctg ggtggcttcc agacggaccg 6420
ggcagcccct ctccgtcctc agggctgtgc ctctgggagc cactgggcca ggggcccgg 6480
gtcgcagaga gcacgttccc gttatttatt cccctccgcg tcctacacag gctgccctgg 6540
cagctgtctt caagggtagg ctgagctccc caccctggag cccctgaggg cggcccctga 6600
gcactcctct ctctccactc tctctgtccc tgcccagcg gcttccagtg tggcatctca 6660
gcagtgtcct ggccctcca gagcagtggg acatctgggg actgtttttg tgtttagggg 6720
aaaaaattct gctgcactct gcttgggcct tgaggtctgt ggcagggctc ctctggcccg 6780
cagtggcctg gatctatctg ggccatgagt gacgggcagt gaccagaggg actggaggcc 6840
agcggtgtcc acccttgccc tcagcaagag agaatgcatt cttaaaagaa agctgtacat 6900
gtatatatat gcatatatat atatgtggct ctagcctcag gctccagccc cagtgggggta 6960
ctgtacagtt aactgaagaa gaattttaaa gacgatttga acaagaaaat gaaggcagtg 7020
ggaaagcaat gccaaatggt tgtggagaaa gtggccggag cctccctgga gtggagcagc 7080
cctgaagcct gtgcccccg acctgcgggc cgctgttttg gtttgacatg acaaggaaag 7140
gacttcctgc tgacctgag agcctctggg gtgccgcggc accacggggc atgcatgatt 7200
gtgctagcgt ttagtctgag ttgatctttt taaaactgca agtgttgaat actagaggtt 7260
gttagaccct tttttatgtt ttttaattaa tcagtcactt gtaaaagcaa acaagcggtc 7320
catccccttt tcaaggtcac tttttttgatg gtaccgaaga tcccatggac attaagggac 7380
agctaactgt ggccagactc agcccccatgt ccttggccag gcccaaggag aggactcggc 7440
cccatggggt gtgccagtct tgcagtccgc cccagctgag tagcgtgagc cagatgacgc 7500
cacagagacc cgcctcttcc ctgaacgcgg gtcggtgtgg agtcagtgac tgctgactca 7560
gggagctcct tggccccgtg ggcactgtgc cagggctggg gccttctgct gctgccacac 7620
ccagctcagg cctgggccag cccctgcccc cagcccactg aggggggtggg cttactccct 7680
gggcagtctt gggggccaga gctgaggcca gtccatatta cagtggctgg gctgttttt 7740
tcagtagccc ctagcattgg ctgggattcc tgttcctggg tgcgcctcca cctcccttct 7800
gatgtttcct ggctatggtg gggtgggaac ctcagtttcc cccaaagtct tccctggatg 7860
ctggcttcag gttgaagtcc ctggttcttc cagttcctca cgggttaggt aggggctcct 7920
gcatcacctt cagaatccag ttccaacccc cactctcctt aggccttgtg ctctgctctg 7980
ccctgccagg ctgcccttgt ccatgtgagt agcatgggcg ggtggtgggg acggcagtgg 8040
tgatgaaggg ggtgcaccac aggcctcatg aagcagttcc cacatgggcg tgtggctggg 8100
gcgtggccac cacagagcac atggctgtgt ctaggcgcaa gcactttagc agtatctgtt 8160
tacatgcgca aggatcaagc cgactacctg tgctgtctac tgggacagca gtctccgagc 8220
tactccgtac ctccctctgc caggtcgtgg agttaggccc cagtccctac ttgtcactgg 8280
ttcccactgt gctcctaact gtgcagcacc tgggagctct ggcctggggc tggaggccct 8340
ggtaggagct gcagttggag gccgttctgt gcccagcagc ggtgagcggc tcccatgggc 8400
cctgtgtctg cagggagcca gggctgcggc acatgtgctg tgaaactggc acccacctgg 8460
cgtgctgctg ccgccacttg cttcctgcag cacctcctac cctgctccgt gtcctccctc 8520
tccccgcgcc tggctcagga gtgctggaaa agctcacgcc tcggcctggg agcctggcct 8580
cttgatatac ctcgagcttc ccctgtgctc cccagcccca ggaccactgg ccccttggcc 8640
tgagggggctg ggggccccac gacctgcagc gtcgagtccg ggagagagcc cggagcggcg 8700
tgccatctcg gctcggcctt gctgagagcc tccgccctgg ctttctccct gtctggattc 8760
agtggctcac gttggtgcta cacagctaga atagatatat ttagagagag agatattttt 8820
aagacaaagc ccacaattag ctgtcctttta acaccgcaga acccctccc agaagaagag 8880
cgatccctcg gacggtccgg gcgggcaccc tcagccgggc tctttgcaga agcagcaccg 8940
ctgactgtgg gcccggccct cagatgtgta catatacggc tatttcctat tttactgttc 9000
ttcagattta gtacttgtaa ataaacacac acattaagga gagattaaac attttgcta 9060
aaagctaaaa a                                                       9071
```

METHODS AND COMPOSITIONS FOR IMMUNOMODULATION

CROSS-REFERENCE TO RELATED APPLICATIONS

This application is a divisional under 35 U.S.C. § 121 of U.S. application Ser. No. 16/561,177 filed Sep. 5, 2019 now abandoned, which is a divisional under 35 U.S.C. § 121 of U.S. application Ser. No. 15/314,970 filed Nov. 30, 2016 issued as U.S. Pat. No. 10,456,445 on Oct. 29, 2019, which is a 35 U.S.C. § 371 National Phase Entry Application of International Application No. PCT/US2015/033510 filed Jun. 1, 2015, which designates the U.S. and claims benefit under 35 U.S.C. § 119(e) of U.S. Provisional Application No. 62/006,441 filed Jun. 2, 2014, the contents of which are incorporated herein by reference in their entireties.

GOVERNMENT SUPPORT

This invention was made with government support under grant number AI092305 awarded by the National Institutes of Health. The Government has certain rights in the invention.

SEQUENCE LISTING

The instant application contains a Sequence Listing that has been submitted in XML format via Patent Center and is hereby incorporated by reference in its entirety. Said XML copy, created on Mar. 29, 2023, is named "701039-080592USD2_SL.xml" and is 30,677 bytes in size.

TECHNICAL FIELD

The technology described herein relates to immunomodulation.

BACKGROUND

The class 3 family of semaphorins (Sema3A-G) bind to Neuropilin and Plexin family proteins and elicit regulatory signals that inhibit cellular migration and proliferation. Specifically, the binding of SEMA3A to NRP-1 and SEMA3F to NRP-2 elicits inhibitory signals in neuronal cells and in vascular endothelial cells.

SUMMARY

As described herein, the inventors have discovered that Sema3F has immunomodulatory properties and in part this effect is mediated via interaction with NRP-2 and Plexin A1. Accordingly, provided herein are immunomodulatory methods based on the manipulation of SEMA3F binding to its receptors and associated signaling. Non-limiting examples include suppression of the immune system or immune response by increasing or enhancing the interaction of Sema3F and NRP-2, and/or upregulating the immune system or immune response by decreasing the activity and/or interaction of Sema3F and NRP-2.

In one aspect, described herein is a method of suppressing the immune system in a subject, the method comprising administering a Sema3F agonist to a subject in need thereof. In one aspect, described herein is a method of suppressing allograft rejection, the method comprising administering a Sema3F agonist to an allograft recipient, whereby immune rejection of the allograft is suppressed. In one aspect, described herein is a method of treating an inflammatory condition in a subject in need of thereof, the method comprising administering a Sema3F agonist to the subject. In some embodiments, the inflammatory condition is an autoimmune disease. In some embodiments, the autoimmune disease is selected from the group consisting of Type 1 diabetes; systemic lupus erythematosus; rheumatoid arthritis; psoriasis; inflammatory bowel disease; Crohn's disease; and autoimmune thyroiditis. In some embodiments, the inflammatory condition is a local condition. In some embodiments, the local inflammatory condition is selected from the group consisting of a rash and an allergic reaction.

In some embodiments, the Sema3F agonist is a Sema3F polypeptide or a nucleic acid encoding a Sema3F polypeptide. In some embodiments, the Sema3F polypeptide comprises the sequence of SEQ ID NO: 5. In some embodiments, the Sema3F polypeptide can bind a Sema3F receptor. In some embodiments, the Sema3F polypeptide can bind a domain of NRP-2 selected from the group consisting of the A1; the A2; the B1; and the B2 domain. In some embodiments, the Sema3F agonist is a furin-like inhibitor. In some embodiments, the Sema3F agonist is administered intravenously. In some embodiments, the Sema3F agonist is administered intramuscularly, subcutaneously, or intradermally. In some embodiments, the Sema3F agonist is administered locally to a site of inflammation. In some embodiments, the method further comprises administering an additional anti-inflammatory agent. In some embodiments, the additional anti-inflammatory agent is selected from the group consisting of a steroid; a calcineurin inhibitor; an mTOR inhibitor (e.g. rapamycin) or an analogue thereof; and an anti-proliferative agent.

In one aspect, described herein is a method of increasing an immune response in a subject in need thereof, the method comprising administering one or more of a Sema3F inhibitor or NRP-2 inhibitor or Plexin A1 inhibitor to the subject. In some embodiments, the Sema3F inhibitor is an anti-Sema3F antibody reagent. In some embodiments, the NRP-2 inhibitor is an anti-NRP-2 antibody reagent. In some embodiments, the Sema3F inhibitor is a soluble NRP-2 receptor. In some embodiments, the Sema3F inhibitor is a soluble fragment of the NRP-2 receptor comprising at least one domain selected from the group consisting of the A1, the A2, the B1 or the B2 domain. In some embodiments, the Sema3F inhibitor is a furin-like polypeptide or a nucleic acid encoding a furin-like polypeptide.

BRIEF DESCRIPTION OF THE DRAWINGS

Injection of Sema3F-expressing cells in combination with a blocking anti-Sema3F antibody does not result in prolonged graft survival

FIG. 26 depicts a graph of NPR-2 expression as evaluated by qPCR on unactivated and mitogen (Anti-CD3/CD28) activated human CD4+ T cells. FIG. 26B depicts a graph of NRP-2 expression evaluated by FACS on the CD4+ subset of human peripheral blood cells isolated by Ficoll separation. FIG. 26C depicts a graph of CD4, FoxP3 and NRP-2 protein levels in peripheral blood cells as evaluated by FACS. This data is similar to that shown in FIG. 22.

FIGS. 27A-27F show data demonstrating expression of NRP-2 on murine CD4+ T cells. FIG. 27A demonstrates FACS analysis of NRP-2 on CD4+ T cells within murine spleen and lymph node. FIG. 27B depicts graphs of CD4+ T cells isolated by negative selection from Murine Spleen. Expression of NRP-2 was evaluated by qPCR on unactivated and mitogen (Anti-CD3/CD28) activated cells. FIG. 27C depicts graphs of Plexin A family molecule expression on isolated CD4+ T cells. FIG. 27D depicts expression of NRP-2 on Foxp3+ and Foxp3 negative subsets of CD4+ T cells isolated by negative selection from Murine Spleen. FIG. 27E depicts NRP-2 expression on isolated Splenic CD4+ T cells that were mitogen activated (anti-CD3-1 mcg/ml). FIG. 27F depicts NRP-1/2 expression on CD4+ T cells driven to differentiation into induced Treg cells in standard culture medium (mitogen+ TGFb+anti-IL-4+anti-IFNg+retinoic acid). These data are similar to that shown in FIGS. 7 and 9.

FIG. 28A depicts U87MG cells untreated (control) or following treatment with SEMA3F (640 ng/ml) for 30 minutes. Cell lysates were evaluated by phosphoprotein kinase antibody array. The intensity of each dot/phosphoprotein was measured using Image J software, as shown in Table 1. FIG. 28B depicts results of the array validated by Western blot analysis. FIG. 28C depicts U87MG cells treated with SEMA3F (640 ng/ml) as a time course up to 60 minutes and were analyzed by Western blot. FIGS. 28B-28C are representative of 3 independent experiments. FIG. 28D depicts U87MG, Jurkat and HUVEC cells treated with SEMA3F (200, 600, 1800 ng/ml, bars from left to right) for 15 minutes (grey bars) or 30 minutes (black bars); as a positive control, HUVEC were treated with VEGF-A (25 ng/ml) for 15 and 30 minutes. In addition, HUVEC were pre-treated with SEMA3F (1800 ng/ml) or PBS as a control for 30 minutes and subsequently VEGF-A (25 ng/ml) was added to the culture for 15 and 30 minutes. PI-3K activity was analyzed by ELISA according to the manufacturer's instructions. Data represent the mean±SD of 3 experiments.

FIGS. 29A-29D show data demonstrating that SEMA3F disrupts both mTORC1 and mTORC2 complex formation. FIG. 29A depicts U87MG cells treated with SEMA3F (640 ng/ml) for 30 minutes and subjected to immunoprecipitation and Western blot analysis with anti-mTOR, -raptor and -rictor as illustrated. FIG. 29B depicts U87MG cells treated with rapamycin (10 nM) or Torin 1 (10 nM) for 30 minutes, prior to SEMA3F (640 ng/ml) treatment for 60 minutes; lysates were analyzed by Western blot. FIG. 29C depicts bar graphs representing densitometric analysis of the illustrated blot showing the fold change in intensity (mean±SD) relative to the untreated control (*, p <0.01; **, p<0.001 vs. untreated control). FIG. 29D depicts U87MG cells transiently transfected with a pcDNA3.1 empty vector or with constitutively active Akt (2DAkt). Cells were treated with SEMA3F (640 ng/ml) and lysates were analyzed by Western blot. All data are representative of 3 independent experiments.

FIG. 30A depicts U87MG cells treated with SEMA3F (640 ng/ml), rapamycin (10 nM) or Torin 1 (10 nM) for 30 minutes. Subsequently, cells were stained with Alexa Fluor 488 phalloidin and Hoechst 33342 to identify F-actin cytoskeleton stress fibers and cellular nuclei, respectively. Representative cellular staining of is shown in each panel; the bar graph shows the mean±SD number of fibers/cell in an average of 3 independent experiments. The scale bar indicates 20 μm. FIG. 30B depicts U87MG cells transiently transfected with a pcDNA3.1 empty vector or with a wild type (WT) mTOR plasmid and after 18 hours treated with SEMA3F (640 ng/ml) for 30 minutes. Cells were stained as described above in FIG. 30A. Representative cellular staining is shown; bar graph represents the number of fibers/cell (mean±SD) from 3 independent experiments. FIG. 30C depicts U87MG cells transfected with control siRNA or with raptor- or rictor-specific siRNAs (20 nM). After 48 hours, they were treated with SEMA3F for 30 minutes and stained with Alexa Fluor 488 phalloidin and Hoechst 33342 as above. The number of stress fibers was evaluated in 3 independent experiments and shown as the mean±SD. FIG. 30D depicts U87MG cells transiently transfected with pcDNA3.1 empty vector or with our WT mTOR plasmid. After 18 hours, the cells were treated with SEMA3F (640 ng/ml) for 10 minutes and RhoA activity was evaluated. FIG. 30E depicts U87MG cells transfected with control siRNA or with raptor- or rictor-specific siRNAs (20 nM), were treated with SEMA3F (640 ng/ml) for 10 minutes and RhoA activity was analyzed. In FIGS. 30D-30E, the intensity of active RhoA was normalized to respective total RhoA; the numbers below each gel lane represent the fold-change in intensity relative to control. FIGS. 30D-30E are representative of 3 independent experiments.

FIGS. 31A-31B depict U87MG cells transiently co-transfected with a full-length human VEGF promoter luciferase plasmid and a pGL4.74 [hRluc/TK] plasmid as an internal control. Cells were treated with SEMA3F (640 ng/ml for 30 minutes) prior to the addition of DFO (250 μM) or the culture of cells in a hypoxia chamber (1% 02). After 18 hours, VEGF promoter luciferase activity was analyzed. FIG. 31C depicts a graph of U87MG cells transiently cotransfected with our VEGF promoter luciferase and pGL4.74 [hRluc/TK] plasmids and with either a pcDNA3.1 empty vector or our constitutively active Akt (2DAkt). The cells were treated with SEMA3F for 30 minutes prior to the addition of DFO. After 18 hours, VEGF promoter luciferase activity was analyzed. FIG. 31D depicts a graph of parental U87MG cells with SEMA3F, rapamycin (10 nM), Torin 1 (10 nM) alone or in combination as indicated for 30 minutes prior to the addition of DFO, and culture supernatants were collected after 18 hours; VEGF protein levels were analyzed by ELISA. In each panel data are representative of 3 independent experiments. Bar graphs represent the mean±SD of n=3 experiments performed in triplicate, *, p<0.01 vs. control.

FIG. 32A depicts parental U87MG cells (Mock) and human SEMA3F stable clones (S3F) implanted into nude mice subcutaneously ($1 \times 10^6$ cells/injection). The insert shows Western blot analysis of SEMA3F expression in each cell line. Tumor size was measured using standard calipers at the indicated time points. Numbers in parentheses represent the number of animals in each group. FIG. 32B depicts representative immunohistochemical anti-CD31 staining of tumors harvested after 24 days. FIG. 32C depicts U87MG cells ($1 \times 10^6$ cells/injection) administrated subcutaneously into nude mice. After 2 days, control (Ad-Cont) or human SEMA3F-His (Ad-3F)-recombinant adenovirus ($1 \times 10^9$ pfu) were injected intravenously via the tail vein. Tumor size was measured using a standard calipers at the indicated time points. Numbers in parentheses represent the number of animals in each group. Mice were sacrificed on day 14. The insert shows SEMA3F expression within the liver (on day 14) by Western blot analysis using an anti-His antibody. FIG. 32D depicts representative immunohistochemical staining of tumors with anti-CD31. FIG. 32E depicts western blot analysis of Akt/mTOR signaling pathway within tumor samples. FIGS. 32B, 32D, and 32E are representative results of 3 independent experiments.

FIG. 34A depicts a Western blot of the expression of pAkt, pmTOR and pS6K in U87MG cells treated with SEMA3F or PBS for 60 minutes and. FIG. 34B depicts a Western blot. U87MG cells were transfected with control or Plexin A1-specific siRNA (20 nM). After 48 hours, cells were treated with SEMA3F (640 ng/ml) for 30 and 60 minutes, and were analyzed by Western blot. FIG. 34C depicts NRP2 and Plexin A1 expression analyzed by Western blot with multiple cell lines. FIG. 34D depicts a Western blot of multiple NRP2-expressing cell lines were treated with SEMA3F for 30 minutes. All data presented are representative of 3 independent experiments.

FIG. 34A depicts a Western blot. U87MG cells were transiently transfected with a pcDNA3.1 empty vector or with constitutively active Akt (2DAkt). Cells were treated with SEMA3F (640 ng/ml) and lysates were analyzed by Western blot. FIG. 35B depicts a Western blot. U87MG cells were transiently transfected with a pcDNA3.1 empty vector or with 2DAkt. Cells were treated with SEMA3F (640 ng/ml) for 30 minutes and were subjected to immunoprecipitation and Western blot analysis with anti-mTOR, and anti-rictor as illustrated.

In FIGS. 2, 6 and 32 an Adenovirus containing Sema3F or an empty control was administered into mice. In this Figure, it is demonstrated that this approach results in Sema3F production. Shown on the right is a Western Blot, illustrating the infection and production of Sema3F by the liver. Shown on the left, by ELISA, it is observed that Sema3F levels peak on day 14 following administration. Thus, for FIGS. 2, 6 and 32 it is likely that Sema3F peaked in expression 14 days after administration and that levels decreased after day 23.

DETAILED DESCRIPTION

Figure 1:
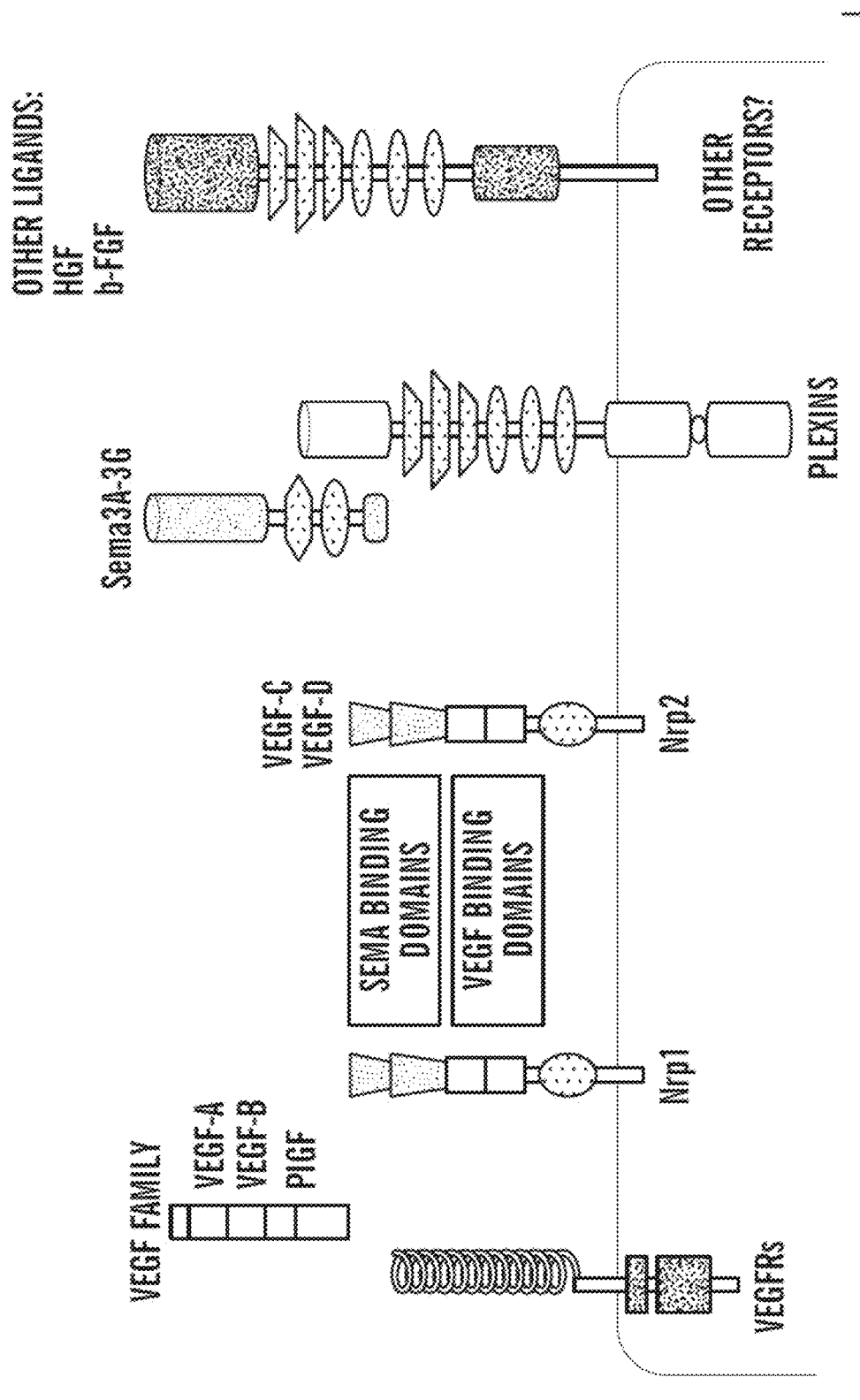
FIG. 1 depicts a schematic illustrating that Neuropilin-1 and Neuropilin-2 have both a Semaphorin binding domain and VEGF binding domain (modified from Bagri et al. 2009).

Described herein are immunomodulatory methods based upon the inventors' discovery that the interaction of Sema3F and NRP-2 functions to suppress the immune system. Accordingly, increasing or enhancing this interaction can suppress an immune response, while inhibiting or decreasing the interaction can upregulate an immune response.

In one aspect, described herein is a method of suppressing the immune system in a subject, the method comprising administering a Sema3F agonist to a subject in need thereof. In some embodiments, suppression of the immune system can comprise treating an inflammatory condition. In some embodiments, suppression of the immune system can comprise suppressing graft rejection (e.g., allograft rejection) or the like. In one aspect, described herein is a method of inhibiting Akt/mTOR signaling in a cell, the method comprising contacting the cell with a Sema3F agonist. In one aspect, described herein is a method of inhibiting Akt/mTOR signaling in a subject, the method comprising administering a Sema3F agonist to a subject in need thereof.

As used herein, "suppression of the immune system" refers to decreasing or inhibiting the immune function of an animal, as measured by any parameter of the various immune functions of the immune system. Non-limiting examples of parameters of immune function can include the magnitude of the antibody response, the response of a B cell, the response of a T cell, the proliferation of T cells, the production of immunomodulatory cytokines, and/or the response to an antigen (e.g. to allogenic or xenogenic cells). Conversely, "stimulation of the immune system" refers to an increase or activation of the immune function of an animal, as measured by any parameter of the various immune functions of the immune system.

As used herein, "graft rejection" or "transplant rejection" refers to any immunologically mediated hyperacute, acute, or chronic injury to a tissue or organ derived from a source other than the host. The term thus encompasses both cellular and antibody-mediated rejection, as well as rejection of both allografts and xenografts.

In some embodiments, suppressing the immune system can comprise suppressing graft vs. host disease. "Graft-versus-host disease" (GVHD) is a reaction of donated tissue against a patient's own tissue. GVHD is seen most often with bone marrow transplant, but can occur with the transplant of other tissues or cells. GVHD is seen most often in cases where the tissue donor is unrelated to the patient or when the donor is related to the patient but not a perfect match. There are two forms of GVHD: an early form called acute GVHD that occurs soon after the transplant when white cells are on the rise, and a late form called chronic GVHD.

As used herein, "inflammation" refers to the complex biological response to harmful stimuli, such as pathogens, damaged cells, or irritants. Inflammation is a protective attempt by the organism to remove the injurious stimuli as well as initiate the healing process for the tissue. Accordingly, the term "inflammation" includes any cellular process that leads to the production of pro-inflammatory cytokines, inflammation mediators and/or the related downstream cellular events resulting from the actions of the cytokines thus produced, for example, fever, fluid accumulation, swelling, abscess formation, and cell death. Pro-inflammatory cytokines and inflammation mediators include, but are not limited to, IL-1-alpha, IL-1-beta, IL-6, IL-8, IL-11, IL-12, IL-17, IL-18, TNF-alpha, leukocyte inhibitory factor (LIF), IFN-gamma, Oncostatin M (OSM), ciliary neurotrophic factor (CNTF), TGF-beta, granulocyte-macrophage colony stimulating factor (GM-CSF), and chemokines that chemoattract inflammatory cells. Inflammation can include both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistiocytic and/or granulomatous response.

An inflammatory condition is any disease state characterized by inflammatory tissues (for example, infiltrates of leukocytes such as lymphocytes, neutrophils, macrophages, eosinophils, mast cells, basophils and dendritic cells) or inflammatory processes which provoke or contribute to the abnormal clinical and histological characteristics of the disease state. Inflammatory conditions include, but are not limited to, inflammatory conditions of the skin, inflammatory conditions of the lung, inflammatory conditions of the joints, inflammatory conditions of the gut, inflammatory conditions of the eye, inflammatory conditions of the endocrine system, inflammatory conditions of the cardiovascular system, inflammatory conditions of the kidneys, inflammatory conditions of the liver, inflammatory conditions of the central nervous system, or sepsis-associated conditions. In some embodiments, the inflammatory condition is associated with wound healing. In some embodiments, the inflammation to be treated according to the methods described herein can be skin inflammation; inflammation caused by substance abuse or drug addiction; inflammation associated with infection; inflammation of the cornea; inflammation of the retina; inflammation of the spinal cord; inflammation associated with organ regeneration; and pulmonary inflammation.

In some embodiments, an inflammatory condition can be an autoimmune disease. Non-limiting examples of autoimmune diseases can include: Type 1 diabetes; systemic lupus erythematosus; rheumatoid arthritis; psoriasis; inflammatory bowel disease; Crohn's disease; and autoimmune thyroiditis. Autoimmune disease are well known in the art, for example, see "Automimmue Diseases Research Plan" Autoimmune Disease Coordinating Committee, NIH Publication No. 03-510, December 2002; which is incorporated by reference herein in its entirety.

In some embodiments, a subject in need of treatment for inflammation, wound healing, or pain management can be a subject having, or diagnosed as having temporomandibular joint disorders; COPD; smoke-induced lung injury; renal dialysis associated disorders; spinal cord injury; graft vs. host disease; bone marrow transplant or complications thereof; infection; trauma; pain; incisions; surgical incisions; a chronic pain disorder; a chronic bone disorder; mastitis; and joint disease. In some embodiments, trauma can include battle-related injuries or tissue damage occurring during a surgery. Smoke-induced lung injury can result from exposure to tobacco smoke, environmental pollutants (e.g. smog or forest fires), or industrial exposure. By way of non-limiting example, inflammatory conditions can be inflammatory conditions of the skin, such as Sweet's syndrome, pyoderma gangrenosum, subcorneal pustular dermatosis, erythema elevatum diutinum, Behcet's disease or acute generalized exanthematous pustulosis, a bullous disorder, psoriasis, a condition resulting in pustular lesions, acne, acne vulgaris, dermatitis (e.g. contact dermatitis, atopic dermatitis, seborrheic dermatitis, eczematous dermatitides, eczema craquelee, photoallergic dermatitis, phototoxicdermatitis, phytophotodermatitis, radiation dermatitis, stasis dermatitis or allergic contact dermatitis), eczema, ulcers and erosions resulting from trauma, burns, ischemia of the skin or mucous membranes, several forms of ichthyoses, epidermolysis bullosae, hypertrophic scars, keloids, cutaneous changes of intrinsic aging, photoaging, frictional blistering caused by mechanical shearing of the skin, cutaneous atrophy resulting from the topical use of corticosteroids, and inflammation of mucous membranes (e.g. cheilitis, chapped lips, nasal irritation, mucositis and vulvovaginitis).

By way of non-limiting example, inflammatory conditions can be inflammatory conditions of the lung, such as asthma, bronchitis, chronic bronchitis, bronchiolitis, pneumonia, sinusitis, emphysema, adult respiratory distress syndrome, pulmonary inflammation, pulmonary fibrosis, and cystic fibrosis (which may additionally or alternatively involve the gastro-intestinal tract or other tissue(s)). By way of non-limiting example, inflammatory conditions can be inflammatory conditions of the joints, such as rheumatoid arthritis, rheumatoid spondylitis, juvenile rheumatoid arthritis, osteoarthritis, gouty arthritis, infectious arthritis, psoriatic arthritis, and other arthritic conditions. By way of non-limiting example, inflammatory conditions can be inflammatory conditions of the gut or bowel, such as inflammatory bowel disease, Crohn's disease, ulcerative colitis and distal proctitis. By way of non-limiting example, inflammatory conditions can be inflammatory conditions of the eye, such as dry eye syndrome, uveitis (including iritis), conjunctivitis, scleritis, and keratoconjunctivitis sicca. By way of non-limiting example, inflammatory conditions can be inflammatory conditions of the endocrine system, such as autoimmune thyroiditis (Hashimoto's disease), Graves' disease, Type I diabetes, and acute and chronic inflammation of the adrenal cortex. By way of non-limiting example, inflammatory conditions can be inflammatory conditions of the cardiovascular system, such as coronary infarct damage, peripheral vascular disease, myocarditis, vasculitis, revascularization of stenosis, atherosclerosis, and vascular disease associated with Type II diabetes. By way of non-limiting example, inflammatory conditions can be inflammatory conditions of the kidneys, such as glomerulonephritis, interstitial nephritis, lupus nephritis, and nephritis secondary to Wegener's disease, acute renal failure secondary to acute nephritis, post-obstructive syndrome and tubular ischemia. By way of non-limiting example, inflammatory conditions can be inflammatory conditions of the liver, such as hepatitis (arising from viral infection, autoimmune responses, drug treatments, toxins, environmental agents, or as a secondary consequence of a primary disorder), biliary atresia, primary biliary cirrhosis and primary sclerosing cholangitis. By way of non-limiting example, inflammatory conditions can be inflammatory conditions of the central nervous system, such as multiple sclerosis and neurodegenerative diseases such as Alzheimer's disease or dementia associated with HIV infection. By way of non-limiting example, inflammatory conditions can be inflammatory conditions of the central nervous system, such as MS; all types of encephalitis and meningitis; acute disseminated encephalomyelitis; acute transverse myelitis; neuromyelitis optica; focal demyelinating syndromes (e.g., Balo's concentric sclerosis and Marburg variant of MS); progressive multifocal leukoencephalopathy; subacute sclerosing panencephalitis; acute haemorrhagic leucoencephalitis (Hurst's disease); human T-lymphotropic virus type-1 associated myelopathy/tropical spactic paraparesis; Devic's disease; human immunodeficiency virus encephalopathy; human immunodeficiency virus vacuolar myelopathy; peripheral neuropathies; Guillame-Barre Syndrome and other immune mediated neuropathies; and myasthenia gravis. By way of non-limiting example, inflammatory conditions can be sepsis-associated conditions, such as systemic inflammatory response syndrome (SIRS), septic shock or multiple organ dysfunction syndrome (MODS). Further non-limiting examples of inflammatory conditions include, endotoxin shock, periodontal disease, polychondritis; periarticular disorders; pancreatitis; system lupus erythematosus; Sjogren's syndrome; vasculitis sarcoidosis amyloidosis; allergies; anaphylaxis; systemic mastocytosis; pelvic inflammatory disease; multiple sclerosis; multiple sclerosis (MS); celiac disease, Guillain-Barre syndrome, sclerosing cholangitis, autoimmune hepatitis, Raynaud's phenomenon, Goodpasture's syndrome, Wegener's granulomatosis, polymyalgia rheumatica, temporal arteritis/giant cell arteritis, chronic fatigue syndrome CFS), autoimmune Addison's Disease, ankylosing spondylitis, Acute disseminated encephalomyelitis, antiphospholipid antibody syndrome, aplastic anemia, idiopathic thrombocytopenia purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, fibromyalgia (FM), autoinflammatory PAPA syndrome, Familial Mediaterranean Fever, polymyalgia rheumatica, polyarteritis nodosa, churg strauss syndrome; fibrosing alveolitis, hypersensitivity pneumonitis, allergic aspergillosis, cryptogenic pulmonary eosinophilia, bronchiolitis obliterans organising pneumonia; urticaria; lupoid hepatitis; familial cold autoinflammatory syndrome, Muckle-Wells syndrome, the neonatal onset multisystem inflammatory disease, graft rejection (including allograft rejection and graft-v-host disease), otitis, chronic obstructive pulmonary disease, sinusitis, chronic prostatitis, reperfusion injury, silicosis, inflammatory myopathies, hypersensitivities and migraines. In some embodiments, an inflammatory condition is associated with an infection, e.g. viral, bacterial, fungal, parasite or prion infections. In some embodiments, an inflammatory condition is associated with an allergic response. In some embodiments, an inflammatory condition is associated with a pollutant (e.g. asbestosis, silicosis, or berylliosis).

In some embodiments, the inflammatory condition can be a local condition, e.g., a rash or allergic reaction.

In some embodiments, the inflammation is associated with a wound. In some embodiments, the technology described herein relates to methods of promoting wound healing. As used herein, "wound" refers broadly to injuries to an organ or tissue of an organism that typically involves division of tissue or rupture of a membrane (e.g., skin), due to external violence, a mechanical agency, or infectious disease. A wound can be an epithelial, endothelial, connective tissue, ocular, or any other kind of wound in which the strength and/or integrity of a tissue has been reduced, e.g. trauma has caused damage to the tissue. The term "wound" encompasses injuries including, but not limited to, lacerations, abrasions, avulsions, cuts, burns, velocity wounds (e.g., gunshot wounds), penetration wounds, puncture wounds, contusions, diabetic wounds, hematomas, tearing wounds, and/or crushing injuries. In one aspect, the term "wound" refers to an injury to the skin and subcutaneous tissue initiated in any one of a variety of ways (e.g., pressure sores from extended bed rest, wounds induced by trauma, cuts, ulcers, burns and the like) and with varying characteristics. As used herein, the term "wound healing" refers to a process by which the body of a wounded organism initiates repair of a tissue at the wound site (e.g., skin). The wounds healing process requires, in part, angiogenesis and revascularization of the wounded tissue. Wound healing can be measured by assessing such parameters as contraction, area of the wound, percent closure, percent closure rate, and/or infiltration of blood vessels as known to those of skill in the art. In some embodiments, the particles and compositions described herein can be applied topically to promote wound healing.

As used herein, the term "agonist" refers to any agent that increases the level and/or activity of the target, e.g, of NRP-2. As used herein, the term "agonist" refers to an agent which increases the expression and/or activity of the target by at least 10% or more, e.g. by 10% or more, 50% or more, 100% or more, 200% or more, 500% or more, or 1000% or more. Non-limiting examples of agonists of Sema3F can include Sema3F polypeptides or agonist fragments thereof and nucleic acids encoding a Sema3F polypeptide, e.g. a polypeptide comprising the sequence SEQ ID NO: 1 or SEQ ID NO: 5 or a nucleic acid comprising the sequence of SEQ ID NO: 2 or variants thereof.

As used herein, the term "Sema3F" refers to a member of the class III semaphorins that preferentially binds to NRP-2 as compared to NRP-1. Sequences for Sema3F polypeptides and nucleic acids for a number of species are known in the art, e.g. human Sema3F (NCBI Gene ID: 6405) polypeptide (SEQ ID NO: 1; NCBI Ref Seq: NP_004177) and nucleic acid (SEQ ID NO: 2; NCBI Ref Seq: NM_004186). The level of Sema3F can be assessed in blood, serum and/or plasma and the activity of Sema3F can be measured, e.g. by determining the level of binding of Sema3F to NRP-2, a select NRP-2 signaling response, changes in the activity of, and/or the level of an immune responsiveness parameter wherein increased Sema3F activity is evidenced by a reduced immune response and/or alloimmune response (e.g. cytokine responsiveness, priming, or cell migration following transplantation).

In some embodiments, a Sema3F agonist can be a Sema3F polypeptide or functional fragment thereof or a nucleic acid encoding a Sema3F polypeptide or functional fragment thereof. As used herein, "Sema3F polypeptide" can include the human polypeptide (SEQ ID NO: 1, NCBI Ref Seq: NP_004177) the mature human polypeptide (SEQ ID NO: 5); as well as homologs from other species, including but not limited to bovine, dog, cat chicken, murine, rat, porcine, ovine, turkey, horse, fish, baboon and other primates. The terms also refer to fragments or variants of Sema3F that maintain at least 50% of the activity or effect, e.g. suppression of allograft rejection, of the full length Sema3F of SEQ ID NO: 1 or SEQ ID NO: 5, e.g. as measured in an appropriate animal model. Conservative substitution variants that maintain the activity of wildtype Sema3F will include a conservative substitution as defined herein. The identification of amino acids most likely to be tolerant of conservative substitution while maintaining at least 50% of the activity of the wildtype is guided by, for example, sequence alignment with Sema3F homologs or paralogs from other species. Amino acids that are identical between Sema3F homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, by administering the variant to an appropriate animal model of allograft rejection as described herein. Further discussion of the structure of Sema3F and NRP-2 can be found, e.g. in Klagsbrun M, Eichmann A, *Cytokine Growth Factor Rev,* 2005; which is incorporated by reference herein in its entirety.

In some embodiments, a polypeptide, e.g., a Sema 3F polypeptide, can be a variant of a sequence described herein, e.g. a variant of a Sema3F polypeptide comprising the amino acid sequence of SEQ ID NO: 1 or SEQ ID NO:5. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., can suppress allograft rejection at least 50% as well as wildtype Sema3F. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wildtype Sema3F, e.g. 110%, 125%, 150%, 175%, 200%, 500%, 1000% or more.

One method of identifying amino acid residues which can be substituted is to align, for example, human Sema3F to a Sema3F homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, e.g. SEQ ID NO: 1 or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at blast.ncbi.nlm.nih.gov), with default parameters set.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, a polypeptide, e.g., a Sema 3F polypeptide, administered to a subject can comprise one or more amino acid substitutions or modifications. In some embodiments, the substitutions and/or modifications can prevent or reduce proteolytic degradation and/or prolong half-life of the polypeptide in the subject. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide, e.g., a Sema3F polypeptide, as described herein can comprise at least one peptide bond replacement. A Sema3F polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide, e.g., a Sema 3F polypeptide, as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser(S), Thr (T), Cys (C), Tyr (Y), Asn (N), Gln (Q), Asp (D), Glu (E), Lys (K), Arg (R), and His (H). In some embodiments, a Sema3F polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citrulline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide, e.g. a Sema3F polypeptide, can be modified, e.g. by addition of a moiety to one or more of the amino acids that together comprise the peptide. In some embodiments, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

In some embodiments, the Sema3F polypeptide administered to the subject can be a functional fragment of one of the Sema3F amino acid sequences described herein. As used herein, a "functional fragment" is a fragment or segment of a Sema3F polypeptide which can suppress an immune response (e.g. suppress allograft rejection) in a subject according to the assays described below herein. A functional fragment can comprise conservative substitutions of the sequences disclosed herein.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments, a polypeptide as described herein can be chemically synthesized and mutations can be incorporated as part of the chemical synthesis process.

In some embodiments, a Sema3F polypeptide or functional fragment thereof can be a Sema3F polypeptide that can bind a Sema3F receptor, e.g. NRP-2. In some embodiments, a Sema3F polypeptide or functional fragment thereof can be a Sema3F polypeptide that can bind a domain of NRP-2 selected from the group consisting of the A1; the A2; the B1; and the B2 domain.

As used herein, "NRP-2" or "neuropilin-2" refers to a transmembrane glycoprotein receptor which recognizes class 3 semaphorins and VEGF. NRPs regulate axon growth and angiogensis. NRP2 can be distinguished from NRP1 in that NRP2 has a higher affinity for Sema-3F rather than Sema-3A. The sequences of NRP-2 genes, transcripts, and polypeptides are known in a variety of species, e.g. human NRP-2 mRNA (e.g. SEQ ID NO: 3; NCBI Ref Seq: NM_201266) and polypeptide (e.g. SEQ ID NO: 4; NCBI Ref Seq: NP_957718) sequences (NCBI Gene ID: 8828). NRP-2 comprises the A1 domain (e.g. the amino acids corresponding to positions 28-141 of SEQ ID NO: 4), the A2 domain (e.g. the amino acids corresponding to positions 149-265 of SEQ ID NO: 4), the B1 domain (e.g. the amino acids corresponding to positions 277-427 of SEQ ID NO: 4), and the B2 domain (e.g., the amino acids corresponding to positions 433-592 of SEQ ID NO: 4). Further discussion of NRP-2 structure can be found in the art, e.g., in Appleton et al. The EMBO Journal 2007 26:4901-4912; which is incorporated by reference herein in its entirety. A soluble NRP-2 polypeptide can be a NRP-2 polypeptide corresponding to at least a portion of amino acids 1-862 of SEQ ID NO: 4. In some embodiments, a soluble NRP-2 polypeptide can comprise at least amino acids 1-862 of SEQ ID NO: 4. In some embodiments, a soluble NRP-2 polypeptide can comprise at least 25 contiguous amino acids selected from amino acids 1-862 of SEQ ID NO: 4, e.g., at least 25, at least 50, at least 100, at least 200, at least 250, at least 300, or at least 500 contiguous amino acids selected from amino acids 1-862 of SEQ ID NO: 4. In some embodiments, a soluble NRP-2 polypeptide can comprise at least one NRP-2 domain selected from A1, A2, B1, and/or B2. In one embodiment, soluble NRP-2 polypeptide of use in modulating an immune inflammatory response will bind Sema3F.

The polypeptides of the present invention can be synthesized by using well known methods including recombinant methods and chemical synthesis. Recombinant methods of producing a polypeptide through the introduction of a vector including nucleic acid encoding the polypeptide into a suitable host cell are well known in the art, e.g., as described in Sambrook et al., Molecular Cloning: A Laboratory Manual, 2d Ed, Vols 1 to 8, Cold Spring Harbor, NY (1989); M. W. Pennington and B. M. Dunn, Methods in Molecular Biology: Peptide Synthesis Protocols, Vol 35, Humana Press, Totawa, NJ (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, NY (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, NC (2000); N. L. Benoiton, Chemistry of Peptide Synthesis, CRC Press, Boca Raton, FL (2005); J. Jones, Amino Acid and Peptide Synthesis, $2^{nd}$ Ed, Oxford University Press, Cary, NC (2002); and P. Lloyd-Williams, F. Albericio, and E. Giralt, Chemical Approaches to the synthesis of peptides and proteins, CRC Press, Boca Raton, FL (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the technology described herein relates to a nucleic acid encoding a polypeptide (e.g. a Sema3F polypeptide) as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules include DNA, including genomic DNA or cDNA. Other suitable nucleic acid molecules include RNA, including mRNA. The nucleic acid molecule can be naturally occurring, as in genomic DNA, or it may be synthetic, i.e., prepared based upon human action, or may be a combination of the two. The nucleic acid molecule can also have certain modification(s) such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are linked between the 2'-oxygen and the 4'-carbon atoms with a methylene unit as described in U.S. Pat. No. 6,268,490, wherein both patent and patent application are incorporated herein by reference in their entirety.

In some embodiments, a nucleic acid encoding a Sema3F polypeptide as described herein is comprised by a vector. In some of the aspects described herein, a nucleic acid sequence encoding a Sema3F polypeptide as described herein is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain a nucleic acid encoding a Sema3F polypeptide as described herein in place of non-essential viral genes. The vector and/or particle may be utilized for the purpose of transferring nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments the level of, e.g. Sema3F in the subject is increased by at least 20% over the level of Sema3F in the subject (or in a target tissue or system) prior to treatment, e.g. 20% or more, 30% or more, 40% or more, 50% or more, 100% or more, 150% or more, 200% or more, 250% or more, 300% or more, or 350% or more. In some embodiments the level of Sema3F in the subject is increased by at least 100% over the level of Sema3F in the subject prior to treatment. In some embodiments the level of Sema3F in the subject is increased by at least 200% over the level of Sema3F in the subject prior to treatment.

In some embodiments, a Sema3F agonist can be administered intravenously. In some embodiments, a Sema3F agonist can be administered intramuscularly, subcutaneously, or intradermally. In some embodiments, a Sema3F agonist can be administered locally to a site of inflammation.

In one aspect, described herein is a method of increasing an immune response in a subject in need thereof, the method comprising administering one or more of a Sema3F inhibitor or NRP-2 inhibitor or Plexin A1 inhibitor to the subject. In some embodiments, a subject in need of an increase in an immune response can be a subject with a cancer, e.g. with a tumor. In some embodiments, a subject in need of an increase in an immune response can be a subject with an infection, e.g. a bacterial or viral infection.

As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, Sema3F, e.g. its ability to decrease the level and/or activity of Sema3F, can be determined, e.g. by measuring the level of an expression product of Sema3F and/or the activity of Sema3F. Methods for measuring the level of a given mRNA and/or polypeptide are known to one of skill in the art, e.g. RTPCR can be used to determine the level of RNA and Western blotting with an antibody (e.g. an anti-Sema3F antibody, e.g. Cat No. ab39956; Abcam; Cambridge, MA) can be used to determine the level of a polypeptide. The activity of, e.g. Sema3F can be determined using methods known in the art and described above herein. In some embodiments, the inhibitor can be an inhibitory nucleic acid; an aptamer; an antibody reagent; an antibody; or a small molecule.

Sema3F can be cleaved by furin-like enzymes. Accordingly, in some embodiments, an inhibitor of Sema3F can be a furin-like polypeptide or a nucleic acid encoding a furin-like polypeptide. Conversely, in some embodiments, an agonist of Sema3F can be a furin-like polypeptide inhibitor, e.g. an inhibitory nucleic acid or small molecule inhibitor. Small molecule furin-like polypeptide inhibitors are known in the art and can include, but are not limited to Furin inhibitor I (e.g. Cat No. 344930; EMD Millipore; Billerica MA), Furin inhibitor II (e.g., Cat. No. 344931, EMD Millipore; Billerica MA), and proprotein convertase inhibitor (e.g. Cat. No. 537076, EMD Millipore; Billerica MA). Further discussion of furin inhibitors can be found, e.g. in Becker et al. J Med Chem 2010 53:1067-1075 and Becker et al. JBC 2012 287:21992-22003; each of which is incorporated by reference herein in its entirety.

As used herein, "furin-like polypeptide" refers to proprotein convertases (PCSKs) having a subtilisin-related catalytic domain and a P-domain carboxy-terminal to the subtilisin domain. PCSKs cleave proproteins to yield active mature proteins. A furin-like polypeptide and/or PCSK can be one or more of PCSK1 (e.g. PC1, PC3, PC1/3; NCBI Gene ID: 5122), PCSK2 (e.g. PC2; NCBI Gene ID: 5126), PCSK3 (e.g. Furin, Pace; NCBI Gene ID: 5045), PCSK4 (e.g. PC4; NCBI Gene ID: 54760), PCSK5 (e.g. PC5, PC6, PC5/6; NCBI Gene ID: 5125), PCSK6 (e.g. PACE4; NCBI Gene ID: 5046), PCSK7 (e.g. PC7, PC8; NCBI Gene ID: 9159), PCSK8 (e.g., Site 1 protease, SIP, SK1; NCBI Gene ID: 8720), PCSK9 (e.g. NARC-1; NCBI Gene ID: 255738). Sequences for furin-like polypeptides and corresponding nucleic acids encoding furin-like polypeptides are known in the art and can be readily obtained for a number of species, e.g. from public databases such as NCBI by searching for the provided gene names.

As used herein, "Plexin A1" refers to a transmembrane protein which can bind in combination with NRP-2 to class III semaphorins, e.g. Sema3F. The sequences for Plexin A1 polypeptides and nucleic acids are known for a number of species, e.g., human Plexin A1 (NCBI Gene ID: 5361) polypeptide (SEQ ID NO: 6; NCBI Ref Seq: NP_115618) and nucleic acid (SEQ ID NO: 7; NCBI Ref Seq: NM_032242).

In some embodiments, a Sema3F inhibitor can be a soluble NRP-2 receptor, e.g. a soluble NRP-2 polypeptide. In some embodiments, a soluble fragment of the NRP-2 receptor comprises at least one domain selected from the group consisting of: the A1, the A2, the B1 or the B2 domain. A soluble NRP-2 receptor fragment will generally lack a transmembrane domain.

In some embodiments, an inhibitor of a polypeptide can be an antibody reagent specific for that polypeptide. In some embodiments, a Sema3F inhibitor can be an anti-Sema3F antibody reagent. In some embodiments, a NRP-2 inhibitor can be an anti-NRP-2 antibody reagent. In some embodiments, the NRP-2 inhibitor binds to the extracellular domain of NRP-2.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol. 1996; 26 (3): 629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to Sema3F.

In some embodiments, the methods described herein relate to treating a subject having or diagnosed as having, e.g. an inflammatory condition with an agent (e.g. a Sema3F agonist) as described herein. Subjects having, e.g. an inflammatory condition can be identified by a physician using current methods of diagnosis. Symptoms and/or complications of, e.g. inflammatory conditions which characterize these conditions and aid in diagnosis are well known in the art and include but are not limited to, elevated levels of immune response markers, swelling, and/or heat. A family history of an inflammatory condition or exposure to risk factors for an inflammatory condition can also aid in determining if a subject is likely to have the inflammatory condition or in making a diagnosis of a particular inflammatory condition.

The compositions and methods described herein can be administered to a subject having or diagnosed as having, e.g. an inflammatory condition or being in need of immunosuppression (e.g. having received an allograft or transplant). In some embodiments, the methods described herein comprise administering an effective amount a composition described herein, to a subject in order to alleviate a symptom of, e.g. an inflammatory condition. As used herein, "alleviating a symptom" is ameliorating a condition or symptom associated with the condition. As compared with an equivalent untreated control, such reduction is by at least 10% as measured by any standard technique. A variety of means for administering the compositions described herein to subjects are known to those of skill in the art. Such methods can include, but are not limited to parenteral, intravenous, intramuscular, subcutaneous, transdermal, airway (aerosol), pulmonary, cutaneous, topical, or injection administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount that is sufficient to provide a particular effect when administered to a typical subject. An effective amount as used herein, in various contexts, would also include an amount sufficient to delay the development of a symptom of the disease, alter the course of a disease symptom (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a composition, which achieves a half-maximal inhibition of symptoms) as determined in cell culture, or in an appropriate animal model. Levels in plasma can be measured, for example, by immunoassay or chromatography. The effects of any particular dosage can be monitored by a suitable bioassay, e.g., assay for immune responsiveness, among others. The dosage can be determined by a physician and adjusted, as necessary, to suit observed effects of the treatment.

In some embodiments, the technology described herein relates to a pharmaceutical composition as described herein, and optionally a pharmaceutically acceptable carrier. Pharmaceutically acceptable carriers and diluents include saline, aqueous buffer solutions, solvents and/or dispersion media. Polypeptides, such as Sema3F, will generally be formulated for parenteral administration and can be combined with any carrier suited for parenteral routes of administration. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent as described herein.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration to a patient, including, but not limited to, DUROS®-type dosage forms and dose-dumping.

Suitable vehicles that can be used to provide parenteral dosage forms are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a composition as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. By way of non-limiting example, if a subject is to be treated for inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs-such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like. In some embodiments, the additional anti-inflammatory agent can be a steroid (e.g., a corticosteroid or glucocorticoid); a calcineurin inhibitor (e.g. cyclosporine, tacrolimus, pimecrolimus, or FK506); an mTOR inhibitor (e.g., everolimus, temsirolimus, rapamycin, deforolimus, TOP216, OSI-027, TAFA93, nab-rapamycin, tacrolimus, biolimus, CI-779, ABT-578, AP-23675, BEZ-235, QLT-0447, ABI-009, BC-210, salirasib, AP-23841, AP-23573, KU-0059475, 32-deoxorapamycin, 16-pent-2-ynyloxy-32-deoxorapamycin, 16-pent-2-ynyloxy-32 (S or R)-dihydro-rapamycin, 16-pent-2-ynyloxy-32 (S or R)-dihydro-40-O-(2-hydroxyethyl)-rapamycin, 40-O-(2-hydroxyethyl)-rapamycin, 32-deoxorapamycin; 16-pent-2-ynyloxy-32 (S)-dihydrorapamycin; socalledrapalogs; AP23464; PI-103, PP242, PP30, Torin1; and derivatives or pharmaceutically acceptable salts thereof as well as and compounds described in, e.g. U.S. Patent Publications 2011/0178070; 2011/0021515; 2007/0112005; 2011/0054013; International Patent Publications WO98/02441; WO01/14387; WO99/15530; WO07/135411; WO03/64383; WO96/41807; WO95/16691; WO94/09010; European Patent No. EP1880723; and U.S. Pat. Nos. 8,163,775; 6,329,386; 6,200,985; 6,117,863; 6,015,815; 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; and 5,023,262; which are incorporated by reference herein in their entireties); rapamycin (sirolimus) or an analogue thereof (e.g. everolimus, temsirolimus, ridaforolimus, deforolimus); or an anti-prolferative agent (e.g. mycophenoloate moefitil, azathioprine). In some embodiments, the mTOR inhibitor can be rapamycin or an analogue thereof, e.g. everolimus, temsirolimus, ridaforolimus, or deforolimus. Anti-proliferative agents can include, by way of non-limiting example, alkylating agents (e.g. cyclophosphamide, platinum compounds, and nitrosoureass), antimetabolites (e.g. methotrexate, azathioprine, mercaptopurine, fluorouracil, etc), and cytotoxic antibiotics (e.g., dactinomycin, anthracyclines, mitomycin C, bleomycin, and mithramycin).

In certain embodiments, an effective dose of a composition as described herein can be administered to a patient once. In certain embodiments, an effective dose of a composition can be administered to a patient repeatedly. For systemic administration, subjects can be administered a therapeutic amount of a composition, such as, e.g. 1 µg/kg, 10 µg/kg, 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. a marker of an immune response by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of a composition, according to the methods described herein depend upon, for example, the form of the active ingredient, its potency, and the extent to which symptoms, markers, or indicators of a condition described herein are desired to be reduced, for example the percentage reduction desired for an immune response or the extent to which, for example, an immune response is desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. graft rejection. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing or slowing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of allograft rejection in mice. When using an experimental animal model, efficacy of treatment is evidenced when a statistically significant change in a marker is observed, e.g. the level and/or proliferation of activated T or B cells.

In vitro and animal model assays are provided herein which allow the assessment of a given dose of a composition described herein, e.g. an agonist of Sema3F. By way of non-limiting example, the effects and dose response of a composition can be assessed by treating CD4+ T cells with mitogen (anti-CD3) in the presence and absence of the composition and measuring proliferation and/or the production of cytokines including, but not limited to, IL-2, IL-4 IFN-gamma, IL-17, IL-10, IL-15 and others, where Neuropilin-2 activity is indicated by a lower level of proliferation and/or decreased production of select and/or programs of cytokines.

The efficacy of a given dosage combination can also be assessed in an animal model, e.g. a mouse model of allograft rejection, colitis, or skin inflammation/delayed type hypersensitivity (DTH). For example, C57BL/6 mice can be the recipients of a cardiac or skin allograft from BALB/c mice. Rejection and/or survival can be monitored, e.g. over at least 1-3 weeks. In DTH, skin swelling can be monitored over 1-7 days. As demonstrated herein, treatment of allograft recipients with Sema3F inhibits allograft rejection. Inflammatory response and DTH responses are reduced following treatment with Sema3F. Also, knockout of Neuropilin-2 in recipients of transplants results in accelerated rejection.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g., allograft rejection. A subject can be male or female.

A subject can be one who has been previously diagnosed with or identified as suffering from or having a condition in need of treatment (e.g. a subject undergoing an allograft or having an autoimmune disease) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

Inhibitors of the expression of a given gene can be an inhibitory nucleic acid. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of NRP-2, Sema3F, and/or PlexinA1. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—$N(CH_3)$—O—$CH_2$—[known as a methylene (methylimino) or MMI backbone], —$CH_2$—O—$N(CH_3)$—$CH_2$—, —$CH_2$—$N(CH_3)$—$N(CH_3)$—$CH_2$— and —$N(CH_3)$—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240.

In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_3)_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33 (1): 439-447; Mook, OR. et al., (2007) *Mol Canc Ther* 6 (3): 833-843; Grunweller, A. et al., (2003) *Nucleic Acids Research* 31 (12): 3185-3193). Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA as described herein involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86:6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. See, e.g., Freshney, CULTURE ANIMAL CELLS: MANUAL BASIC TECH. (3rd ed., 1994). As used herein, the term "cancer" refers to an uncontrolled growth of cells that interferes with the normal functioning of the bodily organs and systems. A subject who has a cancer or a tumor is a subject having objectively measurable cancer cells present in the subject's body. Included in this definition are benign and malignant cancers, as well as dormant tumors or micrometastases. Cancers that migrate from their original location and seed vital organs can eventually lead to the death of the subject through the functional deterioration of the affected organs.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10:0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties. Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of suppressing allograft rejection, the method comprising administering a Sema3F agonist to an allograft recipient, whereby immune rejection of the allograft is suppressed.

2. A method of suppressing the immune system in a subject, the method comprising administering a Sema3F agonist to a subject in need thereof.

3. A method of treating an inflammatory condition in a subject in need of thereof, the method comprising administering a Sema3F agonist to the subject.

4. The method of paragraph 3, wherein the inflammatory condition is an autoimmune disease.

5. The method of paragraph 4, wherein the autoimmune disease is selected from the group consisting of:
   Type 1 diabetes; systemic lupus erythematosus; rheumatoid arthritis; psoriasis; inflammatory bowel disease; Crohn's disease; and autoimmune thyroiditis.

6. The method of paragraph 3, wherein the inflammatory condition is a local condition.

7. The method of paragraph 6, wherein the local inflammatory condition is selected from the group consisting of: a rash and an allergic reaction.

8. A method of treating cancer, the method comprising administering a Sema3F agonist to a subject in need of treatment thereof.

9. A method of reducing angiogenesis, the method comprising administering a Sema3F agonist to a subject in need of treatment thereof.

10. The method of any of paragraphs 1-9, wherein the Sema3F agonist is a Sema3F polypeptide or a nucleic acid encoding a Sema3F polypeptide.

11. The method of any of paragraphs 1-10, wherein the Sema3F polypeptide comprises the sequence of SEQ ID NO: 5.

12. The method of paragraph 10, wherein the Sema3F polypeptide can bind a Sema3F receptor.

13. The method of any of paragraphs 1-12, wherein the Sema3F polypeptide can bind a domain of NRP-2 selected from the group consisting of:
   the A1; the A2; the B1; and the B2 domain.

14. The method of any of paragraphs 1-13, wherein the Sema3F agonist is a furin-like inhibitor.

15. The method of any of paragraphs 1-14, wherein the Sema3F agonist is administered intravenously.

16. The method of any of paragraphs 1-14, wherein the Sema3F agonist is administered intramuscularly, subcutaneously, or intradermally.

17. The method of any of paragraphs 1-16, wherein the Sema3F agonist is administered locally to a site of inflammation.

18. The method of any of paragraphs 1-17, further comprising administering an additional anti-inflammatory agent.

19. The method of paragraph 18, wherein the additional anti-inflammatory agent is selected from the group consisting of:
   a steroid; a calcineurin inhibitor; mTOR inhibitor or an analogue thereof; and an anti-proliferative agent.

20. A method of increasing an immune response in a subject in need thereof, the method comprising administering one or more of a Sema3F inhibitor or NRP-2 inhibitor or Plexin A1 inhibitor to the subject.

21. The method of paragraph 20, wherein the Sema3F inhibitor is an anti-Sema3F antibody reagent.

22. The method of paragraph 20, wherein the NRP-2 inhibitor is an anti-NRP-2 antibody reagent.

23. The method of paragraph 20, wherein the Sema3F inhibitor is a soluble NRP-2 receptor.

24. The method of paragraph 23, wherein the Sema3F inhibitor is a soluble fragment of the NRP-2 receptor comprising at least one domain selected from the group consisting of:
the A1, the A2, the B1 or the B2 domain.

25. The method of paragraph 20, wherein the Sema3F inhibitor is a furin-like polypeptide or a nucleic acid encoding a furin-like polypeptide.

26. The use of a Sema3F agonist, to suppress allograft rejection in an allograft recipient.

27. The use of a Sema3F agonist, the use comprising administering a Sema3F agonist to a subject in need of immune system suppression.

28. The use of a Sema3F agonist, for the treatment of an inflammatory condition in a subject in need thereof.

29. The use of paragraph 28, wherein the inflammatory condition is an autoimmune disease.

30. The use of paragraph 29, wherein the autoimmune disease is selected from the group consisting of:
Type 1 diabetes; systemic lupus erythematosus; rheumatoid arthritis; psoriasis; inflammatory bowel disease; Crohn's disease; and autoimmune thyroiditis.

31. The use of paragraph 28, wherein the inflammatory condition is a local condition.

32. The use of paragraph 31, wherein the local inflammatory condition is selected from the group consisting of:
a rash and an allergic reaction.

33. The use of a Sema3F agonist, for the treatment of cancer.

34. The use of a Sema3F agonist, for the suppression of angiogenesis in a subject in need thereof.

35. The use of any of paragraphs 26-34, wherein the Sema3F agonist is a Sema3F polypeptide or a nucleic acid encoding a Sema3F polypeptide.

36. The use of any of paragraphs 26-35, wherein the Sema3F polypeptide comprises the sequence of SEQ ID NO: 5.

37. The use of paragraph 35, wherein the Sema3F polypeptide can bind a Sema3F receptor.

38. The use of any of paragraphs 35-37, wherein the Sema3F polypeptide can bind a domain of NRP-2 selected from the group consisting of:
the A1; the A2; the B1; and the B2 domain.

39. The use of any of paragraphs 26-38, wherein the Sema3F agonist is a furin-like inhibitor.

40. The use of any of paragraphs 26-39, wherein the Sema3F agonist is administered intravenously.

41. The use of any of paragraphs 26-39, wherein the Sema3F agonist is administered intramuscularly, subcutaneously, or intradermally.

42. The use of any of paragraphs 26-41, wherein the Sema3F agonist is administered locally to a site of inflammation.

43. The use of any of paragraphs 26-42, further comprising administering an additional anti-inflammatory agent.

44. The use of paragraph 43, wherein the additional anti-inflammatory agent is selected from the group consisting of:
a steroid; a calcineurin inhibitor; mTOR inhibitor or an analogue thereof; and an anti-proliferative agent.

45. The use of one or more of a Sema3F inhibitor or NRP-2 inhibitor or Plexin A1 inhibitor to promote an immune response in a subject in need thereof.

46. The use of paragraph 45, wherein the Sema3F inhibitor is an anti-Sema3F antibody reagent.

47. The use of paragraph 45, wherein the NRP-2 inhibitor is an anti-NRP-2 antibody reagent.

48. The use of paragraph 45, wherein the Sema3F inhibitor is a soluble NRP-2 receptor.

49. The use of paragraph 46, wherein the Sema3F inhibitor is a soluble fragment of the NRP-2 receptor comprising at least one domain selected from the group consisting of:
the A1, the A2, the B1 or the B2 domain.

50. The use of paragraph 45, wherein the Sema3F inhibitor is a furin-like polypeptide or a nucleic acid encoding a furin-like polypeptide.

EXAMPLES

Example 1: A Novel Immunomodulatory Function For Semaphorin3f And Neuropilin-2 In Allograft Rejection The class 3 family of semaphorins (Sema3A-G) bind to Plexin and Neuropilin family molecules and elicit regulatory signals that result in anti-migration and anti-proliferation. It is demonstrated herein that Sema3F modulates PI-3K-Akt and MAPK signaling via binding to neuropilin-2 (NRP-2), indicating that this ligand-receptor interaction can inhibit T cell activation responses. However, the role of Sema3F and NRP-2 in immunity is previously unexplored.

Described herein is the treatment of C57BL/6 recipients of fully mismatched BALB/c cardiac allografts with Sema3F. Sema3F is demonstrated herein as potent to inhibit rejection; mean graft survival was >22 days (when administered via adenovirus, n=4 mice, P<0.000) and 23.4 days (when administered via i.p. injection, n=16 mice) vs. untreated controls (Mean survival 6.5 days, n=8, P<0.000). Co-treatment of Sema3F treated recipients (i.p. injection model) with a blocking anti-Sema3F antibody (on days 0, 2, 4 and 6) reduced graft survival to control (mean survival 7.5 days, n=4).

By qPCR, FACS and Western blot, it was demonstrated that the Sema3F ligand NRP-2 is expressed on T cell subsets at baseline, and its expression is markedly induced on CD4+ effectors and regulatory cells following 6 hr mitogen-activation (anti-CD3). CD4+ T cells were also found to express Plexin A1-4 family molecules (by qPCR), further indicating that Sema3F may elicit its regulatory signaling via NRP-2 and Plexin. To determine function, we generated NRP-2+/− (Hets) and NRP-2−/− (ko) mice; in vitro, CD4+ T cells derived from these mice were hyperproliferative (~3 fold increase) and produce increased IL-2 and IFNgamma vs. WT cells in response to mitogen (anti-CD3). Hyperactivation was most notable in naïve NRP-2ko CD4+ CD25$^{neg}$ T cells vs. CD4+ CD25+ subsets.

Finally, NRP-2ko mice were used as recipients of fully mismatched BALB/c and minor mismatched B6.C-H-2bm12 donor cardiac transplants. NRP-2ko mice rejected BM12 hearts (mean graft survival 32 days, n=5), vs. WT mice (mean graft survival >54 days, n=11, P<0.00). In contrast, NRP-2ko mice rejected fully mismatched allografts at the same tempo as WT grafts. Additionally, Sema3F can inhibit rejection in NRP-2KO mice, indicating that it can have immunomodulatory effects that are independent of NRP-2. Collectively, these findings for the first time define Sema3F and NRP-2 as novel immunomodulatory proteins.

These findings also indicate that Sema3F-NRP-2 interactions are highly significant for the modulation of allogeneic responses.

Example 2: Novel Effects of Semaphorin3F on the Regulation of Intracellular PI-3K-Akt and MAPK Signaling Class three semaphorins bind neuropilin (NRP) and plexin family molecules and serve as guidance molecules that elicit signals resulting in anti-migration and cytoskeleton collapse. As described herein, semaphorin 3F (SEMA3F) is potent to inhibit allograft rejection in a fully mismatched cardiac allograft model. In addition, it is described herein that NRP2 knockout mice have hyperactive T cells and accelerated rejection, suggesting that Sema3F mediates immunomodulation via interactions with NRP2. Additionally, NRP2 is demonstrated herein to be expressed on both effector and regulatory CD4+ T cells, suggesting that it is a novel protein that targets T cell activation responses. However, the molecular mechanisms of SEMA3F-induced regulation of the immune response are not known.

Two cell lines (U87MG and U343) expressing high levels of NRP2 were used to screen Sema3F-regulated intracellular signaling pathways using phospho-kinase antibody arrays. It was observed that a most potent effect of Sema3F (e.g., 640 ng/ml) is to inhibit the activity of pAkt (T308 and S473) pmTOR and pS6K and pERK, which was confirmed in a time course by Western blot analysis.

SEMA3F binds NRP2 and forms complexes with Plexin A1. Knockdown of either NRP2 or Plexin A1 in U87MG cells using siRNAs inhibited SEMA3F-induced decreases in p-Akt (S473) and p-S6K. These observations indicate that the inhibitory effect of Sema3F is mediated through binding of SEMA3F to NRP2/Plexin A1 at the cell surface.

Using immunoprecipitation, it was also observed that SEMA3F disrupted the association of both raptor and rictor with mTOR. Furthermore, when the cells were treated with rapamycin (10 ng/ml) for 30 mins to target mTORC1, Sema3F is potent to inhibit pAkt (S473)/mTORC2. Also, following transfection with 2DAkt to constitutively activate mTORC1, again it is found that Sema3F inhibits pAkt, confirming that the primary effect of Sema3F-NRP-2 interactions is to target mTORC2/Akt-induced responses.

Figure 21:
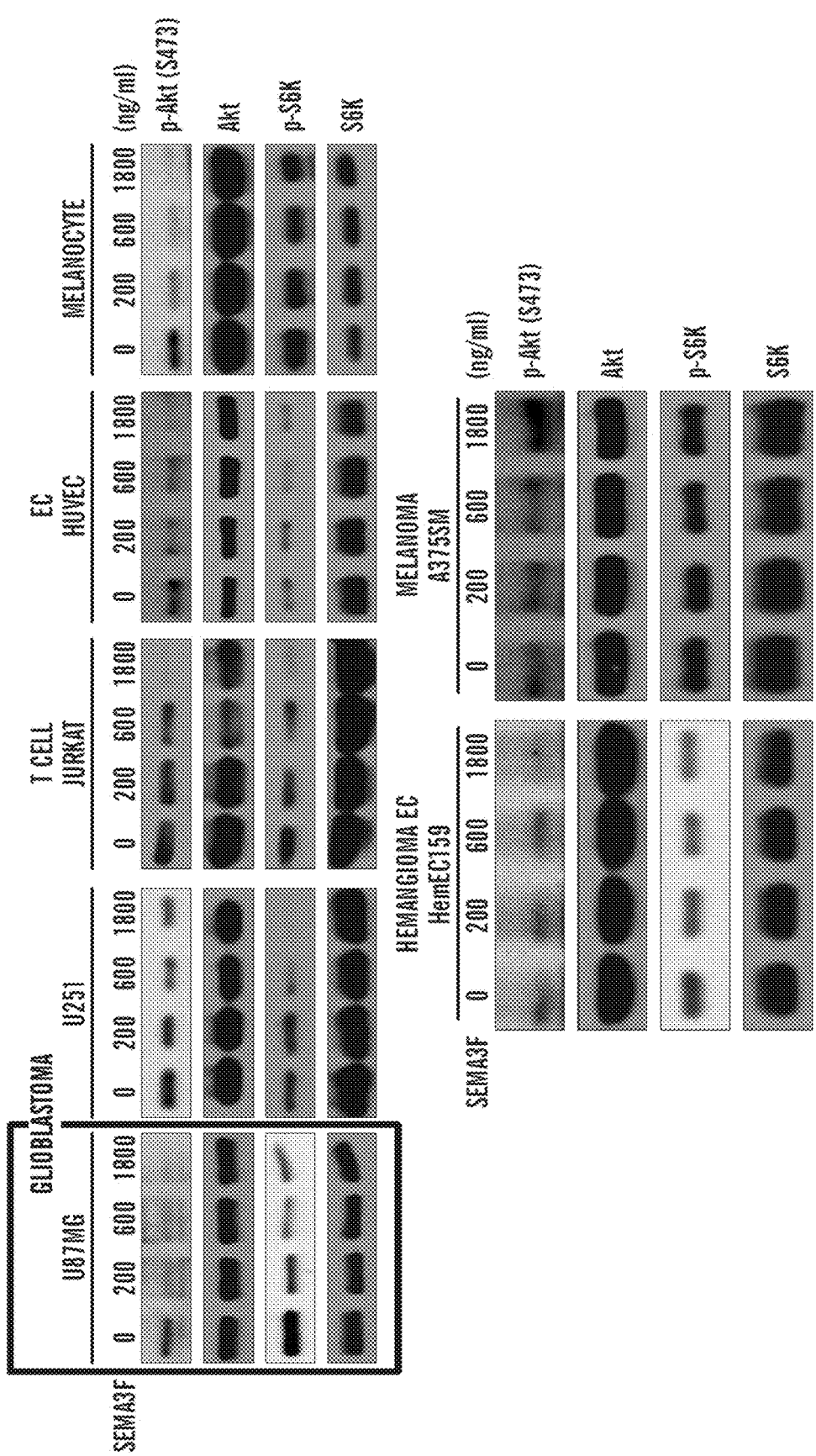
FIG. 21 demonstrates that SEMA3F inhibits Akt/mTOR signaling in multiple cell types. The results of Western blots are depicted, demonstrating the effect of increasing concentrations of Sema3F on Akt/mTOR signaling in the indicated cell types.

Finally, Sema3F-induced responses were evaluated in a human Jurkat T cell line that expresses NRP-2, and it was further confirmed that it elicits a marked regulatory signaling response, including, e.g., the inhibition of pAKT activity. Sema3F inhibits Akt/mTOR signaling in multiple cell types (FIG. 21). Overall, these findings for the first time identify SEMA3F as a novel secreted protein that functions in physiological inflammation resolution via the modulation of intracellular signaling. The findings described herein indicate that Sema3F has broad application as a potent anti-inflammatory therapeutic.

Example 3: Expression and Function of Neuropilin-2, a Semaphorin Receptor, on CD4+ T Cell Subsets The neuropilins NRP-1 and NRP-2 bind semaphorin class 3 family molecules including SEMA3A and SEMA3F respectively, as well as Vascular Endothelial Growth Factor. The binding of SEMA3A to NRP-1 and SEMA3F to NRP-2 elicits inhibitory signals in endothelial cells. NRP-1 is expressed on T cells, and it is prominent on the CD25+ FoxP3+ T regulatory cell subset. In these studies, using qPCR, Western Blot analysis and FACS the expression of NRP-2 on unactivated and mitogen-activated human CD4+ T cells (anti-CD3/anti-CD28, each at 1 mg/ml) was evaluated. Consistently, it was found that NRP-2 expression is minimal on unactivated cells, but is markedly induced (3 to 5 fold, p=0.06, n=3) following activation. Patterns of expression of NRP-2 on murine leukocytes were also profiled and expression on splenocytes as well as enriched CD4+ T cells was found. Although NRP-1 is the dominant receptor on CD25hi Tregs, it was found that NRP-2 is present on both CD4+CD25+ T regulatory and CD4+ CD25-T effector subsets. To define function, CD4+ T cells were sorted from wild type C57/BL6 mice and activation responses assessed following culture with increasing concentrations of anti-CD3 (0.001-1 mg/ml). Taken together, these studies for the first time identify NRP-2 expression on CD4+ T lymphocytes, and indicate that SEMA3F-NRP-2 interactions function in T cell activation responses. These findings set the stage for a new understanding of how class 3 semaphorins may act as novel regulatory cyokines in cell-mediated immunity and allograft rejection.

Figure 7:
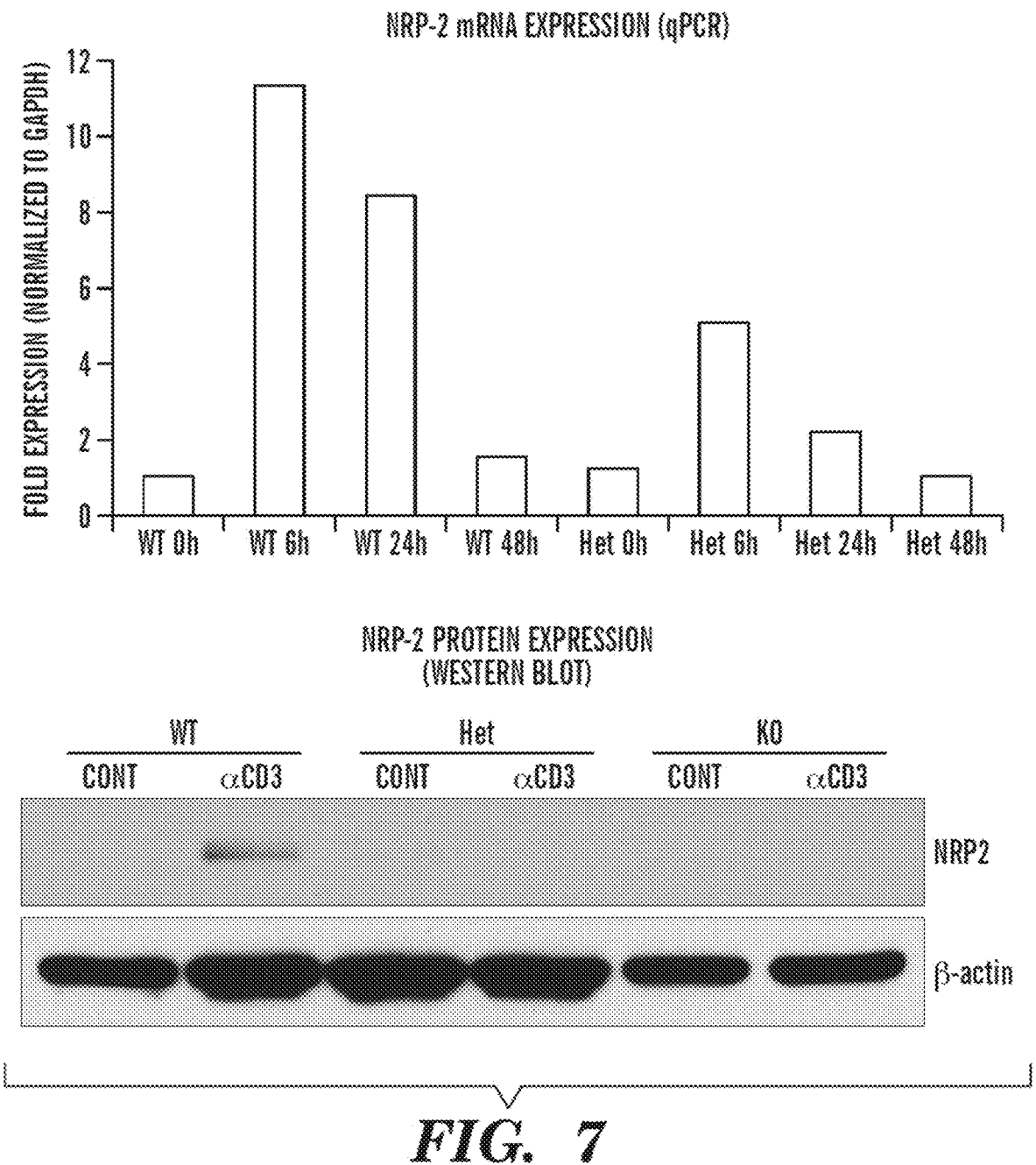
FIG. 7 depicts a graph of the Sema3F receptor Neuropilin-2 (mRNA (top) and protein (bottom)) expression in murine CD4$^+$ T cells. CD4$^+$ T cells were isolated from spleen, were incubated with plate-bound anti-CD3 (1 mcg/ml) for 6 h-48h. RNA was isolated and qPCR was performed. Expression by Western Blot analysis is shown in the bottom panel.
Figure 8:
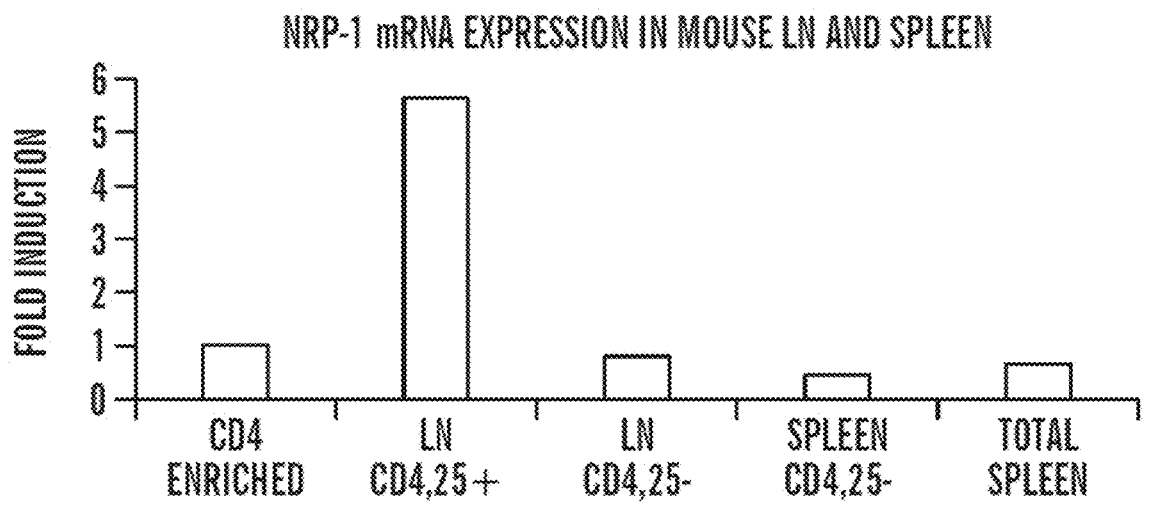
FIG. 8 depicts graphs of Neuropilin-1 and Neuropilin-2 mRNA expression in murine CD4+ T cells. Naïve C57BL6 CD4$^+$ T cells were isolated from lymph nodes and spleen. CD4$^+$ T cell subsets were FACS-sorted into CD25$^{high}$ and CD25$^{low}$ subsets. RNA from CD4$^+$ subsets was isolated and expression levels were determined by qPCR.
Figure 8:
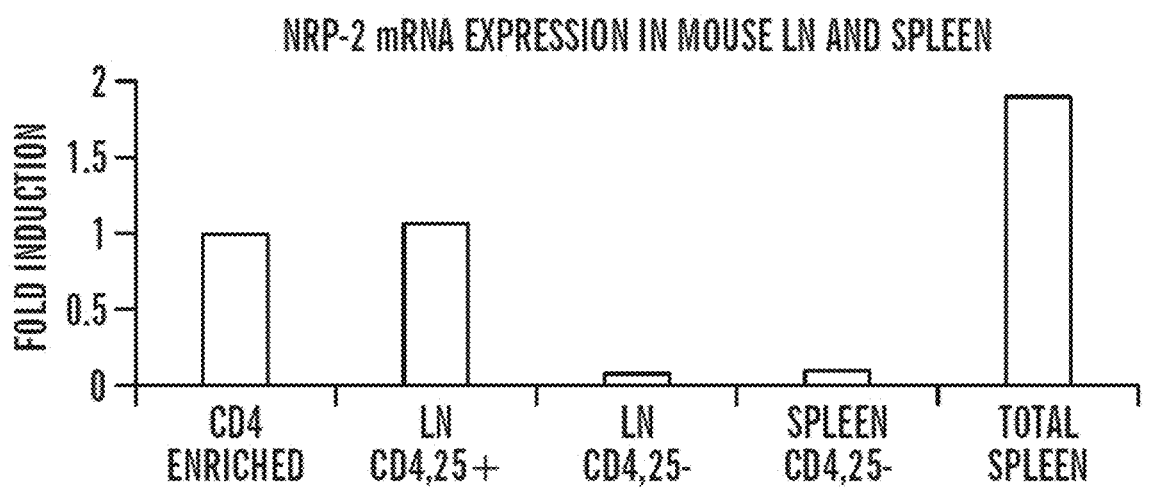

Mitogen-activation increases the expression of both NRP-1 and NRP-2 in human T cells (FIG. 7). NRP-1 is expressed in $CD4^+$ $CD25^{high}$ T cells, whereas NRP-2 is generally expressed in enriched populations of CD4+ T cells (FIG. 8).

Following 7 days of priming with allogeneic or syngeneic splenocytes, recipient spleen cells were stained with CD4 and NRP-2 (monoclonal rabbit anti-mouse NRP-2 from Cell Signalling), followed by a FITC-conjugated donkey anti-rabbit secondary Ab) and subjected to FACS. Quantification following FACS illustrated that allogeneic primed spleen CD4 displayed an increased expression of NRP-2, when compared to syngeneic priming or untreated spleen cells (data not shown).

Taken together these studies identify NRP-2 expression on CD4+ T lymphocytes, and indicate that SEMA3F-NRP-2 interactions function in T cell activation responses.

REFERENCES

Bagri A et al. Clin Cancer Res 2009; 15:1860-1864.

Example 4

It is demonstrated herein that Neuropilin-2 is expressed on human T cells and T cell lines (Jurkat T cells) and the binding of Sema3F results in an activation response. Neuropilin is further demonstrated to be expressed on murine T cells.

The treatment of allograft recipients with Sema3F adenovirus prolongs survival.

The injection i.p of cells overexpressing Semaphorin3F into mice recipients of cardiac transplants is associated with a prolongation of allograft survival, and a delay in the acute rejection response (Rejection in untreated controls day 6-8, rejection following transferred cells day 21-28). Control cells that do not express Sema3F do not delay allograft rejection. Also Transferred cells fail to prolong survival and delay rejection in mice that also received a blockinganti-sema3F antibody (to block the effects of sema3F). In preliminary studies this effect of transferred cells does not occur in mice deficient in NRP-2.

Cells from mice lacking NRP-2 (Heterzygous and NRP-2 KO mice) are hyperproliferative and produce more cytokines than wild type cells following activation with mitogen.

Mice lacking NRP-2 (Heterozygous and NRP-2 KO mice) have an accelerated allograft rejection response.

It is specifically contemplated herein that:
a. Semaphorin 3F or related molecules can be utilized as anti-inflammatory or immunomodulator agents in many inflammatory disease states.
b. Semaphorin 3F and NRP-2 agonists can be utilized in treating and/or preventing allograft rejection. Augmenting these interactions can serve as an immunosuppressant.
c. The use of targeted anti-semaphorin or anti-NRP-2 (A domain molecules) as agents to enhance immune responses.
d. Different mechanisms of antagonism, using NRP-A domain, B domain or A+B domain peptide soluble proteins in immunomodulation Example 5

Figure 2:
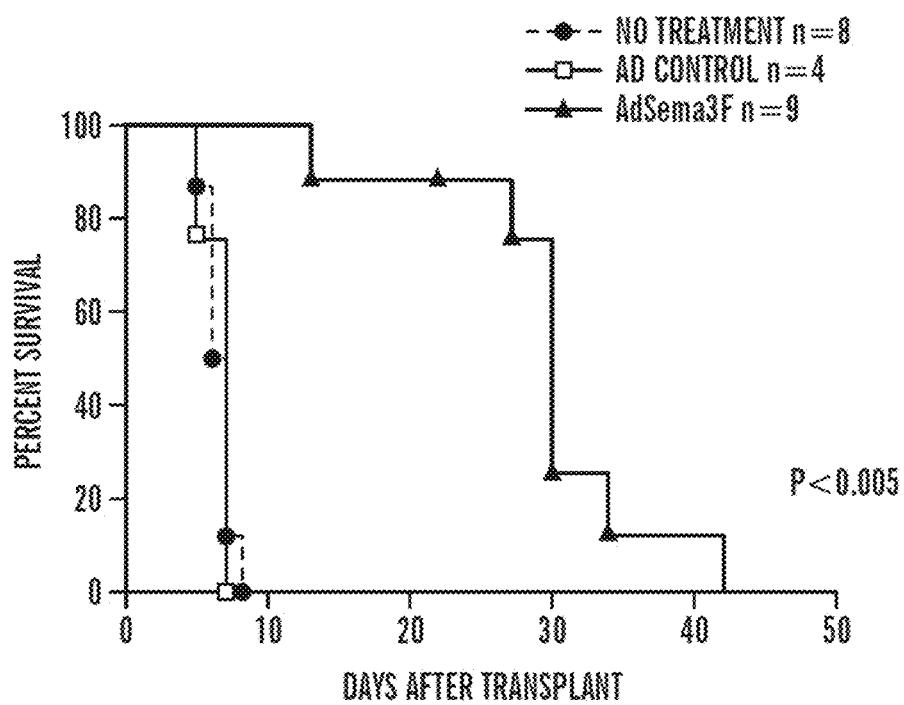
FIG. 2 depicts graft survival curves. Cardiac allografts (Balb/c) were transplanted into fully MHC mismatched recipients (C57BL/6). Unmanipulated recipients reject these allografts within 7-8 days. IV injection of adenovirus encoding Sema3F results in prolonged allograft survival indicating that this agent has potent effects to inhibit the immune response.
Figure 3:
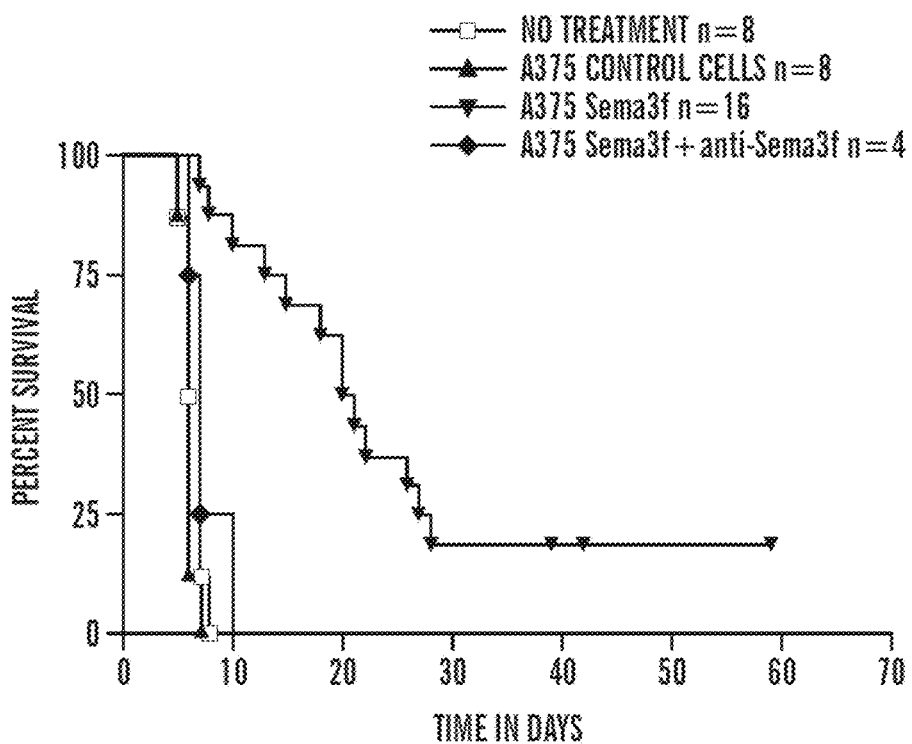
FIG. 3 depicts graft survival curves. Cardiac allografts (Balb/c) were transplanted into fully MHC mismatched recipients (C57BL/6). Unmanipulated recipients reject these allografts within 7-8 days. Injection of Sema3F-expressing cells intraperitoneally to increase systemic levels of Sema3F results in prolonged allograft survival indicating that this agent has potent effects to inhibit the immune response.

Semaphorin 3F Acts as an Immunosuppressant In Vivo to Inhibit Acute Allograft Rejection Balb/C donor hearts were transplanted into C56BL6 mice. Control mice experienced rejection on day 7-8. IV injection of Adenovirus encoding Sema3F into mice following cardiac transplantation prolongs survival up to day 40 (FIG. 2).

Figure 4:
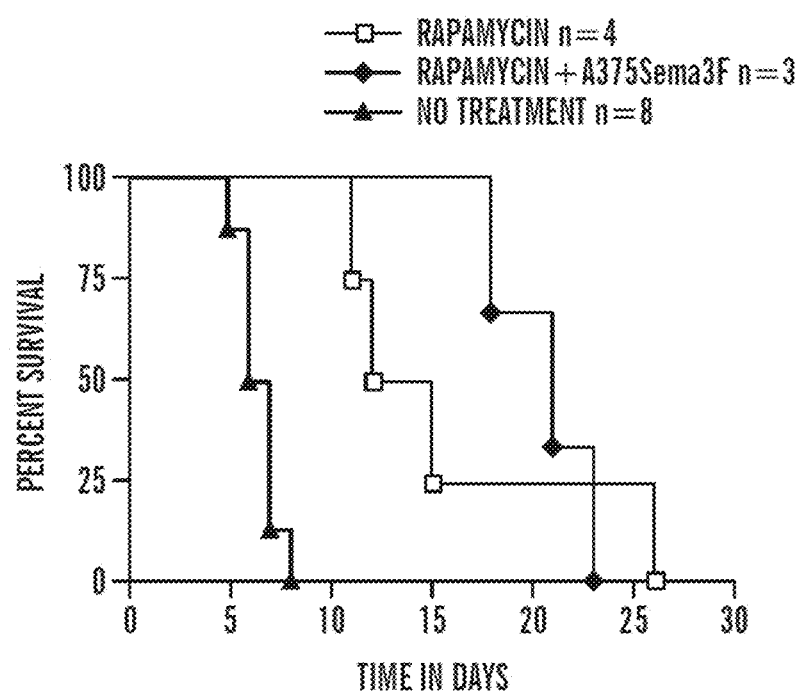
FIG. 4 depicts graft survival curves of C56BL6 recipient mice after transplantation with Balb/C donor hearts. Injection of Sema3F-expressing cells intraperitoneally to increase systemic levels of Sema3F results in prolonged allograft survival Rapamycin (0.2 mg/kg) was administered on day 0 and day2 to initiate a tolerogenic stimulus. Rapamycin failed to further increase survival in combination with Sema3F-expressing cells.

Rapamycin at 0.2 mg/kg was administered on day 0-2 and Sema3F was administered. No additive graft prolongation effect was observed in this limited model (no sig. prolongation of survival) (FIG. 4).

Figure 9:
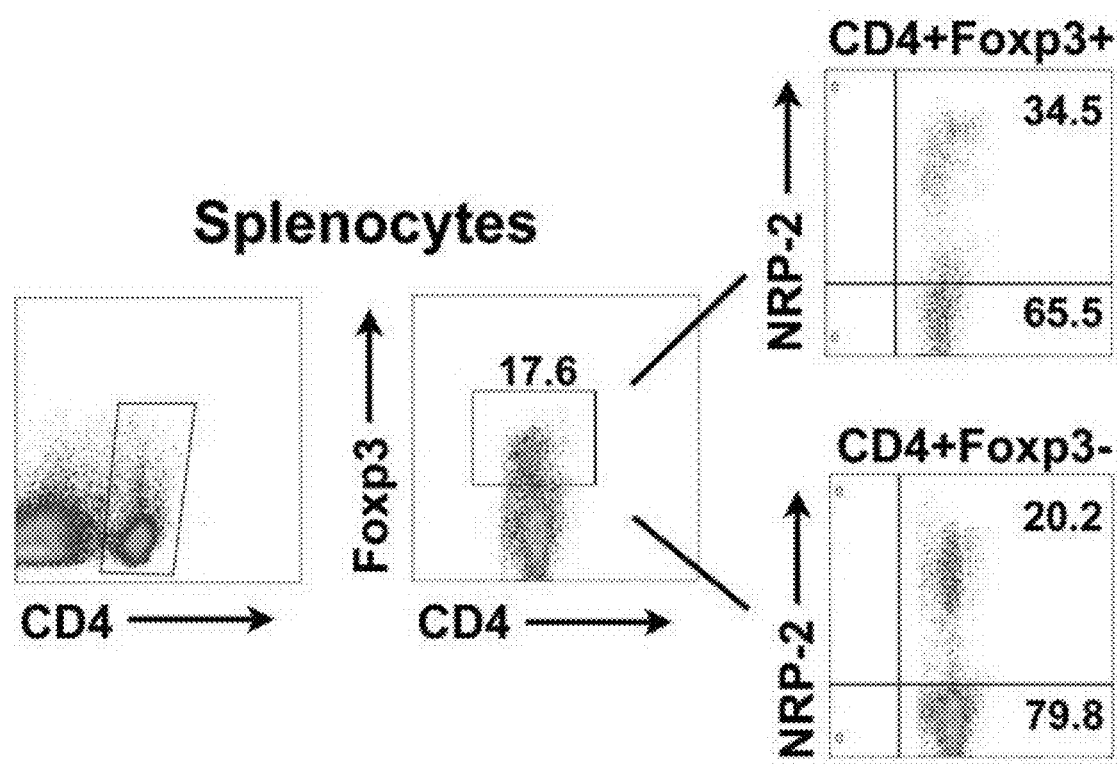
FIG. 9 depicts the results of FACS analysis of CD4$^+$ T cells, both Foxp3$^{pos}$ and Foxp3$^{neg}$ cells. NRP-2 expression was detected using a rabbit anti-NRP-2 Ab (Bioss).

The expression of NRP-2 on T cell subsets was at the mRNA level (FIGS. 7 and 22), protein level by Western Blot (FIGS. 7 and 22) and by FACS (FIG. 9). As illustrated, notable expression of NRP-2 was observed on activated CD4+ T cells, both $Foxp3^{pos}$ and $Foxp3^{neg}$ cells.

CD4+ T cells were sorted into $CD25^{neg}$ T effector subsets from WT, NRP-2+/− (Hets) and NRP-2−/− (KO) mice on a C57BL/6 background. Mitogen-induced proliferation and cytokine production (ELISPOT) was assessed. Markedly enhanced activation responses were observed in whole populations of CD4+ T cells as well as $CD25^{neg}$ subsets derived from NRP-2 Hets and NRP-2 KO mice. This marked hyperactivation response confirms the hypothesis that NRP-2 provides a novel regulatory signal to CD4+ T cells. Sorted populations of CD4+ $CD25^{neg}$ T effector subsets were also cultured with increasing concentrations of mitogen (anti-CD3) in the presence of anti-CD28. CD4+ T cells proliferate maximally in response to costimulatory signals, however, NRP-2 KO cells remain hyperactive and produce significantly more IFNg and IL-2 than CD4+ T cells derived from WT mice. This observation further demonstrates that NRP-2 is functional in CD4+ T cells, and likely elicits regulatory signals.

Chronic Rejection

Figure 5:
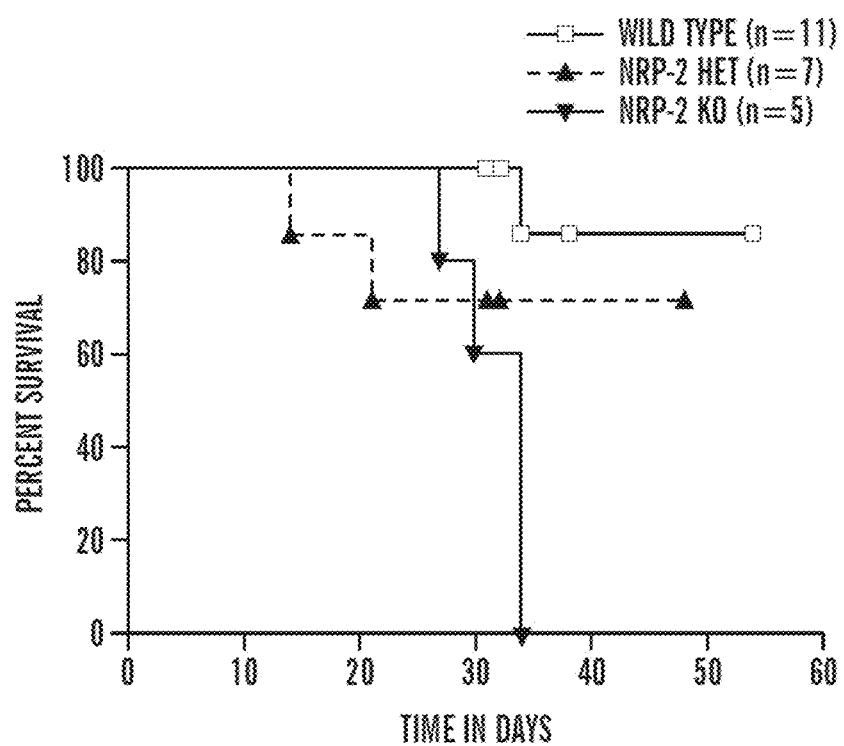
FIG. 5 depicts graft survival curves. Cardiac allografts (B6.C-H2$^{bm12}$ (BM12)) were transplanted into minor MHC mismatched recipients wild type (WT C57BL/6), NRP-2+/− (Het on BL6) or NRP-2−/− (Knockout mice on BL6). While cardiac allografts survive long term in WT recipients, KO mice mount an accelerated rejection response.

Minor MHC mismatched $B6.C-H2^{bm12}$ (BM12) allografts were transplanted into C57BL/6 (wild type/WT), NRP-2+/− (Het on BL6) or NRP-2−/− (KO on BL6) mice. As expected, allografts in WT recipients survive long term but develop chronic rejection after ~30 days post transplantation; marked evidence of disease is present by day 45 (FIG. 5). Long-term survival in this model is reported to be associated with the expansion of T regulatory cells by day 21 post transplantation, that limit the expansion of T effectors (104). Survival is reduced in NRP-2+/− Het recipients and significantly reduced in NRP-2−/− KO recipients (P<0.05). These observations are consistent with the findings that NRP-2 has a regulatory function in CD4+ T cells.

Figure 10A:
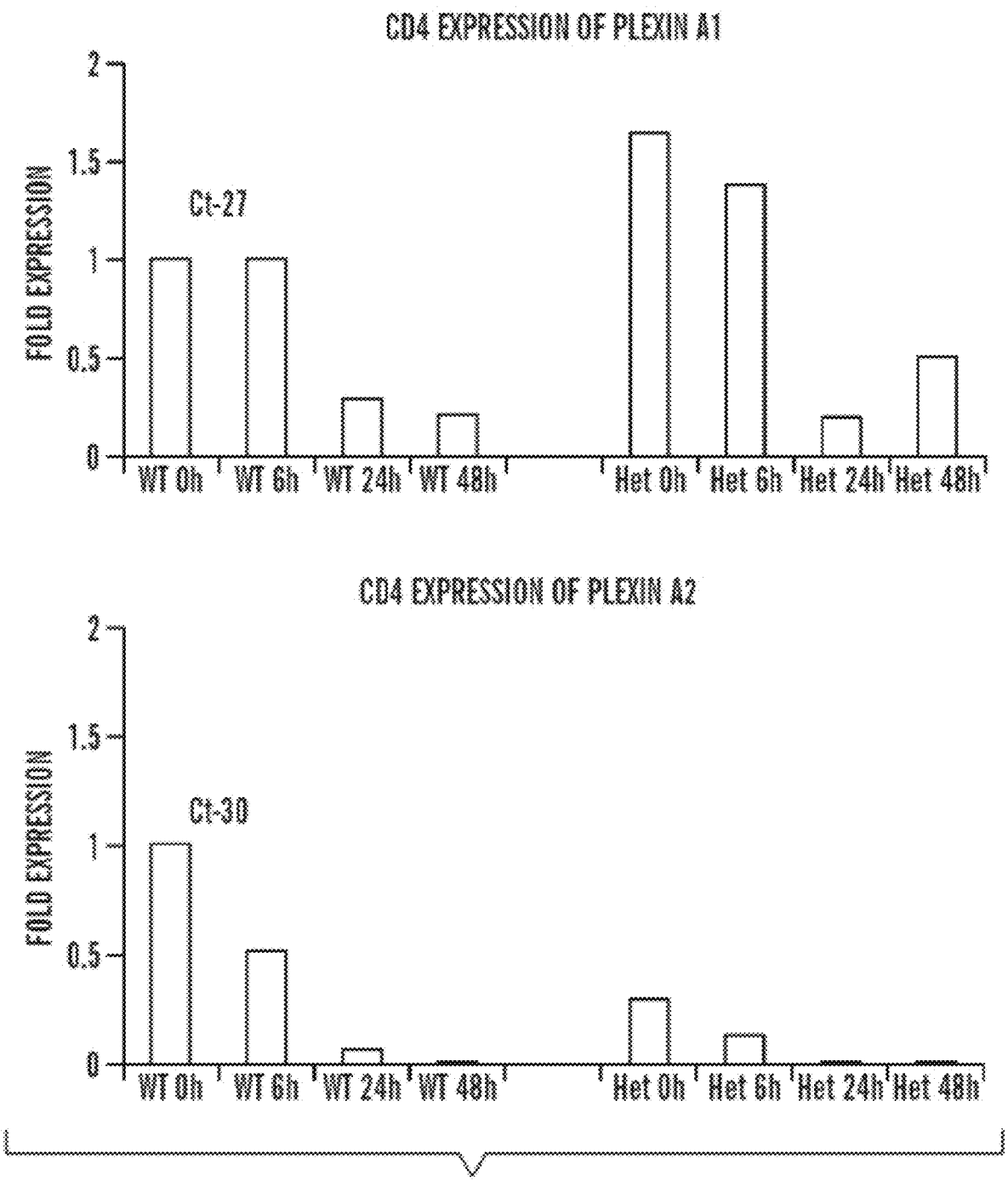
FIGS. 10A-10B depict the expression levels of Plexin family molecules on murine CD4$^+$ T cells either unactivated or following mitogen activation from 6-48 hrs. Expression was examined in wildtype and in NRP-2 heterozygous mice.
Figure 10B:
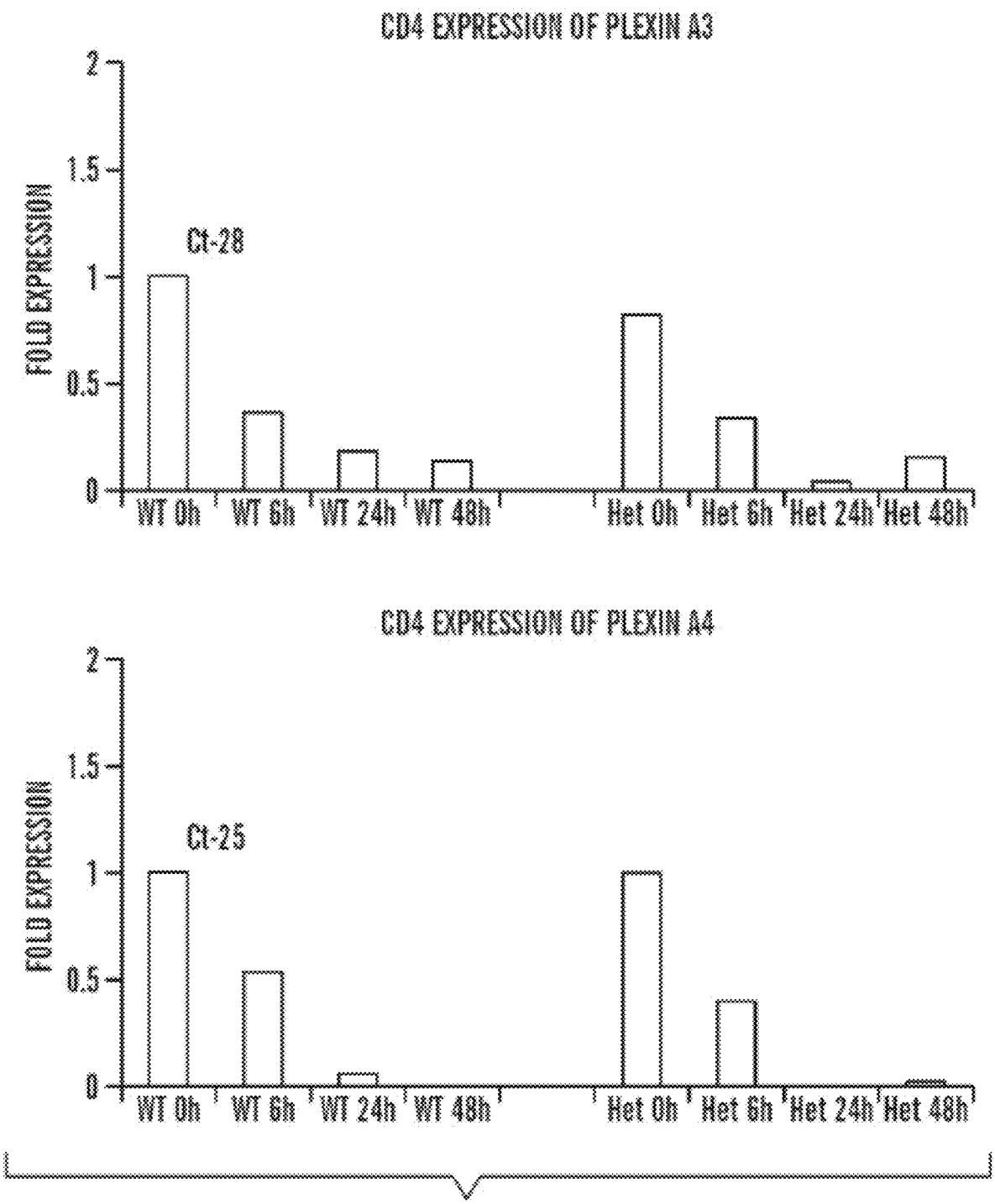
Figure 11:
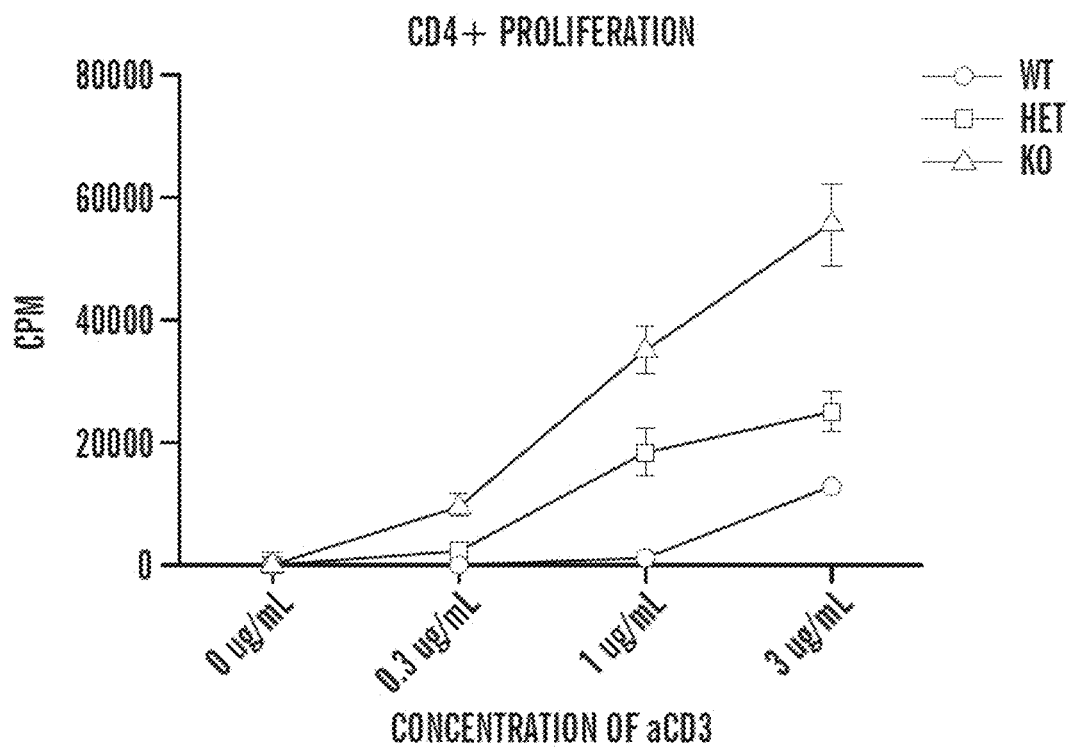
FIG. 11 depicts graphs of CD4+ proliferation. Wildtype, NRP-2 Heterozygous, and NRP-2 knockout CD4+ cells were isolated from spleen and plated at $5\times10^4$ per well and treated with plate-bound anti-CD3 at the indicated concentrations 0-3 mcg/ml. Graphs depict two experiments using different groups of mice (representative of n>5 experiments).
Figure 11:
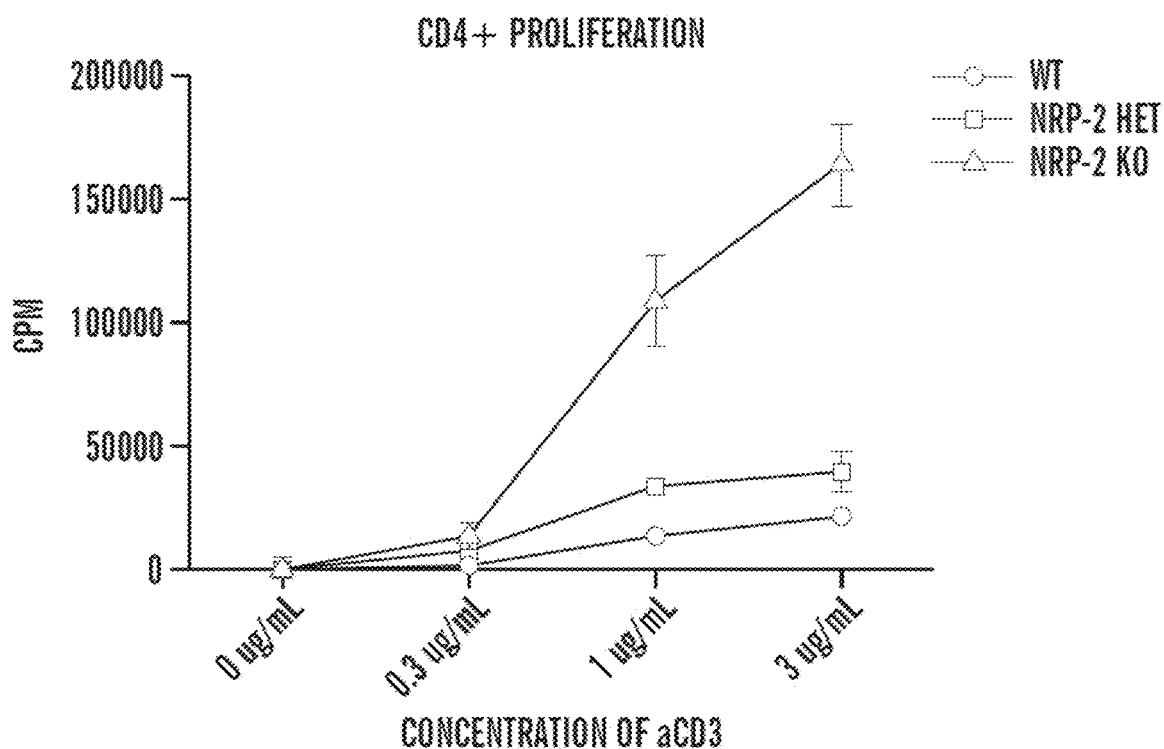
Figure 13:
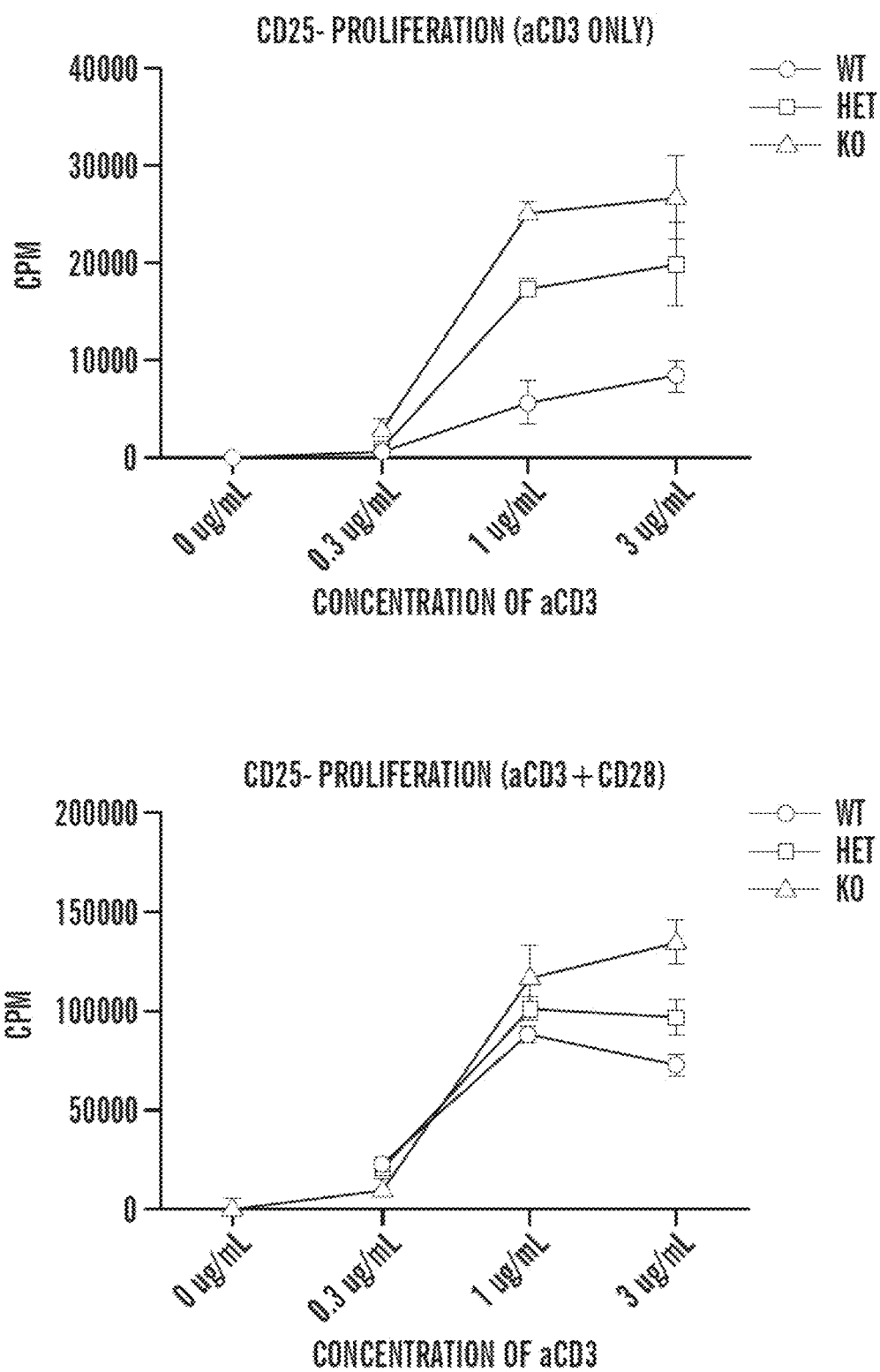
FIG. 13 depicts graphs of mitogen-induced proliferation of CD4+ CD25$^{neg}$ T cells. Splenic CD4+ T cells were sorted into CD25$^{neg}$ T effector subsets from WT, NRP-2+/− (Hets) and NRP-2−/− (KO) mice on a C57BL/6 background and were plated at $5\times10^4$ per well in the presence of platebound anti-CD3 (0, 0.3, 1, or 3 ug/mL as indicated). The upper graph shows cells plated in the absence of anti-CD28 while the bottom graph depicts cells plated in the presence of agonistic anti-CD28 at 1 mcg/ml.

NRP-2 can complex with Plexin family molecules to elicit a regulatory signal, and Plexins family molecules are expressed on CD4+ T cells (FIGS. 10A-10B). Thus, NRP-2 may elicit a regulatory signal in T cells via interactions with Plexins. The effect of NRP-2 on the proliferation of CD4+ cells was examined by plating wild type, NRP-2 het, and NRP-2 knockout cells on plates with plate-bound anti-CD3 at various concentrations. T cell activation as manifest by cytokine production and proliferation was increased in cells with reduced levels of NRP-2 proliferation (FIG. 11). Similar experiments measuring the proliferation of CD4+ CD25− cells were also performed with added costimulation by anti CD28 (1 ug/mL) (FIG. 13). NRP-2 knockouts displayed increased activation but less so in the presence of aCD28. This indicates that NRP-2 can function in the resolution of the T cell activation response vs. the initiation of the activation response.

Figure 12:
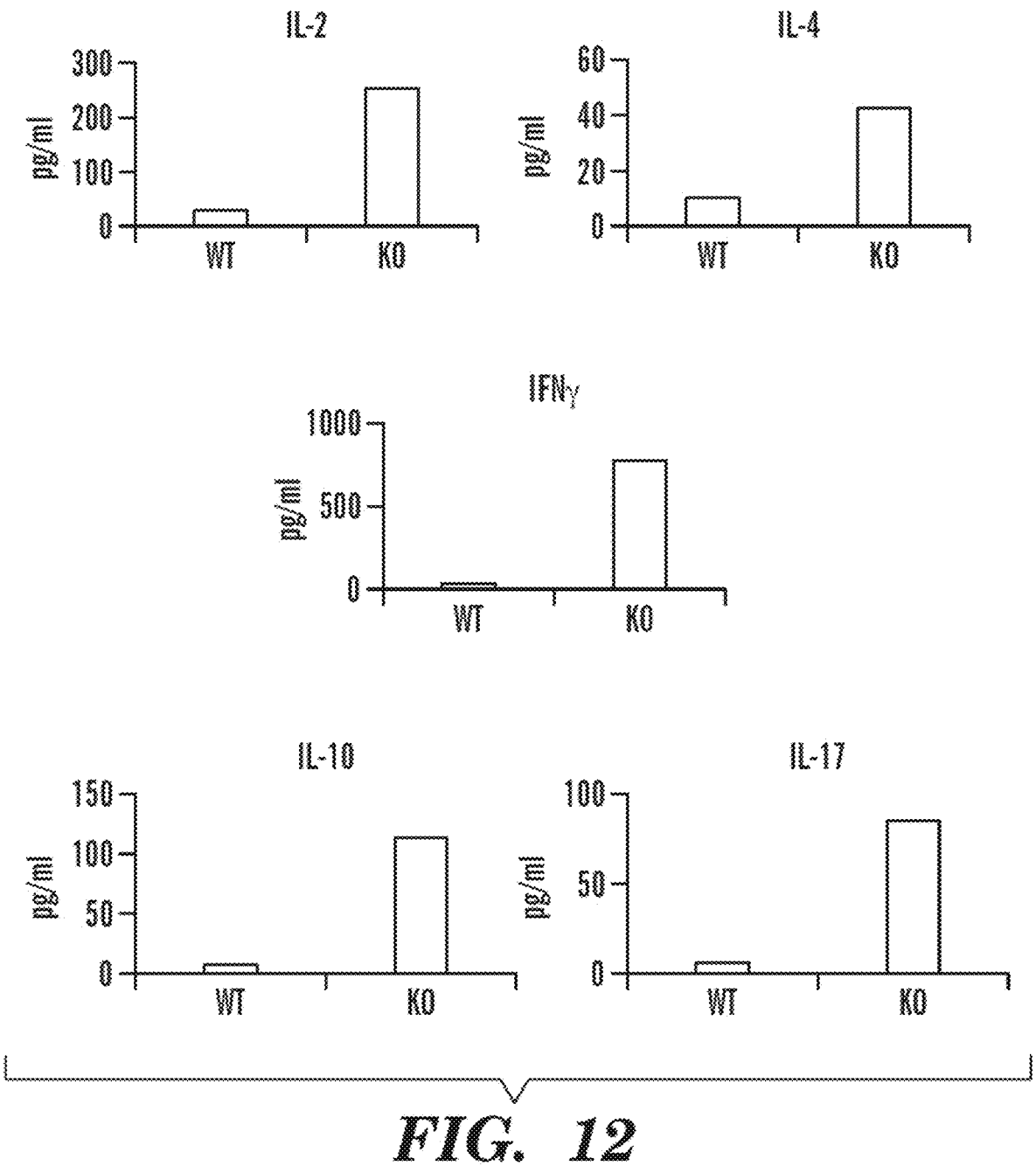
FIG. 12 depicts graphs of cytokine production in Wild type and NRP-2 knockout cells from FIG. 10. CD4+ T cells were mitogen activated (3 mcg/ml, as shown in FIGS. 10A-10B) and levels of the indicated cytokines in the culture supernatants were examined after 72 hours by Luminex assay.
Figure 14:
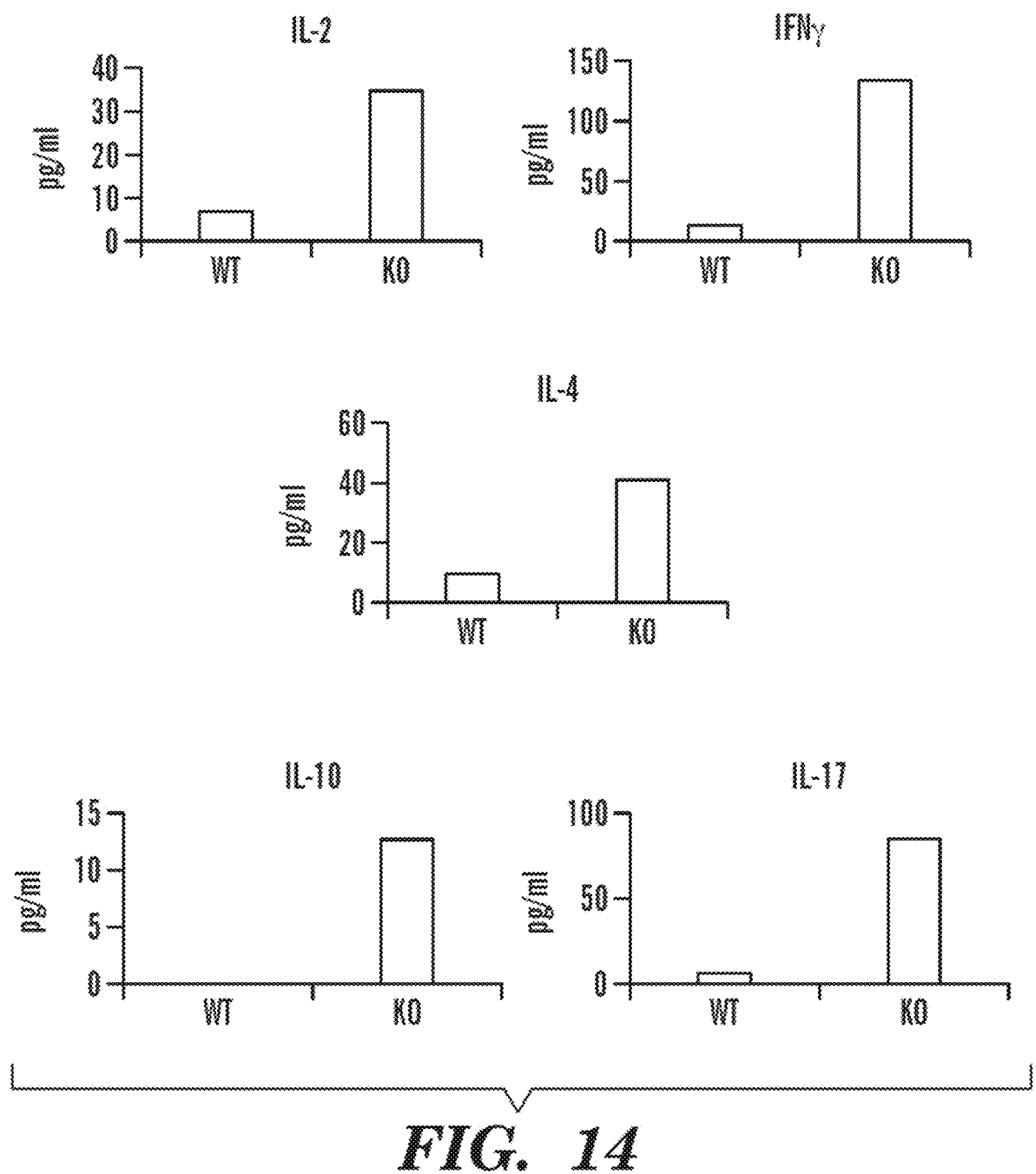
FIG. 14 depicts graphs of cytokine production in NRP-2 knockout CD4+ CD25$^{neg}$ cells from the experiments shown in FIG. 12. NRP-2 knockout cells were mitogen activated with anti-CD3 (3 mcg/ml) and levels of the indicated cytokines in the culture supernatant were examined after 72 hours by Luminex assay.
Figure 15:
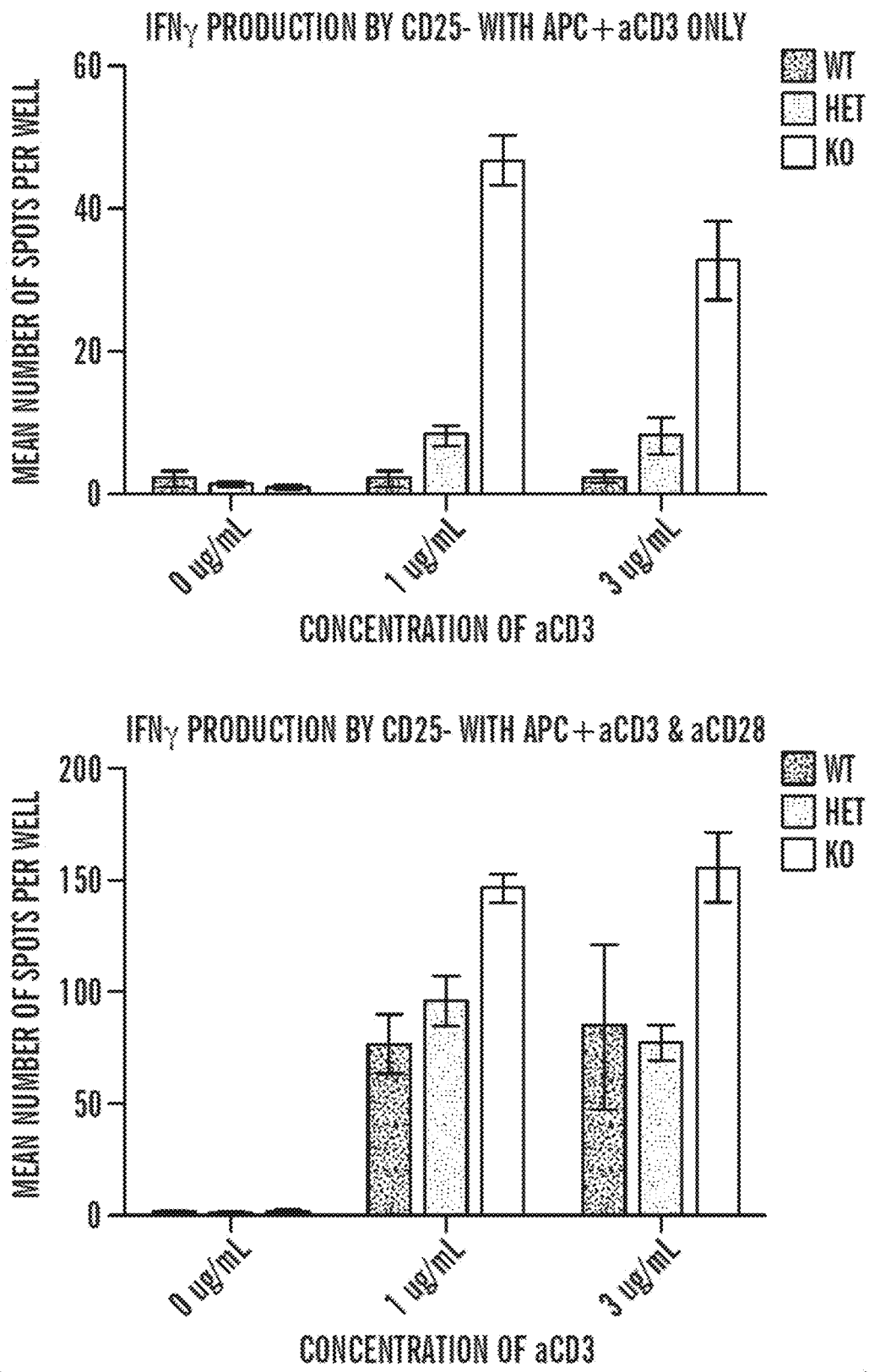
FIG. 15 depicts graphs of IFNγ production in mitogen activated CD25$^{neg}$ CD4+ T cells as measured by the ELISPOT Assay. Wildtype (WT), NRP-2 HET, and NRP-2 KO cells (at $1\times10^5$ per well with APCs at al: 1 ratio) were exposed to anti-CD3 at 0, 1, or 3 mcg/ml with (bottom graph) or without (upper graph) agonistic anti-CD28 at 1 mcg/ml.
Figure 16:
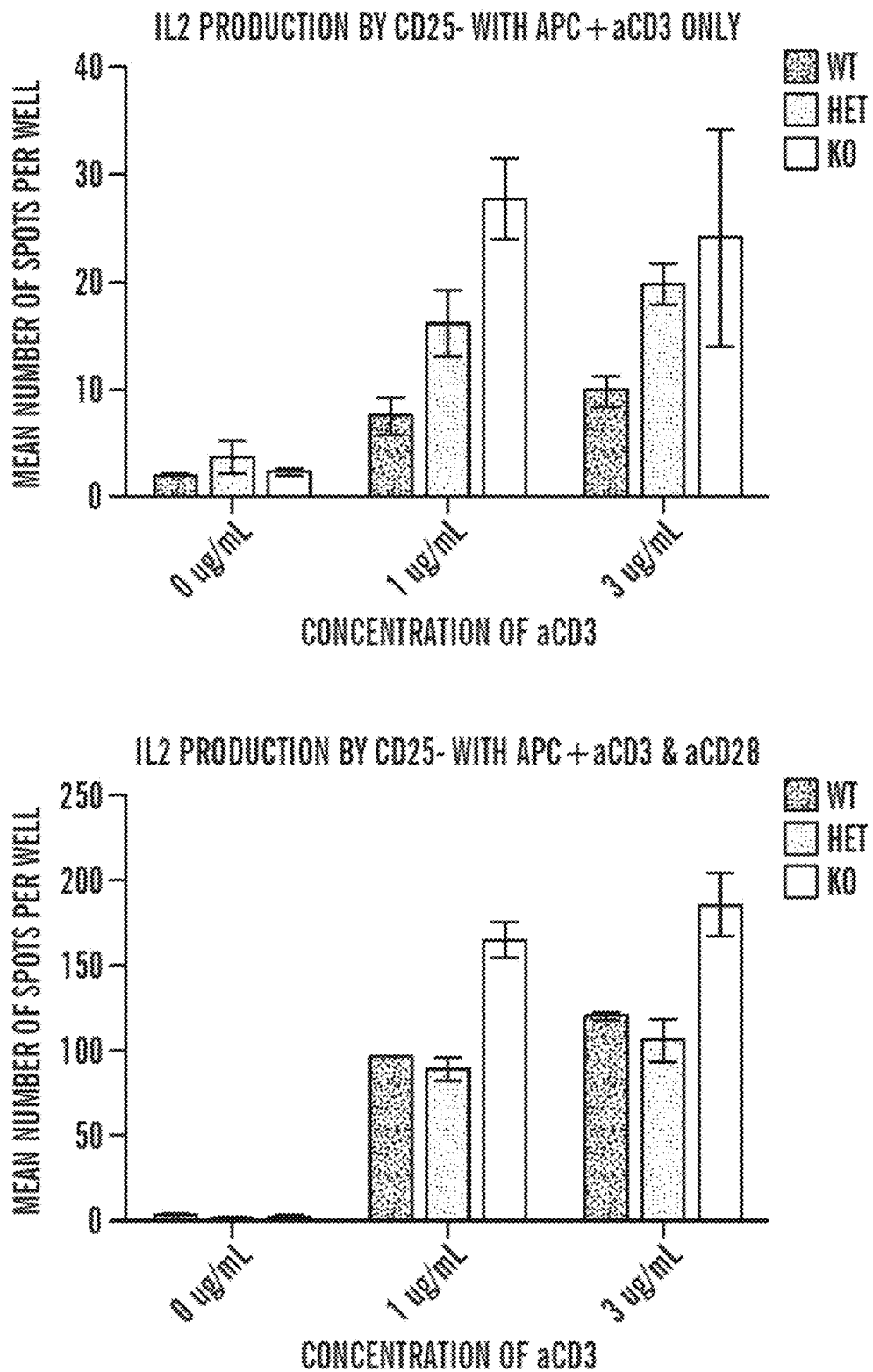
FIG. 16 depicts graphs of IL-2 production in mitogen activated CD25$^{neg}$ CD4+ T cells as measured by the ELISPOT Assay. Wildtype (WT), NRP-2 HET, and NRP-2 KO (at $1\times10^5$ per well with APCs at a 1:1 ratio) were exposed to anti-CD3 at 0, 1, or 3 mcg/ml with (bottom graph) or without (upper graph) agonistic anti-CD28 at 1 ug/mL.
Figure 17:
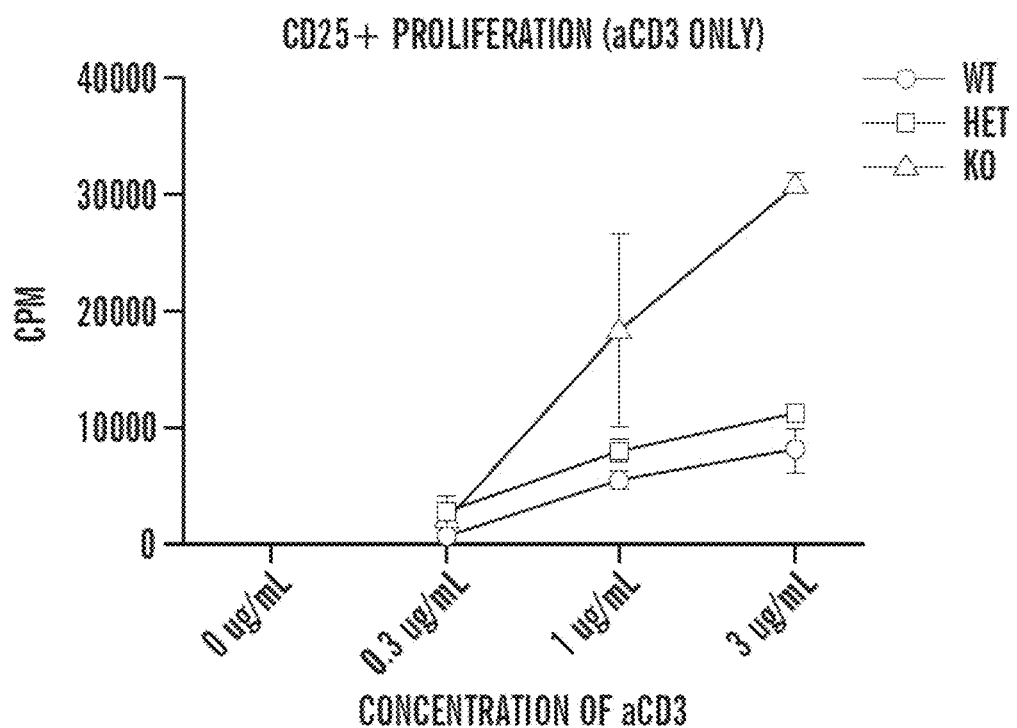
FIG. 17 depicts graphs of proliferation of CD4+ CD25+ T cells. Wildtype (WT), NRP-2 HET, and NRP-2 KO (at $5\times10^4$ per well) were exposed to platebound anti-CD3 at 0, 0.3, 1, or 3 mcg/ml with (bottom graph) or without (upper graph) anti-CD28 at 1 mcg/ml
Figure 17:
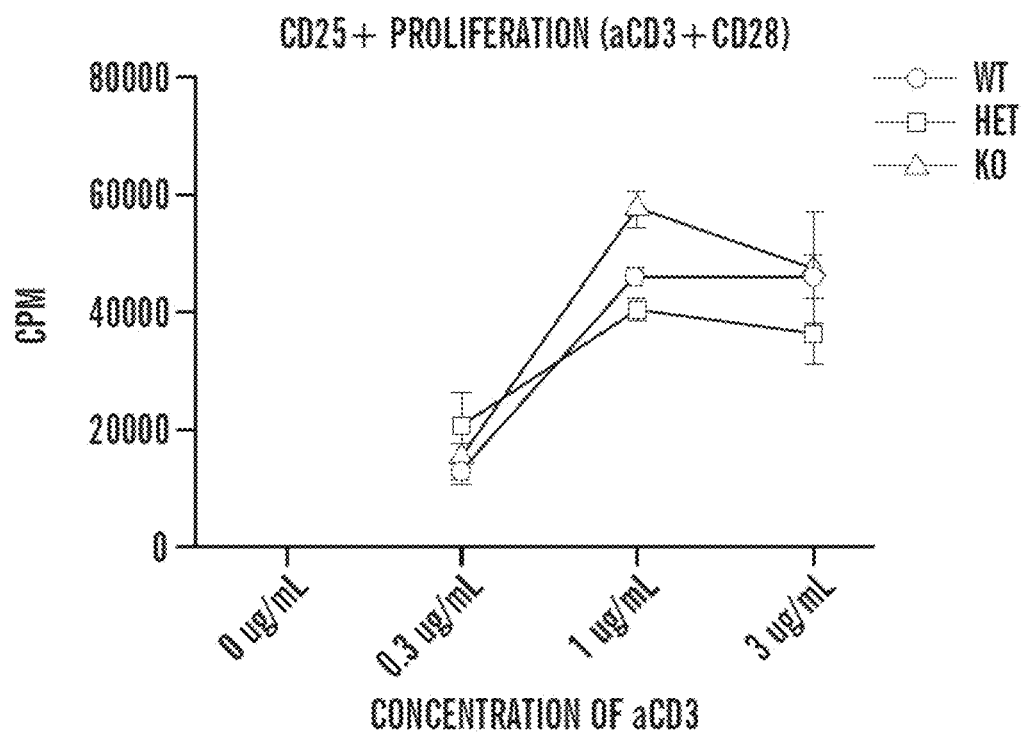
Figure 24:
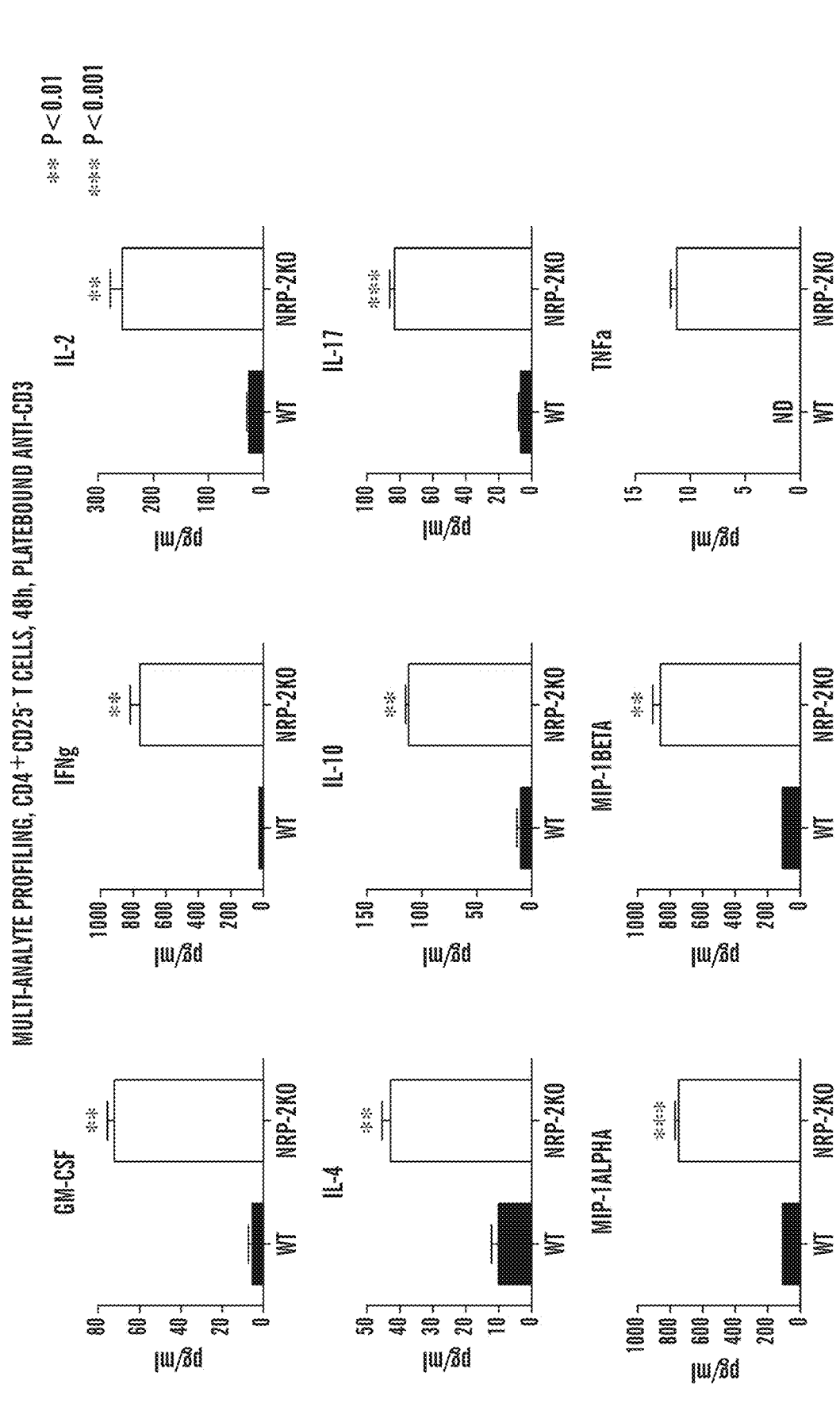
FIG. 24 depicts graphs of cytokine production in NRP-2 knockout CD4+ CD25$^{neg}$ cells. NRP-2 knockout cells were mitogen activated with anti-CD3 and levels of the indicated cytokines in the culture supernatant were examined after 48 hours by Luminex assay. These findings are similar to those shown in FIG. 12.

NRP-2 knockout CD4+ T cells were subjected to mitogen activation and cytokine production in the culture supernatant was examined 72 hours after activation. NRP-2 knockouts displayed increased production of cytokines (FIG. 12). Increased cytokine production was also observed in NRP2 knockout CD4+ CD25− T cells 48 and 72 hours after mitogen activation with anti-CD3 (FIG. 14 and FIG. 24). Production of IFNγ and IL2 was also examined by ELISPOT assay (FIGS. 15 and 16), which similarly demonstrated increased cytokine production in NRP2 knockout cells.

Sema3F Modulates PI-3K/Akt-mTOR Signaling

Figure 18:
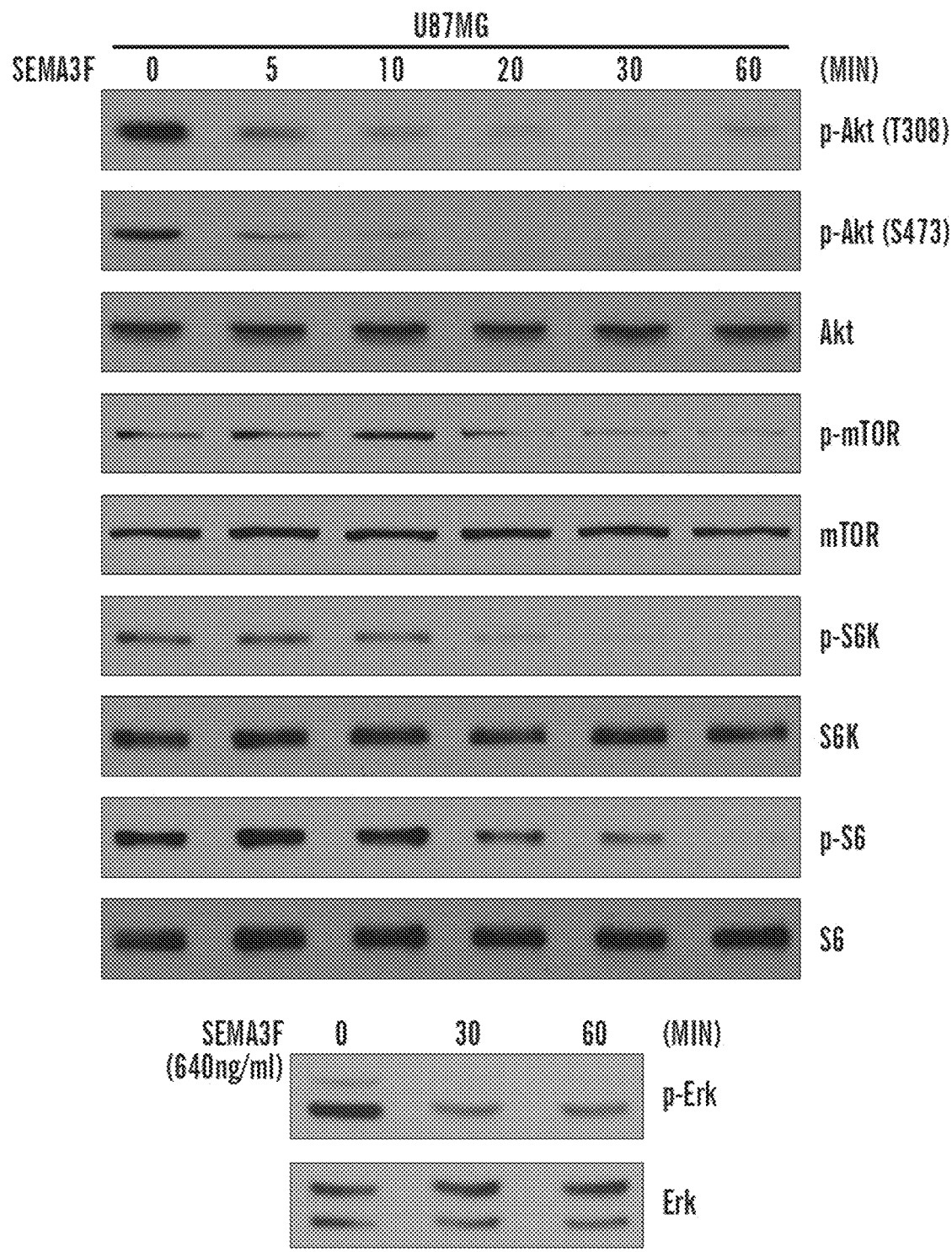
FIG. 18 depicts the time course effect of Sema3F on PI-3K/Akt-mTOR signaling (upper blot) and MAPK signaling (lower blot). U87MG which express NRP-2 were used for this assay. It was observed that cells treated with Sema3F at ~640 ng/ml for up to 60 mins have a reduced level of pAkt (mTORC2) and pS6K (mTORC1) and pERK as measured by Western Blot analysis.
Figure 19:
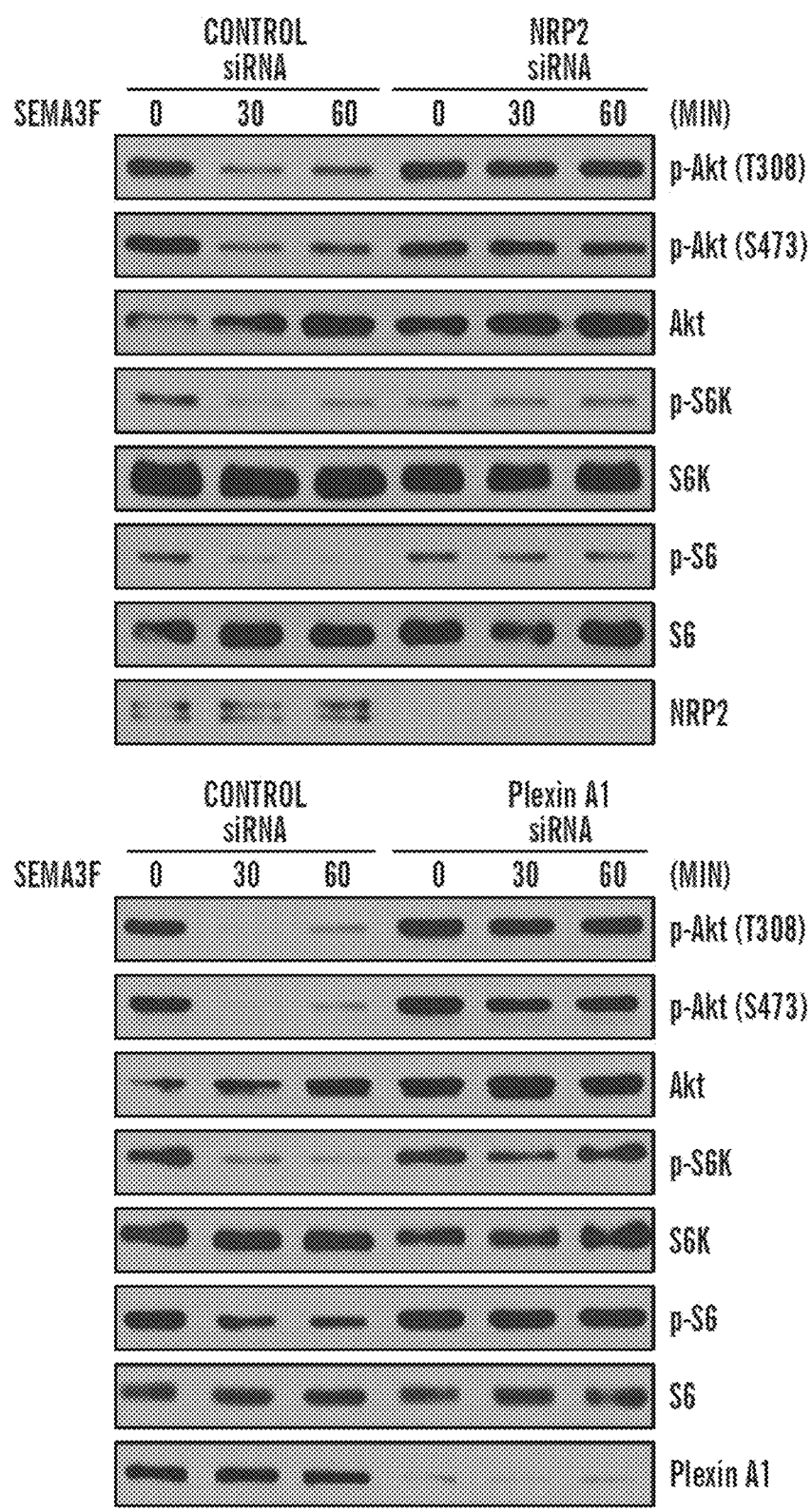
FIG. 19 depicts the effect of NRP-2 (upper) and PlexinA1 (lower) knockdown on Sema3F inhibition of PI-3K/Akt-mTOR signaling. U87MG cells were treated with a control, NRP-2 or PlexinA1 siRNA. Cells were then treated with Sema3F at ~640 ng/ml for up to 60 mins. Knockdown efficiency was evaluated by Western Blot analysis. PI-3K-Akt signaling activity was measured by evaluating the level of pAkt (mTORC2), pmTOR and pS6K (mTORC1) expression.

U87MG cells, known to express high levels of NRP-2, were treated with Sema3F at a level known to stimulate a signaling response (~640 ng/mL). Inhibition of pAkt (mTORC2) and pS6K (mTORC1) dependent activation was observed (FIG. 18). Peak effects of SEMA3F were observed at ~600 ng/ml and this concentration of SEMA3F was used for all signaling analyses. As illustrated in the upper panel of FIG. 18, after 10 min SEMA3F inhibited the expression of pAkt (S473) (densitometry >80%) and by 30 min, there was a most significant reduction in pAkt (S473), pAkt (T308), pmTOR and pS6K. As illustrated in the lower panel of FIG. 18, the expression of pERK1/2 was markedly reduced in cells following SEMA3F treatment, with a peak effect by 30 mins.

siRNA was used to knockdown NRP-2 or PlexinA1 in U87MG cells which were then treated with Sema3F. Time course observation of the effect on the inhibition of pAkt (mTORC2) and pS6K (mTORC1) dependent activation in control siRNA and targeted siRNA cells indicated that knockdown of NRP-2 and PlexinA1 inhibited the effect of Sema3F (FIG. 19). As illustrated in the top panel of FIG. 19, SEMA3F failed to inhibit pAkt and pS6K following NRP2 knockdown. This finding confirms that SEMA3F elicits regulatory signaling via NRP2.

As discussed above, NRP-2 forms a complex with Plexin A1, and it is reported that Plexins elicit the NRP signaling response To test this possibility in the SEMA3F-NRP-2-elicited response, the effect of SEMA3F in U87MG cells following knockdown of Plexin A1 was evaluated. As illustrated in the bottom panel of FIG. 19, SEMA3F was potent to inhibit pAkt and pS6K in control siRNA-transfected cells, but again, it failed to elicit a response in Plexin A1 siRNA transfected cells. These observations indicate that the functional effect of SEMA3F on Akt-induced signals requires interactions between NRP-2 and Plexin A1 at the cell surface.

Figure 20:
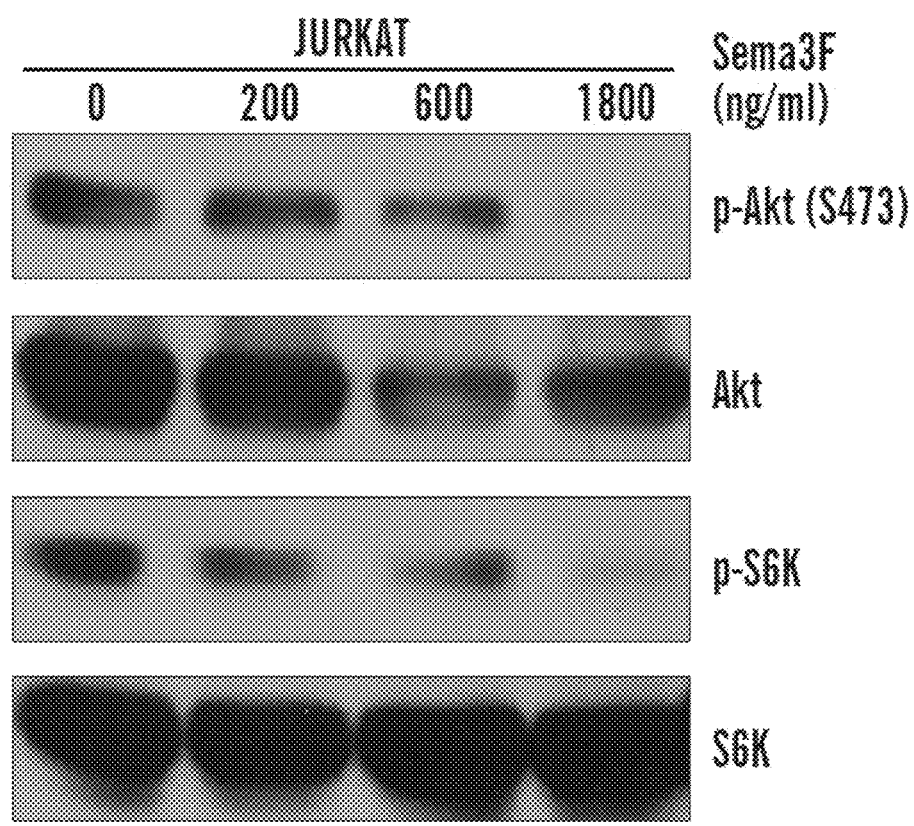
FIG. 20 depicts the results of Western blots of NRP-2-expressing Jurkat T cells treated with increasing concentrations of SEMA3F for 30 min. Expression of pAkt (S473) was evaluated by Western blot.

In addition, as illustrated in FIG. 20 NRP-2-expressing Jurkat T cells were treated with increasing concentrations of SEMA3F for 30 min. and expression of pAkt (S473) was evaluated by Western blot. Expression is reduced following treatment with high concentrations of SEMA3F (>600 ng/ml)

Example 6: Expression of the Regulatory NRP-2 Receptor on Human CD4+ T Cells

Figure 22:
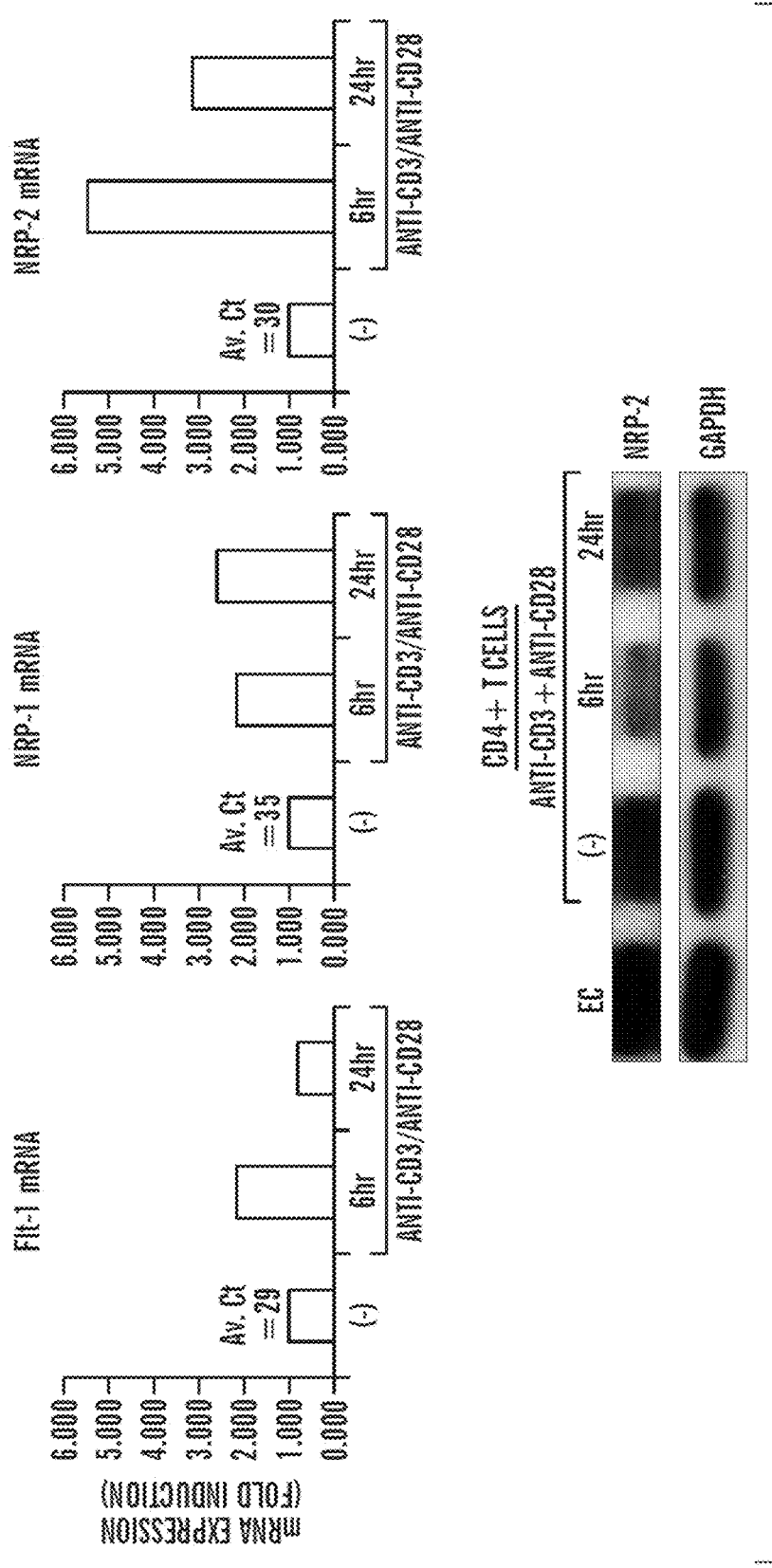
FIG. 22 demonstrates that NRP-1 and NRP-2 are expressed by human T cells. CD4+ T cells were purified from human PBMCs, and the expression of VEGFR1 (Flt-1), NRP-1 and NRP-2 mRNA was evaluated following mitogen-dependent activation (anti-CD3/anti-CD28). Illustrated is representative qPCR data (from n=3 experiments using different T cells) showing comparison between Flt-1, NRP-1 and NRP-2 mRNA expression. The bottom panel depicts Western Blot analysis comparing the expression of NRP-2 protein on unactivated and activated human CD4+ T cells vs. endothelial cells (EC).

NRP-1 and NRP-2 bind VEGF as well as regulatory SEMA3A and SEMA3F respectfully. NRP-1 is expressed by Tregs. CD4+ T cells were purified from human PBMCs, and the expression of VEGFR1 (Flt-1), NRP-1 and NRP-2 mRNA was evaluated following mitogen-dependent activation (anti-CD3/anti-CD28). NRP-2 expression is markedly induced following activation, and is at higher levels than any other receptor (FIG. 22).

Example 7

Figure 6:
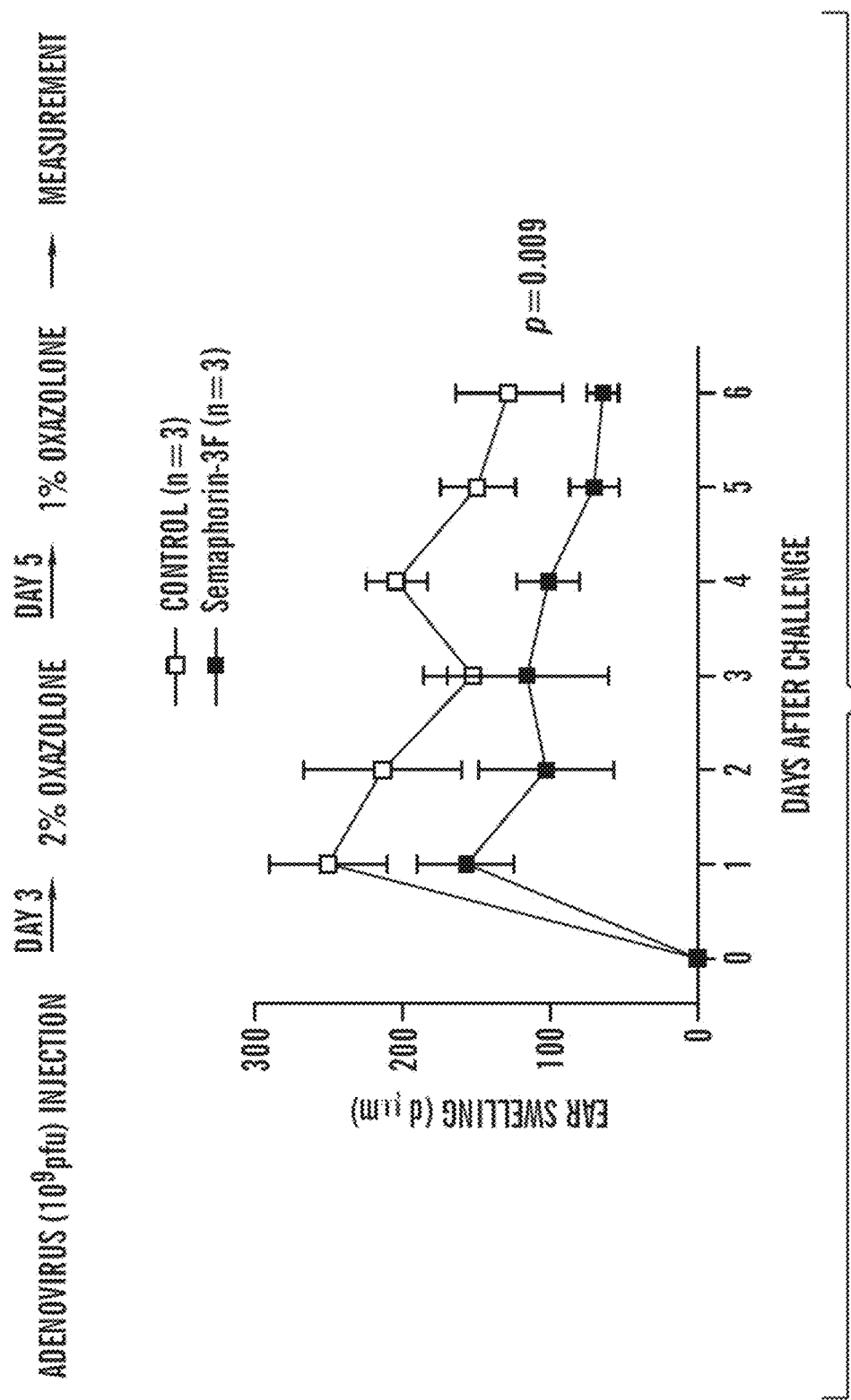
FIG. 6 depicts an oxazalone delayed type hypersensitivity response in mice treated with control adenovirus or adenovirus encoding Sema3F. Three days after a single IV injection of the adenovirus ($10^9$ pfu), mice were primed and challenged in the ear 5 days later with oxazalone using standard techniques. The graph shows the ear swelling in response to oxazalone.

Mice were injected with control adenovirus or adenovirus encoding Sema3F as described above herein. At Day 3 and Day 5 after adenovirus injection, the mice were further treated with oxozalone to induce ear swelling. Mice receiving the Sema3F treatment demonstrated reduced swelling relative to the mice receiving the control treatments (FIG. 6).

Example 8

Figure 23:
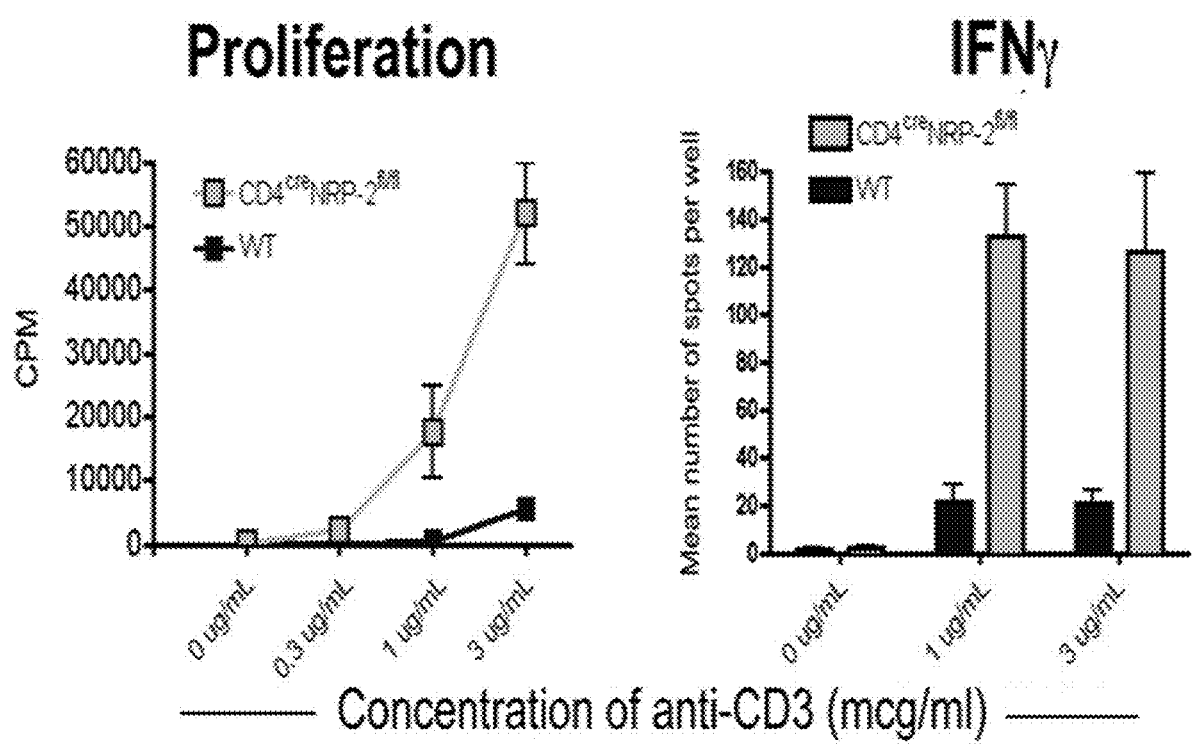
FIG. 23 depicts graphs of data showing that NRP-2 knockdown cells are hyperactive in response to stimulation. The left panel depicts CD4+ T cell proliferation in response to mitogen activation as measured by standard thymidine incorporation assay. The right panel depicts IFNg levels in CD4+ T cells in response to culture with APCs and anti-CD3.

CD4+ T cells were isolated from CD4creNRP-2fl/fl mice and were evaluated for the expression NRP-2 at the mRNA and protein level. Minimal expression was noted. Cells were activated with increasing concentrations of mitogen, and proliferation was determined by standard thymidine incorporation assay. Also, CD4+ T cells were cultured with APCs and increasing concentrations of anti-CD3 and IFNg was assessed by ELISPOT assay. NRP-2 T cell activation responses were compared to wild type mice. Overall, NRP-2 knockdown cells were hyperactive which is consistent with in vivo findings that they mount an exaggerated rejection response (FIG. 23).

Example 9

Figure 25:
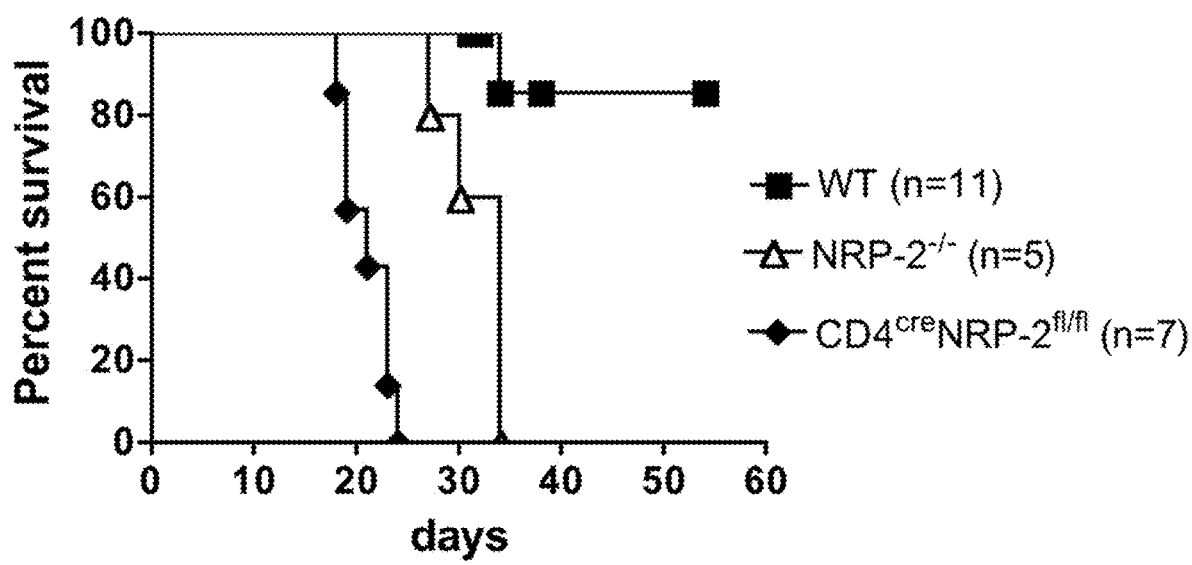
FIG. 25 depicts graft survival curves in a model of chronic allograft rejection. Cardiac Allografts B6.C-H$^{bm12}$ (BM12) were transplanted into minor MHC mismatched recipients, either wild type C57BL/6 (WT), NRP-2 knockout (NRP-2-/-) or select CD4+ T cell NRP-2 Knockout mice (CD4$^{Cre}$-NRP-2$^{fl/fl}$).

FIG. 25 depicts graft survival curves in a model of chronic allograft rejection. Cardiac Allografts B6.C-H$^{bm12}$ (BM12) were transplanted into minor MHC mismatched recipients, either wild type C57BL/6 (WT), NRP-2 knockout (NRP-2-/-) or select CD4+ T cell NRP-2 Knockout mice (CD4$^{Cre}$-NRP-2$^{fl/fl}$). As expected, cardiac allografts survive long term in WT mice; however, knockout mice mount an accelerated rejection response.

Example 10: Expression of NRP-2 on Human CD4+ T Cells

Figures 26A, 26B, 26C:
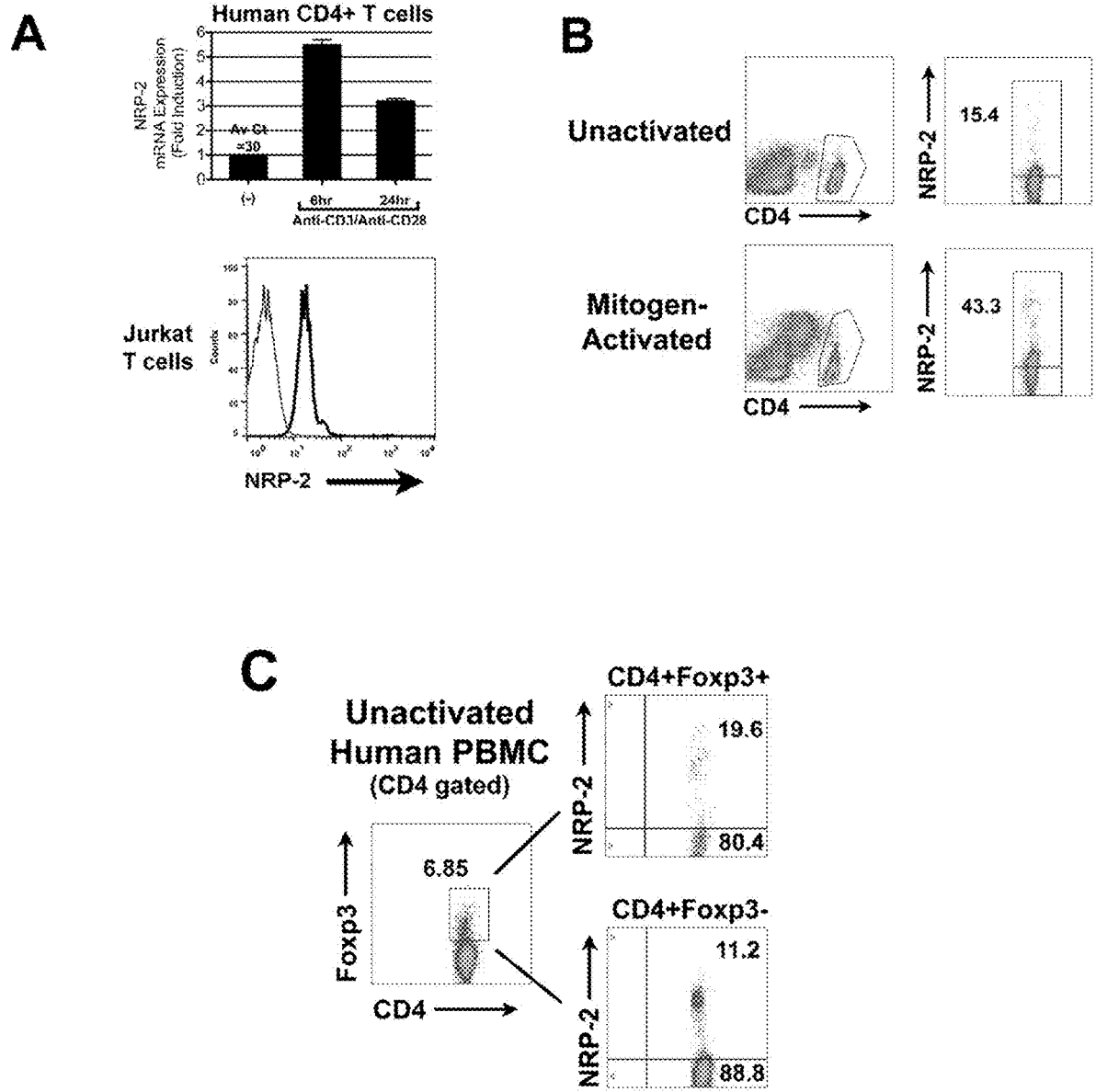
FIGS. 26A-26C show data demonstrating the expression of NRP-2 on Human CD4+ T cells.

Human CD4+ T cells were isolated by negative selection from Human Peripheral Blood. Expression of NRP-2 was evaluated by qPCR on unactivated and mitogen (Anti-CD3/CD28) activated cells (FIG. 26A). Note that mRNA expression increases upon activation. Expression was also evaluated on a human Jurkat T cell line. By FACS, Jurkats express high levels of NRP-2.

Human peripheral blood cells were isolated by standard Ficoll separation and were used unactivated or following mitogen-activation. NRP-2 expression was evaluated by FACS on the CD4+ subset (FIG. 26B). Protein expression increases following activation.

Peripheral blood cells were stained with anti-CD4, anti-FoxP3 and NRP-2 (FIG. 26C). Illustrated is expression as evaluated by FACS showing that both FoxP3+ human CD4+ T regulatory cells and non-FoxP3/T effector cells express NRP-2.

Example 11: Expression of NRP-2 on Murine CD4+ T Cells

Figure 27C:
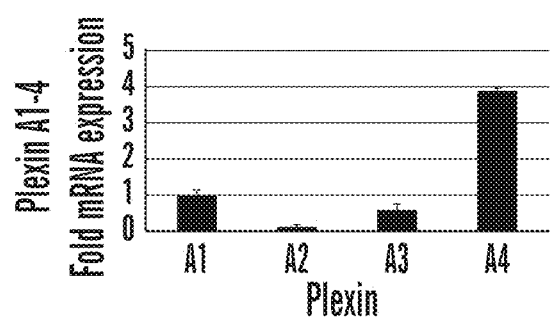

FIG. 27A depicts FACS analysis of NRP-2 on CD4+ T cells within murine spleen and lymph node. Note that distinct populations of CD4+ T cells express NRP-2. CD4+ T cells were isolated by negative selection from murine spleen. Expression of NRP-2 was evaluated by qPCR on unactivated and mitogen (Anti-CD3/CD28) activated cells (FIG. 27B). Note that expression increases upon activation. Plexin A family molecules were also evaluated on isolated CD4+ T cells. Expression of Plexin A1 and A4 appear to be highest on this subset (FIG. 27C). CD4+ T cells were isolated by negative selection from murine spleen and the expression of NRP-2 was evaluated on Foxp3+ and Foxp3 negative subsets (FIG. 27D). NRP-2 is expressed on both subsets of unactivated CD4+ cells. Isolated Splenic CD4+ T cells were mitogen activated (anti-CD3-1 mcg/ml) and expression of NRP-2 was evaluated by Western Blot analysis (FIG. 27E). Again NRP-2 is found to be increased in expression upon activation. CD4+ T cells were driven to differentiation into induced Treg cells in standard culture medium (mitogen+ TGFb+anti-IL-4+anti-IFNg+retinoic acid) and expression of NRP-1/2 was evaluated by Western Blot (FIG. 27F). On this cell type NRP-2 is co-expressed with NRP-1

Example 12: Regulation of Mtor Signaling by Semaphorin 3F Neuropilin 2 Interactions In Vitro and In Vivo Semaphorin 3F (SEMA3F) provides neuronal guidance cues via its ability to bind neuropilin 2 (NRP2) and Plexin A family molecules. Described herein is the analysis of SEMA3F-NRP2 signaling responses in human endothelial, T cell and tumor cells using phosphokinase arrays, immunoprecipitation and Western blot analyses. Consistently, SEMA3F inhibits PI-3K and Akt activity, and responses are associated with the disruption of mTOR/rictor assembly and mTORdependent activation of the RhoA GTPase. It is also described herein that the expression of vascular endothelial growth factor, as well as mTOR-inducible cellular activation responses and cytoskeleton stability are inhibited by SEMA3F-NRP2 interactions in vitro. In vivo, local and systemic overproduction of SEMA3F reduces tumor growth in NRP2-expressing xenografts. Taken together, SEMA3F regulates mTOR signaling in diverse human cell types, indicating that its biology has broad implications in chronic disease.

Introduction

Neuronal networking is regulated by the response of axonal growth cones to environmental cues, both positive and negative. For instance, cues elicited by netrin-1 are chemoattractive, whereas those dominated by semaphorin 3F (SEMA3F) are chemorepulsive. These processes, known collectively as axon guidance, play an important role in the development of the central nervous system (1, 2). SEMA3F is a member of the class 3 semaphorins (SEMA3A-G), whose receptors are neuropilin 1 (NRP1), neuropilin 2

(NRP2) and Plexins (3, 4). Semaphorins are involved in vascular and tumor biology (5, 6) and an increasing body of data indicate that they regulate the immune response pertinent to tumor immunity (7, 8, 9, 10). In addition, they inhibit the migration of endothelial cells (EC) and tumor cells in vitro and attenuate tumor progression, metastasis and angiogenesis in vivo (5, 6). Nevertheless, the response of T cells, EC, smooth muscle cells and tumor cells to SEMA3F is poorly understood but functional effects are characterized by regulatory responses including anti-migration, cytoskeleton collapse and loss of stress fibers (5, 6, 11). Analysis of SEMA3F signaling mechanisms demonstrated that SEMA3F forms a complex with NRP2 and Plexin A1. This complex attracts the ABL2 tyrosine kinase, which activates p190RhoGAP, resulting in the inactivation of RhoA, a small GTPase that converts GTP to GDP, leading to depolymerization of F-actin and the loss of stress fibers with an associated diminished EC and tumor cell migratory response (6).

Gleevec (imatinib), an ABL2 tyrosine kinase inhibitor abrogates SEMA3-mediated loss of stress fiber formation and motility in glioblastoma cells and EC (12). H157 lung cancer cells stably transfected with SEMA3F have reduced levels of phosphorylated Akt (S473), STAT3 and Erk (13), and reduced Akt activity was associated with lower levels of expression of the angiogenic factor, vascular endothelial growth factor (VEGF) (13).

While semaphorins and NRP-elicited responses may regulate multiple intracellular signaling pathways, a common feature is the inhibition of the phosphorylation of the Akt kinase (2,13). This effect is highly suggestive that a major biological effect of semaphorin-induced signaling involves the inhibition of mTOR signaling. Indeed, a recent study demonstrated that invertebrate semaphorin-plexin interactions may regulate TOR signaling in Caenorhabditis elegans (C. elegans), which is required for morphological changes in its epidermal cells (14). mTOR is a serine/threonine kinase that exists as two distinct multiprotein complexes, composed of either mTOR, raptor and mLST8 (mTORC1) (15, 16), or mTOR, rictor, Sin1, protor and mLST8 (mTORC2) (17, 18, 19). mTORC1 controls cell growth in part by phosphorylating S6K1 and 4EBP1 and is a key regulator of protein translation (20, 21). mTORC2 mediates cell survival and activation by phosphorylating Akt (22) and serum/glucocorticoid-regulated kinase-1 (SGK1) and PKC<(18, 23). There is great interest in targeting mTOR signaling pathways as a therapeutic for autoimmune disease, chronic inflammation and allograft rejection (24, 25, 26) and as an adjunct to cancer therapy (27). Nevertheless, little is reported on the effects of SEMA3F on this signaling pathway or in these disease processes despite widespread expression of its NRP2 receptor on human immune, epithelial and tumor cells (5, 6, 28).

It is described herein that SEMA3F interacts with NRP2 and Plexin A1 to reduce PI-3K activity, inhibit the assembly of mTORC2 and reduce downstream Akt signaling. It is also demonstrated that SEMA3F can elicit anti-tumor and anti-angiogenic effects by inhibiting PI-3K activity and Akt-induced transactivation of VEGF, which is well established to function in tumorigenesis and chronic inflammation. Collectively, these studies define SEMA3F as a novel PI-3K/mTORC2 inhibitor in mammalian cells, indicating that it has broad biological and clinical implications, and is a therapeutic to enhance the resolution of chronic disease.

Results

Figure 28A:
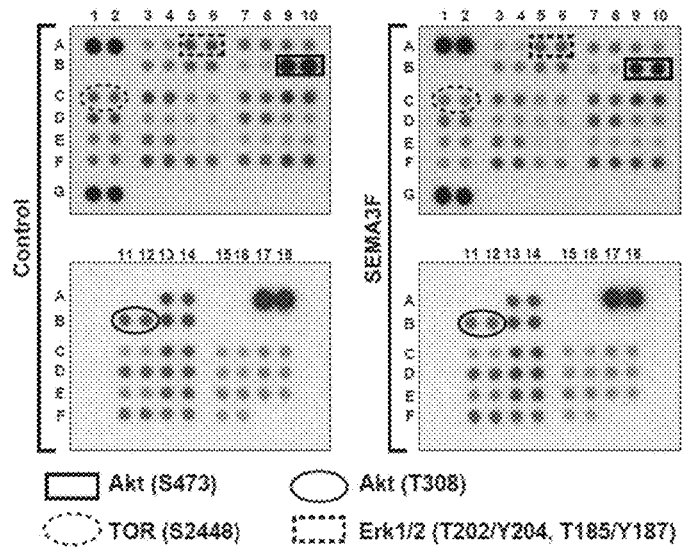
FIGS. 28A-28D show data demonstrating that SEMA3F inhibits the phosphorylation of Akt, mTOR and S6K.
Figure 28B:
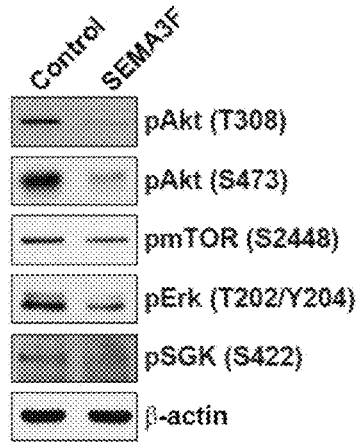
Figure 28C:
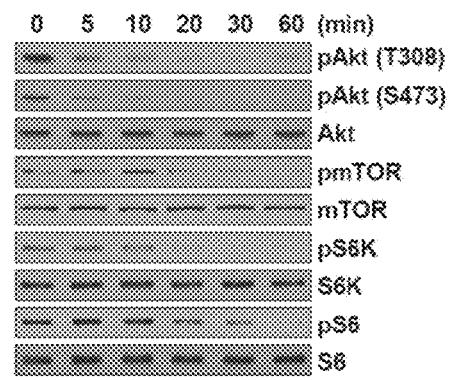
Figure 28D:
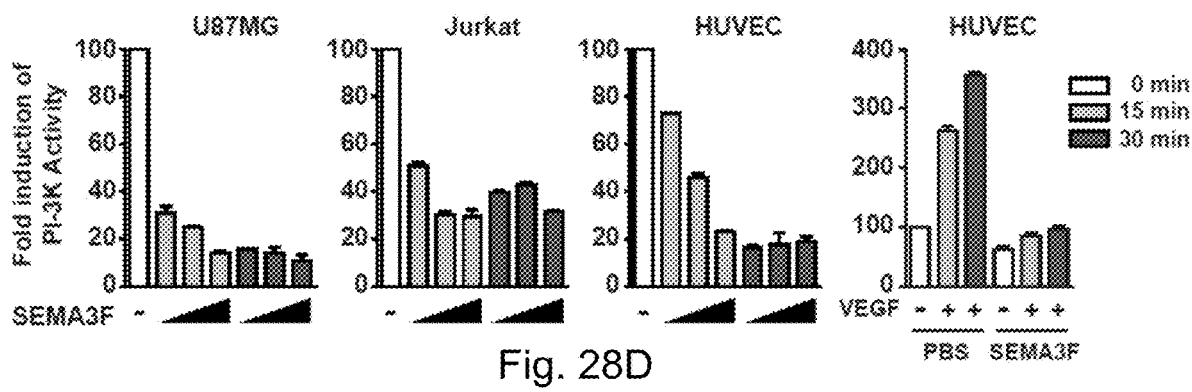
Figure 34A:
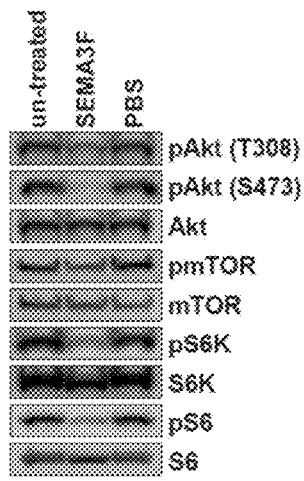
FIGS. 34A-34D depict analysis of intracellular signaling pathway regulated by SEMA3F.
Figure 34B:
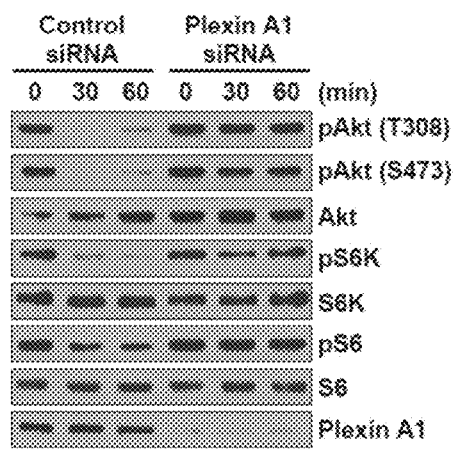
Figure 34C:
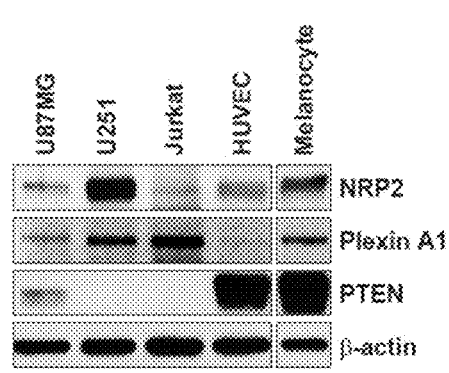
Figure 34D:
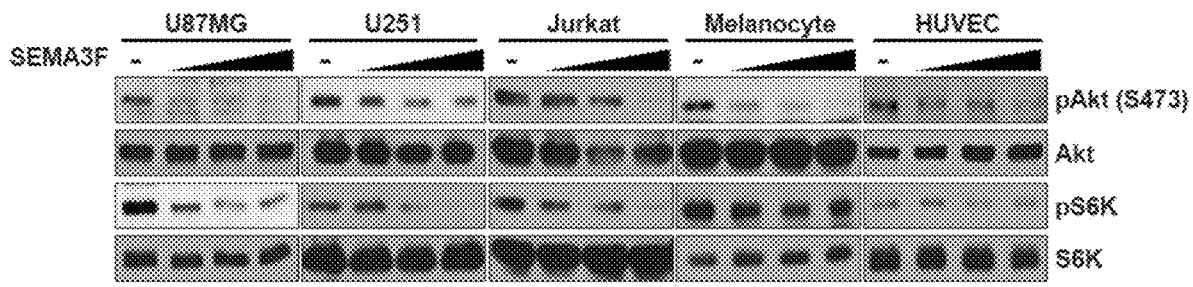

SEMA3F inhibits Akt, mTOR, and S6K phosphorylation. To determine the effect of SEMA3F on intracellular signaling responses, levels of phosphokinases in the NRP2-expressing human glioblastoma cell line U87MG were profiled. It was found that SEMA3F inhibited the phosphorylation of a number of kinases, notably, Akt (T308 and S473), Erk (T202/Y204 and T185/Y187) and mTOR (S2448) (FIG. 28A; Table 1), which was confirmed by Western blot analysis (FIG. 28B). A time course analysis further indicated that pAkt (T308 and S473), pmTOR and its downstream signaling (pS6K and pS6) were inhibited within 10-20 minutes of SEMA3F treatment, and this inhibitory effect persisted for greater than 60 minutes (FIGS. 28C and 34A). SEMA3F failed to inhibit pAkt, pS6K and pS6 in both NRP2 and Plexin A1-siRNA transfected cells, indicating that the regulatory effect of SEMA3F on Akt/mTOR activity requires interaction with NRP2/Plexin A1 complexes at the cell surface (FIG. 19, top panel and 34B). SEMA3F also inhibited Akt (S473) and S6K phosphorylation in several other cell lines expressing NRP2, including U251 glioblastoma cells, a melanocyte cell line, Jurkat T lymphocytes, and endothelial cells (FIGS. 34C-34D). Using a standard ELISA-based assay29, it was also found that SEMA3F inhibited PI-3K activity in each cell line in a time dependent manner (FIG. 28D). In addition, pre-treatment of endothelial cells with SEMA3F (for 30 minutes) inhibited subsequent VEGF-induced PI-3K activation (FIG. 28D). These results indicate that SEMA3F-NRP2 interactions are regulatory to inhibit the activity of PI-3K-Akt/mTOR signaling.

Figures 29C, 29D:
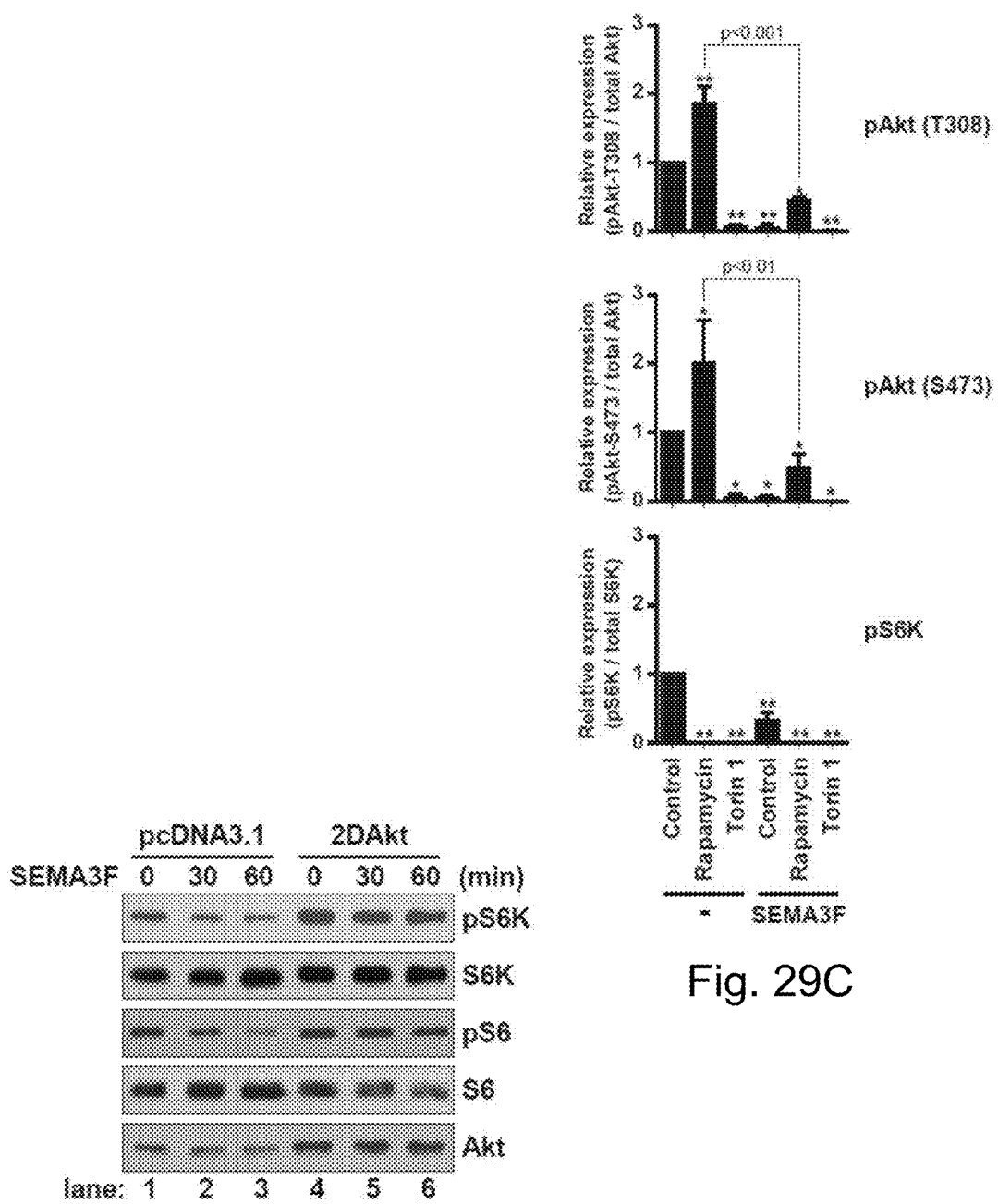

SEMA3F primarily inhibits the assembly of mTORC2. mTORC1 and mTORC2 signaling is critical for cell metabolism (30, 31) as well as the differentiation, proliferation and survival of many normal cell types (27, 32, 33, 34, 35). By immunoprecipitation, it was found that SEMA3F inhibited the association between mTOR and both raptor and rictor (FIG. 29A), suggesting a biological effect on both mTORC1 and mTORC2 respectively. Indeed, cells treated with SEMA3F for 60 minutes had reduced levels of pAkt (T308 and S473) and pS6K (vs. untreated cells, FIG. 29B, lane 1 vs. 4). To determine if its primary mode of function relates to the inhibition of mTORC1 vs. mTORC2, cells were pretreated with rapamycin (10 nM for 30 minutes to inhibit mTORC1) and subsequently the cells were cultured in the absence or presence of SEMA3F and rapamycin for another 60 minutes. Treatment with rapamycin alone (for 90 minutes) as a control resulted in a marked inhibition of pS6K, but an induction in the levels of pAkt (T308 and S473) by 1.9-(p<0.001) and 2.0-fold (p<0.01), respectively (FIG. 29B, lanes 1 vs. 2 and FIG. 29C), as previously reported (36, 37, 38). In contrast, U87MG cells that were treated with rapamycin for 30 minutes and subsequently treated with SEMA3F and rapamycin for an additional 60 minutes had reduced levels of both pAkt and pS6K (FIG. 29B, lane 2 vs. 5). Of note, this effect of SEMA3F on the inhibition of pAkt expression was similar to that observed when cells are treated with the ATP competitive mTORC1/$C_2$ inhibitor Torin 1 (FIG. 29B, lane 3 vs. 4). SEMA3F also inhibited pSGK1 (S422) and pPKC<(S657, FIG. 28B and FIG. 35A), other known targets of mTORC2 activity (23).

Figure 30B:
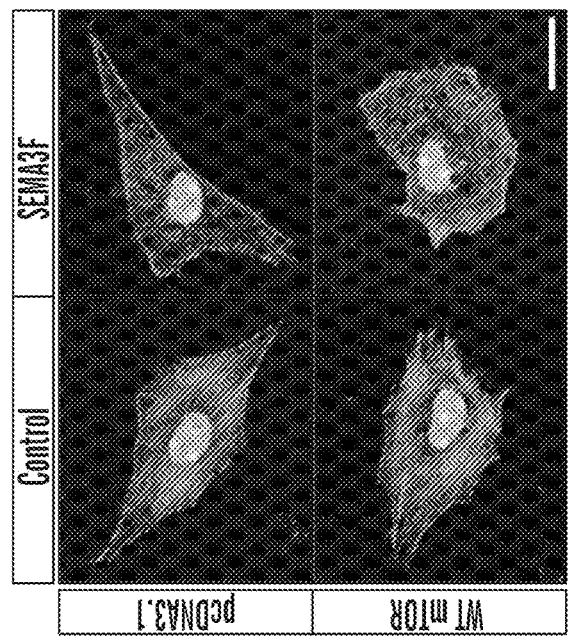
FIGS. 30A-30E show data demonstrating that mTORC2 participates in SEMA3F-induced RhoA inactivation and loss of stress fibers.
Figure 30B:
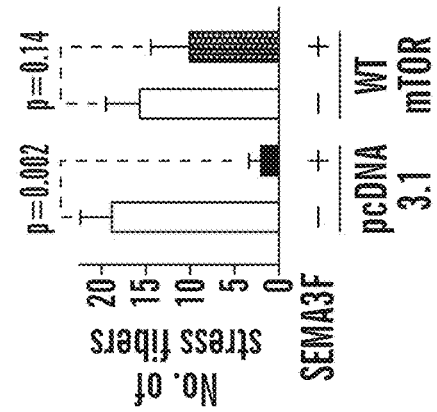
Figure 30A:
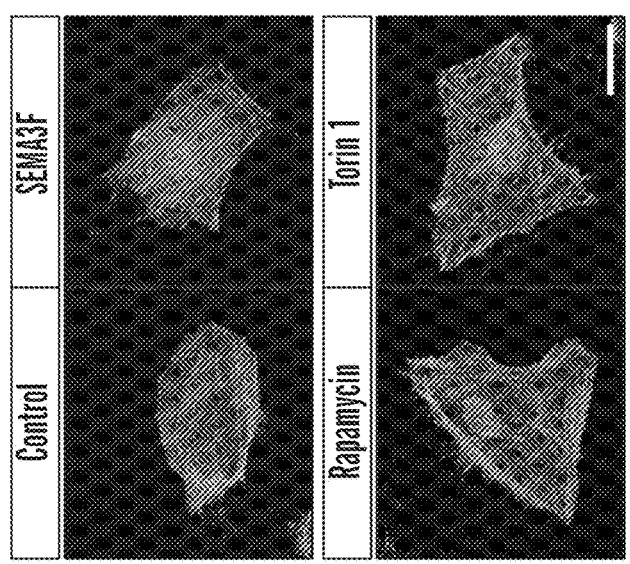
Figure 30A:
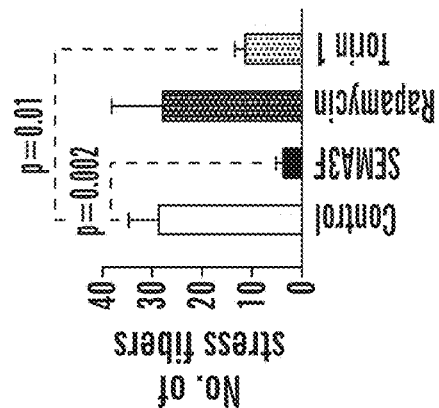
Figure 30C:
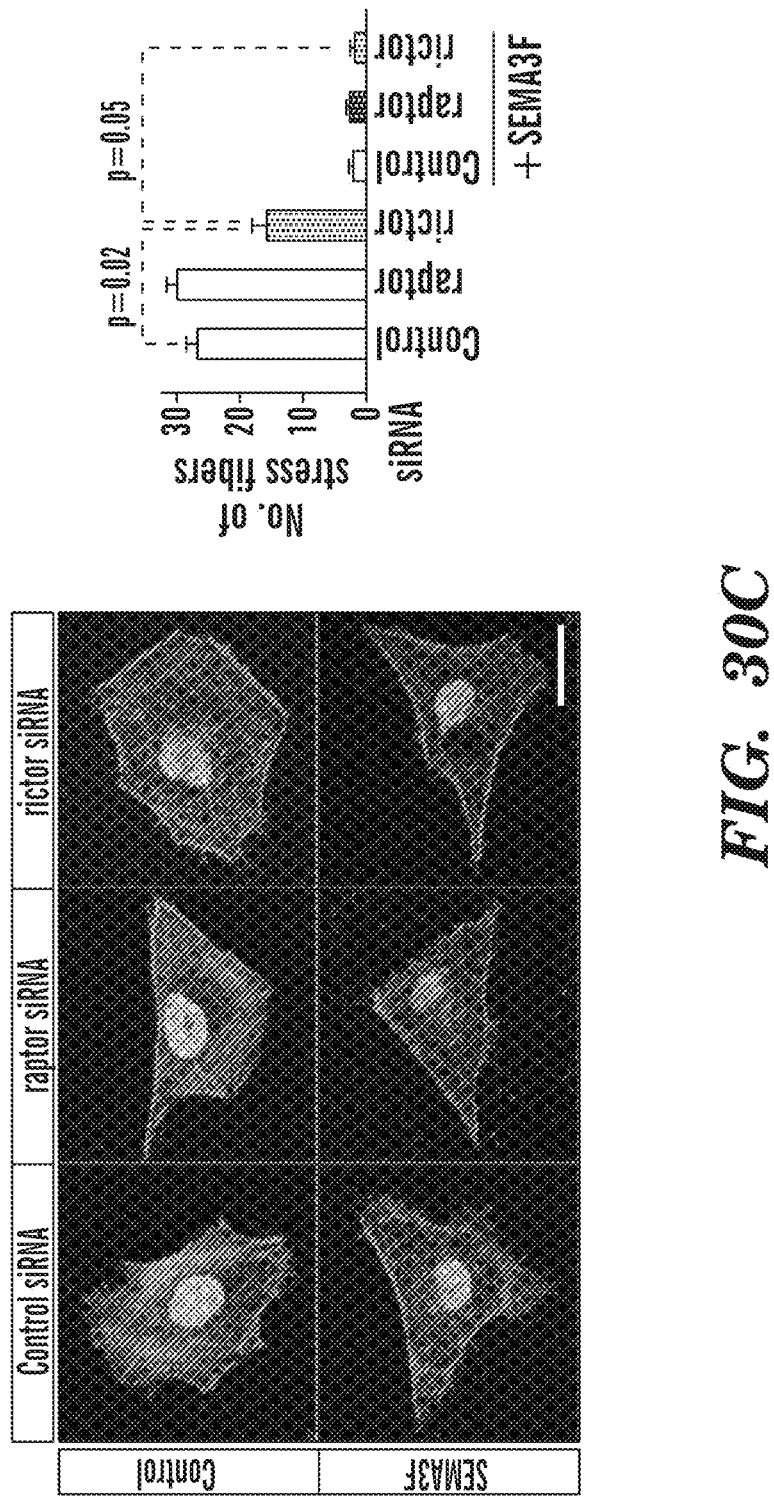
Figure 35A:
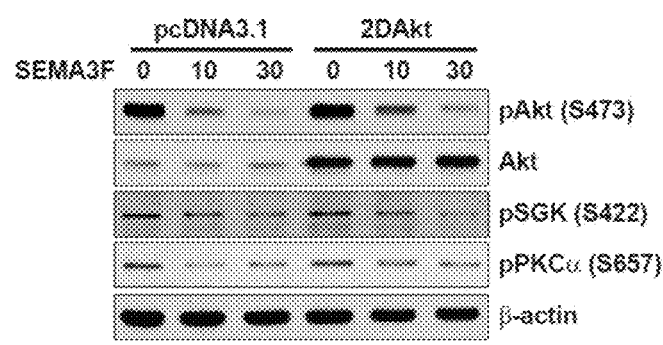
FIGS. 35A-35B depict analysis of the effect of SEMA3F on mTORC2 activity.
Figure 35B:
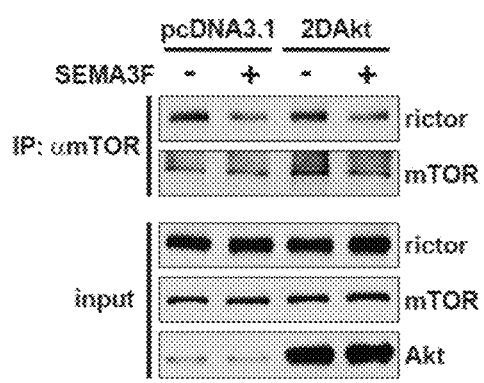

To further evaluate whether the primary biological effect of SEMA3F is on mTORC2 complex formation, U87MG cells were next transfected with 2DAkt, in which the T308 and S473 sites are mutated to encode a constitutively active form of the kinase (36, 37). Overexpression of 2DAkt in EC resulted in mTORC1 activation, and that rapamycin inhibited 2DAkt-induced signaling responses (37). Similarly, transfection of 2DAkt was associated with induced levels of expression of pS6K and pS6 in U87MG cells vs. control transfectants (FIG. 29D, lane 1 vs. 4), but there was no change in expression following treatment of transfected cells with SEMA3F. It was also found that SEMA3F reduced the level of pAkt (S473) in 2DAkt transfectants (FIG. 35A). Moreover, by immunoprecipitation, the treatment of 2DAkt transfected cells with SEMA3F inhibited mTOR/rictor interaction (FIG. 35B), which is consistent with its primary effect on mTORC2 assembly. Together, these results demonstrate that SEMA3F/NRP2/Plexin A1 interactions have a direct effect on the inhibition of mTORC2/Akt activity.

mTORC2 links SEMA3F biology with the F-actin cytoskeleton. It was next determined whether the inhibition of mTORC2 serves as an intermediary response to link SEMA3F activity with cytoskeletal collapse. U87MG cells were treated either with SEMA3F (640 ng/ml), rapamycin (10 nM) or Torin 1 (10 nM) for 30 minutes and the actin cytoskeleton was visualized using phalloidin staining. SEMA3F markedly inhibits stress fiber formation and cytoskeletal arrangement compared to untreated cells (FIG. 30A, p=0.002). Moreover, a similar effect was observed in cells following treatment with the mTORC1/C2 inhibitor Torin 1 (p=0.01). In contrast, treatment with the mTORC1 inhibitor rapamycin failed to elicit any cytoskeletal changes (FIG. 30A; FIGS. 35A-35B). Also, while SEMA3F inhibited stress fiber formation by 90% in pcDNA3.1 control vector transfected cells, it had minimal effects on stress fiber formation in U87MG cells transfected with an mTOR overexpression construct (FIG. 30B). These findings indicate that SEMA3F has minimal direct effects on mTORC1. Consistent with this interpretation, knockdown of raptor also had minimal effects on stress fiber formation and cytoskeleton collapse (FIG. 30C). However, SEMA3F reduced stress fiber formation in raptor-siRNA treated cells (FIG. 30C); and notably, siRNA knockdown of rictor alone was sufficient to elicit collapse (p=0.02). These data suggest that mTORC2 serves as an intermediary to modulate SEMA3F-inducible cytoskeletal collapse.

Figure 30D:
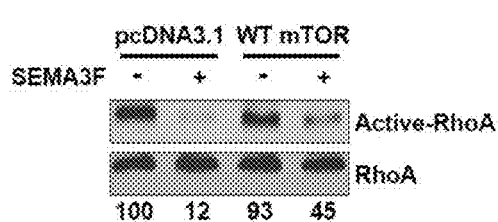
Figure 30E:
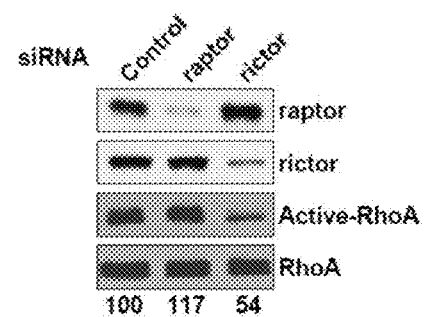

RhoA activity (39) was measured using the rhotekin pulldown assay in U87MG cells transfected with the mTOR overexpression construct (FIG. 30D). RhoA activity was suppressed by SEMA3F in control pcDNA3.1-transfected cells (by 88%), but activity was partially rescued in cells overexpressing mTOR (by 55%). In addition, using siRNAs (as above) it was found that knockdown of rictor, but not raptor, attenuated RhoA activity (FIG. 30E). Collectively, these observations demonstrate that the inhibition of mTORC2 activity by SEMA3F/NRP2/Plexin A1 interactions is functional to inactivate RhoA, which in turn leads to cytoskeleton collapse. Thus, upstream regulation of mTORC2 activity by SEMA3F has potential to target multiple biological responses.

Figures 31A, 31B, 31C, 31D:
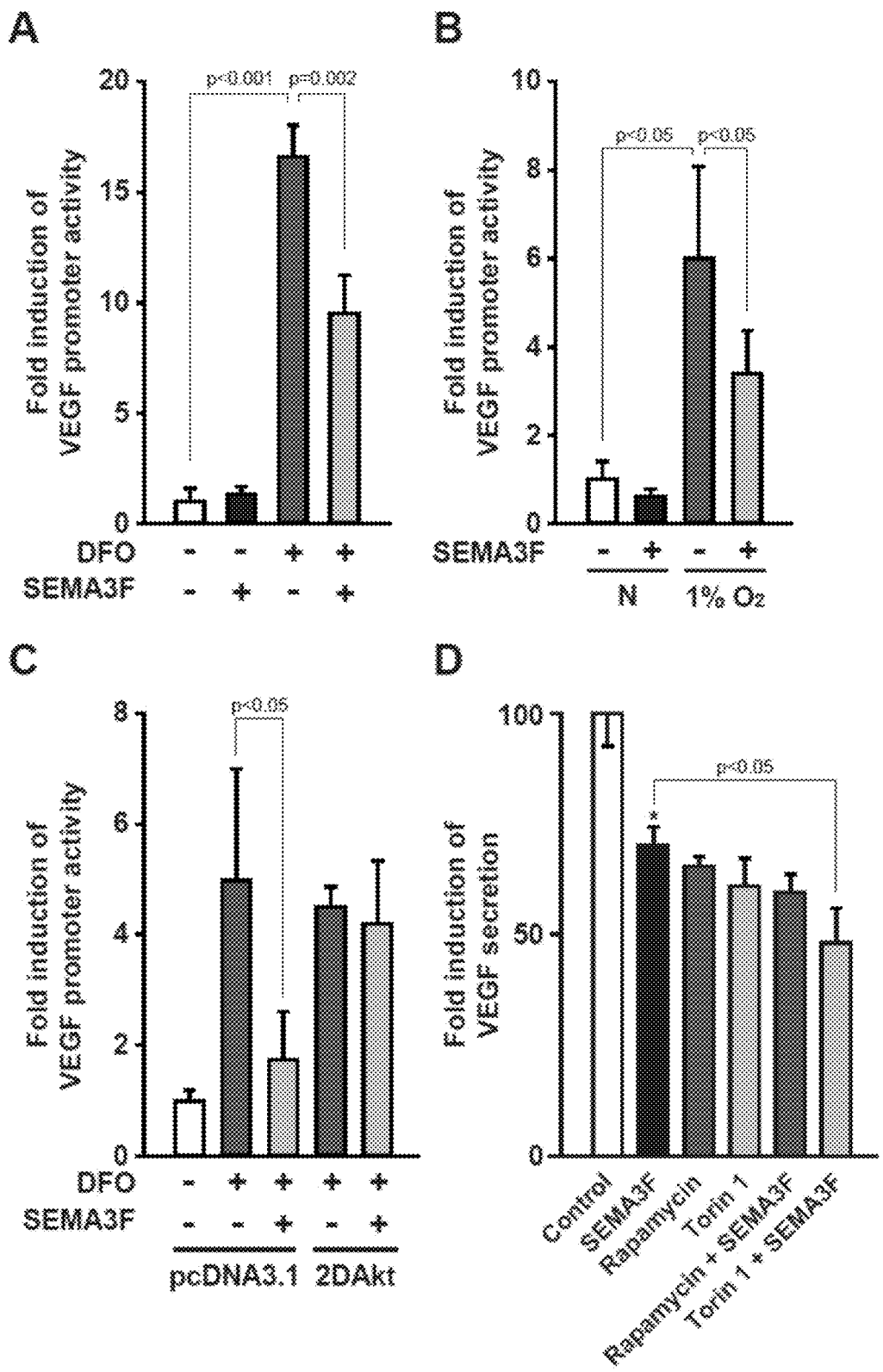
FIGS. 31A-31D show data demonstrating that SEMA3F suppresses VEGF through the inhibition of mTOR-Akt signals.

SEMA3F inhibits hypoxia-induced production of VEGF via the mTOR pathway. The local expression and regulation of VEGF is key to many physiological and pathological processes (40, 41). These findings indicate that SEMA3F can target the transcriptional activation of VEGF via its ability to target mTOR kinase activity (36, 42). To test the effect of SEMA3F on the regulation of VEGF expression, U87MG cells were transfected with a full-length 2.6 kb VEGF promoter-luciferase construct and exposed to the hypoxia mimetic agent desferrioxamine (DFO) or hypoxia (1% 02). It was found that treatment with DFO induced VEGF promoter activity (by 16-fold, p<0.001), which was partially inhibited (43%, p<0.005) by SEMA3F (pre-treatment for 30 minutes, FIG. 31A). VEGF promoter activity was also increased (as expected43) following 18 hours culture in 1% 02 (FIG. 31B); again VEGF promoter activity was reduced following treatment with SEMA3F (44%, p<0.05), but not to basal levels. To test the relative effect of SEMA3F on mTORC1/C$_2$, U87MG cells transiently co-transfected with the 2DAkt construct and the full length VEGF promoter reporter construct, and the cells cultured in the absence or presence of SEMA3F. It was found that SEMA3F failed to attenuate VEGF promoter activity in 2DAkt transfected cells following treatment with DFO (FIG. 31C). Finally, the effect of SEMA3F on the secretion of VEGF into conditioned media (by ELISA) was determined in the absence or presence of DFO. DFO markedly increased VEGF production (by 160% compared to untreated cells, p<0.001 (data not shown). Furthermore, DFO-induced VEGF protein secretion was significantly reduced by SEMA3F, the mTORC1 inhibitor rapamycin (for 18 hours to target mTORC1/C2) and by the mTORC1/C2 inhibitor Torin 1 (FIG. 31D, p<0.01). Concomitant treatment of the cells with rapamycin and SEMA3F failed to further suppress VEGF production, but the combination of SEMA3F and Torin 1 slightly (but significantly p<0.05) inhibited VEGF levels as compared to SEMA3F or Torin 1 alone (FIG. 31D). Collectively, these findings indicate that SEMA3F suppresses inducible VEGF expression in part via the regulation of mTOR activity.

Figures 32A, 32B, 32C, 32D, 32E:
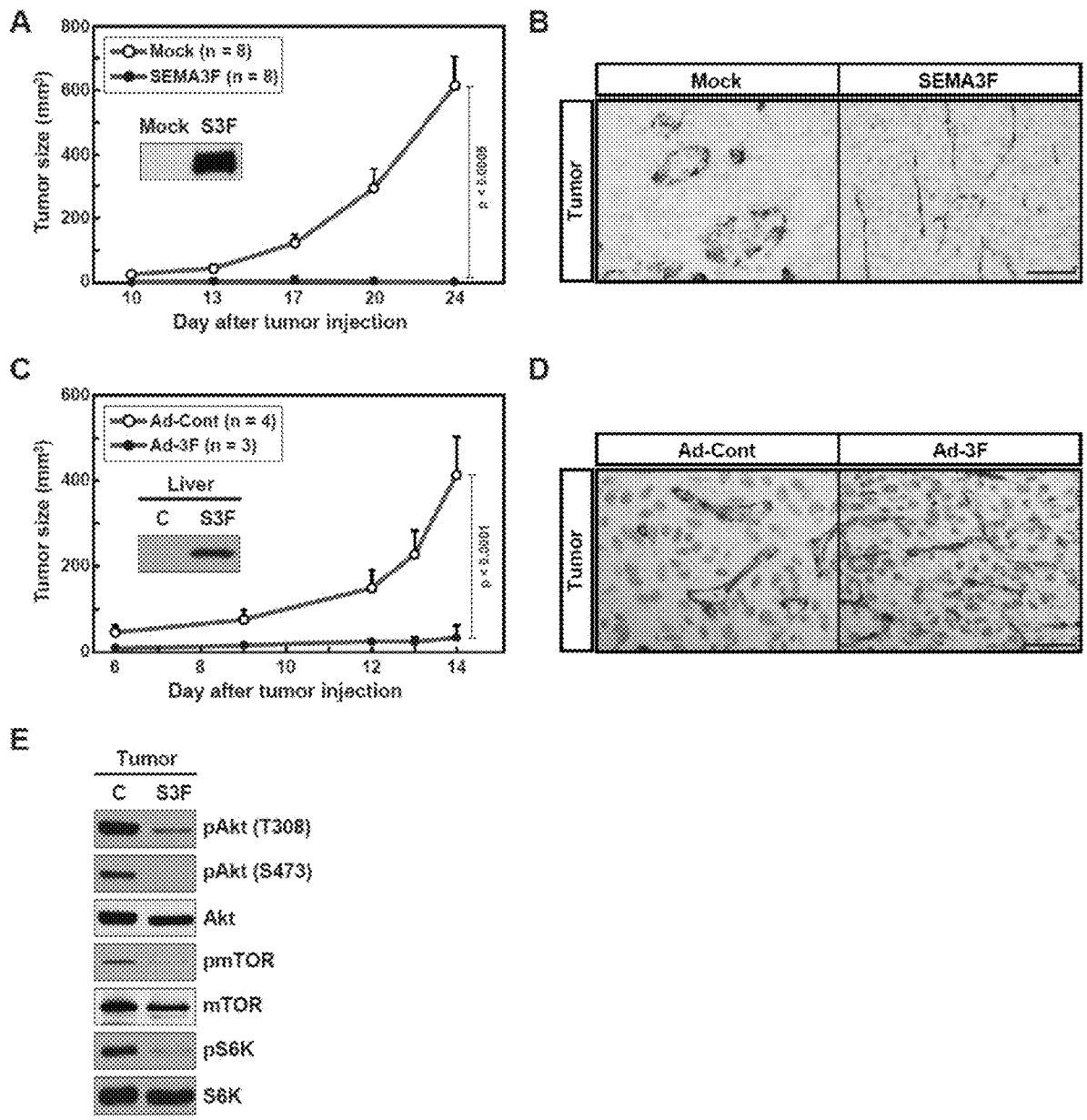
FIGS. 32A-32E show data demonstrating that SEMA3F inhibits human tumor growth in xenografts in vivo.

SEMA3F inhibits U87MG tumor growth and angiogenesis in vivo. To determine the in vivo relevance of our signaling studies, the effect of SEMA3F on tumor growth was evaluated in a well-established xenograft model (5, 44, 45). In one approach, parental U87MG cells or U87MG cells that were engineered to constitutively overexpress SEMA3F were implanted subcutaneously into nude mice ($1\times10^6$/mouse); tumor size (mm$^3$) was measured at the indicated time points over a period of 3 weeks. It was found that tumor growth was essentially absent when SEMA3F-producing cells were implanted vs. parental cells (p<0.0005, FIG. 32A). Furthermore, immunohistochemical analysis of CD31-expressing EC demonstrated numerous blood vessels in parental U87MG tumors (FIG. 32B); in contrast, capillaries within the U87MG/SEMA3F-derived tumors were constricted and were without discernable lumens (FIG. 32B). A second approach involved the injection of $1\times10^6$ U87MG cells into the skin of nude mice, and after 2 days the mice received a single intravenous injection of adenovirus encoding human SEMA3F tagged with His (Ad-3F) or a control adenovirus (Ad-Cont). Injection of Ad-3F ($1\times10^9$ pfu) into mice did not result in any toxicity over a 30-day period; mice gained weight and typical behavior was normal. Western blot analysis showed that the administration of Ad-3F resulted in high levels of SEMA3F production in the liver (FIG. 32C), and by ELISA, SEMA3F levels were measureable in the serum. Circulating serum levels of SEMA3F protein peaked on day 8 following administration of adenovirus (day 10 post injection of tumor cells), and persisted until the end of the experiment on day 14 (average of 26 ng/ml, n=4). Thus, this approach enables circulating SEMA3F production to begin at a time after tumor growth has been established in the mouse. Tumor volume reached 400 mm$^3$ by day 14 in Ad-Cont-treated mice, whereas tumor growth was minimal over a 14 day period in mice injected with Ad-3F (p<0.0001, FIG. 32C). By immunostaining, there was a striking collapsed phenotype of CD31-expressing capillaries within tumors harvested from Ad-3F-treated mice and most blood vessel lumens did not appear patent (FIG. 32D). Furthermore, by Western blot analysis, it was found that pAkt, pmTOR and pS6K levels were suppressed in tumors following treatment with Ad-3F, as compared to Ad-Cont treated mice (FIG. 32E). Thus, in two very different approaches, SEMA3F administration (local and/or systemic) has similar anti-tumor effects. Together, these results demonstrate that SEMA3F inhibits tumor growth and angiogenesis by inhibiting the Akt/mTOR signaling pathway.

Discussion

Semaphorins were first shown to be mediators of axon guidance and pathfinding and they were subsequently found to regulate vascular homeostasis and tumor development (1, 2). In these studies, SEMA3F is defined as a potent mTOR inhibitor, and its effect is mediated through the inhibition of PI-3K activity and the assembly of mTOR/rictor and mTOR/raptor complexes. It is also found that its functional effect is mediated via interactions with the NRP2-Plexin A1 receptors. The regulation of mTOR by SEMA3F was found in several cell types, including T cells, endothelial cells and tumor cell lines, all of which are well established to utilize this signaling pathway for cellular activation, differentiation and proliferation. These findings indicate that SEMA3F biology is of broad relevance in many physiological and pathological conditions, including cancer and diseases associated with chronic inflammation such as allograft rejection.

While much is known about the intracellular regulation of mTORC1, relatively little is known about the upstream regulation of mTORC2 activity. In C. elegans, it has been shown that invertebrate semaphorin-plexin interactions reduce the association of TOR with rictor but promote TOR/raptor association, resulting in mRNA translation through the 4EBP-eIF4F pathway 14. In contrast, in mammalian cells, the presently presented studies indicate that SEMA3F can serve as a unique soluble ligand to selectively target mTORC2 activity and thus, pro-resolution following cellular activation. For example, transfection of NRP2-expressing cell lines with 2DAkt to activate mTORC1 demonstrated that SEMA3F had minimal effects on the association between mTOR and raptor (data not shown) or the phosphorylation/activation of S6K and S6. In addition, SEMA3F responses were notably different than those observed following a short timecourse treatment with rapamycin, which is known to primarily target mTORC1. In contrast, in several assays, it was found that the inhibitory effects of SEMA3F on cellular activation and cytoskeletal collapse were primarily mediated through its effect on mTORC2 and were similar to those observed following treatment with Torin 1 (a pharmacological inhibitor of mTORC1/C2).

Figure 36A:
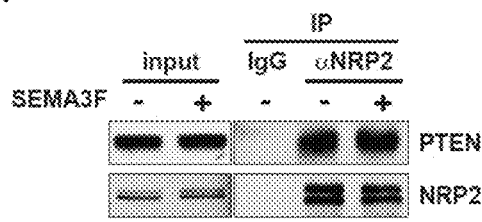
FIG. 36A depicts a western blot. HUVEC were treated with SEMA3F (1800 ng/ml) for 30 minutes and were subjected to immunoprecipitation and Western blot analyses with anti-NRP2 and -PTEN as illustrated.
Figure 36B:
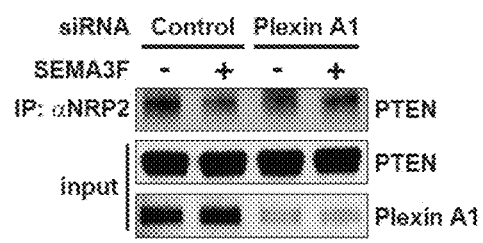
FIG. 36B depicts a western blot. HUVEC were transfected with control-, or Plexin A1-specific siRNAs (20 nM), prior to SEMA3F treatment (1800 ng/ml); lysates were subjected to immunoprecipitation and Western blot analyses with anti-NRP2 and anti-PTEN as illustrated.
Figure 36C:
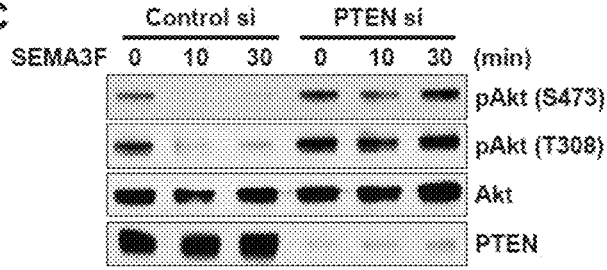
FIG. 36C depicts a western blot. HUVEC were transfected with control-, or PTEN-specific siRNAs (20 nM), prior to SEMA3F treatment (1800 ng/ml); lysates were analyzed by Western blot.

Importantly, it was also found that SEMA3F reduced PI-3K activity which is reported to function in the activation of mTORC2 46, 47. It is thus likely that SEMA3F inactivates mTORC2 via upstream inhibition of PI-3K. Another related family member NRP1 binds and activates phosphatase and tensin homologue deleted on chromosome ten (PTEN) (7), a negative regulator of PI-3K. Without wishing to be bound by theory, it thus postulated that the ligation of NRP2 by SEMA3F can result in the recruitment of PTEN, which in turn serves as an intermediary to regulate PI-3K activity. Consistent with this possibility, it was found that PTEN coimmunoprecipitated with NRP2 in human umbilical vein EC (HUVEC, FIG. 36A). Moreover, following siRNA transfection and knockdown of Plexin A1, by immunoprecipitation, PTEN maintained association with NRP2 (FIG. 36B), suggesting a direct interaction between PTEN and NRP2 (and not Plexin A1) in HUVEC. Furthermore, SEMA3F failed to inhibit pAkt expression following siRNA knockdown of PTEN in HUVEC (FIG. 36C). These findings are most suggestive that the recruitment of PTEN to NRP2 is mechanistic for its regulatory effects on PI-3K/Akt/mTOR signaling.

Figure 36D:
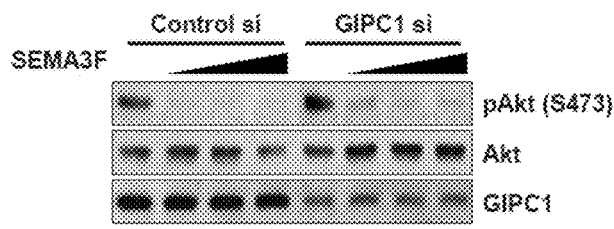
FIG. 36D depicts a western blot. U87MG cells were transfected with control or GIPC1-specific siRNA (20 nM). After 48 hours, cells were treated with SEMA3F (200, 600, 1800 ng/ml, from left to right) for 30 minutes, and were analyzed by Western blot.
Figure 36E:
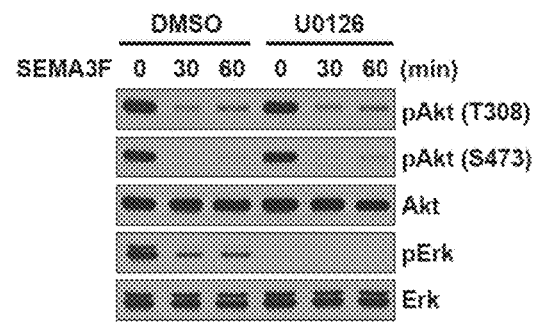
FIG. 36E depicts a western blot. U87MG cells were treated with U0126 (10 μM) for 30 minutes prior to combination with 30 minutes and 60 minutes of SEMA3F (640 ng/ml). Akt and MAPK signaling was analyzed by Western blot. All data presented are representative of 3 independent experiments.

However, U87MG, U251 and Jurkat cells are reported to be relatively PTEN deficient (48, 49, 50) (see FIG. 34C), indicating that SEMA3F may also elicit its regulatory response(s) via PTEN-independent mechanisms. Indeed, as expected, PTEN failed to co-immunoprecipitate with NRP2 in U87MG cells (data not shown). To this end, other adaptors with potential to mechanistically link NRP2 signals with PI-3K activity were screened. These include GIPC1 (GAIP/RGS19-interacting protein, also known as neuropilin-interacting protein or synectin, FIG. 36D) (51, 52, 53), other GIPC family members (52) and DEP domain containing mTOR interacting protein (DEPTOR) (32, 54). However, siRNA knockdown of these adaptors did not alter the regulatory effect of SEMA3F on pAkt expression (data not shown). Crosstalk between the effects of SEMA3F on mTOR/Akt and MAPK signaling were evaluated. The pharmacological MEK inhibitor U0126 did not modulate the regulatory effects of SEMA3F on levels of pAkt, indicating that the inhibitory effect of SEMA3F on Akt-mTOR signaling is MAPKindependent (FIG. 36E). Thus, while SEMA3F-NRP2 interactions may recruit PTEN to regulate PI-3K and mTORC2 in primary cultures of normal cells, additional adaptors/kinases may also function in this response.

Figure 33:
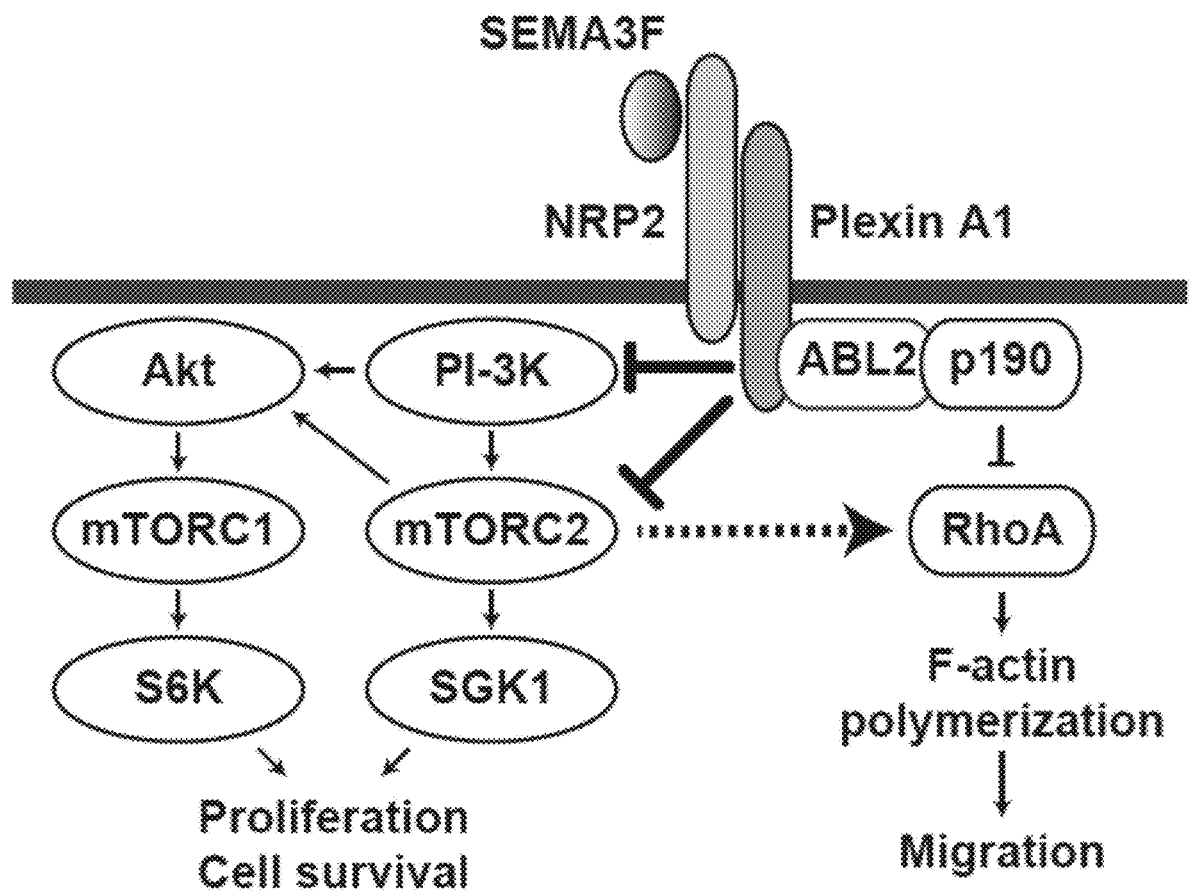
FIG. 33 depicts a schematic cartoon showing regulatory signaling pathways mediated by SEMA3F-NRP2/Plexin A1 interactions. SEMA3F binds to the NRP2-Plexin A1 complex and associates with PTEN to inactivate PI-3K and mTORC2/Akt-dependent signaling. Receptor-mediated signals may also inactivate mTORC2/Akt signaling via PTEN independent mechanisms in tumor cell lines. Functionally, these regulatory/proresolution signals suppress cell proliferation, migration, cytoskeletal stress fiber rearrangement and cell survival. SEMA3F also inhibits cytoskeleton structure in part by inactivating RhoA through both the ABL2 kinase and p190RhoGAP6; the current studies show that the inactivation of RhoA and cytoskeletal stress fiber rearrangement is also mediated via the inhibition of mTORC2.

The semaphorin family of axonal guidance molecules, including SEMA3F, are well established to promote neuronal growth cone collapse that results from concomitant rearrangement of actin cytoskeletal stress fibers. SEMA3F is a potent inhibitor of tumor cell and EC adhesion, spreading and motility in vitro and in vivo (5, 6). In addition, SEMA3F does not induce apoptosis in U87MG cells within 24 hours6. In tumor and vascular endothelial cells, SEMA3F inactivates RhoA, thereby inhibiting cytoskeletal stress fiber formation6, 12. It is demonstrated herein that mTORC2 is an intermediary in this response, and is indispensable for RhoA inactivation. For example, SEMA3F treatment results in cell collapse following transfection of cells with mTOR (to induce mTORC1), suggesting that this effect is either mTOR-independent and/or is associated with targeting of mTORC2. Consistent with an effect on mTORC2, siRNA knockdown of rictor and the treatment of U87MG cells with the mTORC2 inhibitor Torin 1 consistently reduced the number of stress fibers as observed following treatment with SEMA3F. Furthermore, SEMA3F reduced the number of stress fibers in raptor siRNA (mTORC1) knockdown cells. Importantly, SEMA3F further reduced stress fibers in rictor siRNA treated cells, indicating that SEMA3F likely inactivates RhoA in part via mTORC2 and in part via the ABL2/p190RhoGAP pathway (FIG. 33). Although mTORC2 is reported to interact with the Rho GTPase family and mediate F-actin cytoskeleton re-organization (18, 55), it is demonstrated herein that this effect can be targeted through stimulation of NRP2-induced signals.

mTORC2-dependent activation of Akt functions in the transcriptional activation of VEGF in endothelial cells (36). VEGF functions as a proangiogenesis factor to augment tumor growth, and as a leukocyte chemoattractant in association with chronic inflammation (43). Since SEMA3F targets mTORC2 activity, it was also assessed whether it has any biological impact on the inducible expression of VEGF. It was found that SEMA3F markedly inhibits inducible VEGF expression via the inhibition of both mTORC2 and mTORC1. However, SEMA3F fails to inhibit the transactivation of VEGF following transfection of cells with the 2DAkt construct which induces mTORC1 activation. It was also found that treatment with either SEMA3F or rapamycin (long-term treatment to inhibit both mTORC1/C2) or the mTORC1/C2 inhibitor Torin 1 results in a similar level of inhibition of VEGF expression in U87MG cells. There was no additional inhibitory effect of combined SEMA3F and rapamycin, suggesting that SEMA3F and rapamycin target the same signaling pathway. However, surprisingly SEMA3F partially augmented the inhibitory effect of Torin 1 on VEGF expression. This may suggest that the Torin 1 dose used in these studies was not sufficient to completely inhibit mTORC2, or alternatively, it is possible that Torin 1 uncovers additional SEMA3F-elicited regulatory mechanism(s). Of note, SEMA3F alone fails to inhibit VEGF expression to basal levels, yet it has been previously reported to inhibit VEGFinduced proliferation of EC (56). Nevertheless these new findings suggest that this anti-VEGF effect of SEMA3F may be most significant for its biological effects in vivo, such as our past (5, 6) and current observations of its tumor growth inhibitory potential.

Overexpression of SEMA3F in tumor cells, such as lung, brain and breast cancer cells, significantly inhibits tumor development and angiogenesis in xenograft mouse models (5, 13, 44, 45, 57). In these studies, control or SEMA3F-producing U87MG cells were implanted subcutaneously into nude mice and it was found that the expression of SEMA3F strongly inhibited tumor growth and angiogenesis. Furthermore, an adenovirus was used to evaluate the effects of high levels of circulating SEMA3F protein on tumor growth and angiogenesis after tumors have developed. Most notably, circulating SEMA3F markedly inhibited tumor growth. However, all neoangiogenic blood vessels within the growing tumors had a dramatic collapsed phenotype, which is consistent with known SEMA3F effects on the cytoskeleton (6). In addition, lysates of tumors from SEMA3F-treated mice showed diminished levels of pAkt, pmTOR and pS6K, which is consistent with its effects in vitro. Therefore, in the in vivo models, SEMA3F is likely to have large impact on tumor growth via both the suppression of VEGF secretion and direct inhibition of Akt-mTOR signaling within tumors, as well as via effect on endothelial cells that inhibit angiogenesis. Also, the marked inhibition of tumor growth obtained by two different approaches (local overexpression by the tumor and by systemic administration) confirms that SEMA3F is a potent mTOR inhibitor in vivo.

These findings demonstrate that SEMA3F-NRP2 interactions inhibit intracellular PI-3K activity, mTORC2-dependent signaling, RhoA activity and cytoskeletal stress fiber formation. SEMA3F also inhibits the inducible expression of VEGF at both the transcriptional and protein level in vitro, and it has powerful antitumor effects in vivo. SEMA3F is a secreted physiological mTOR inhibitor that functions to promote resolution following cellular activation. These findings have broad clinical implications, including the use of SEMA3F for therapeutic purposes, for instance, to target chronic immune-mediated diseases, allograft rejection or angiogenesis related pathology, such as tumor growth and progression.

Methods

Antibodies and reagents: The antibodies, rabbit monoclonal anti-phospho-Akt (Thr308) antibody (#2965); mouse monoclonal anti-phospho-Akt (Ser473) antibody (#4051); rabbit polyclonal anti-Akt antibody (#9272); rabbit polyclonal anti-phospho-Erk1/2 (Thr202/Tyr204) antibody (#9101); mouse monoclonal anti-Erk1/2 antibody (#4696); rabbit monoclonal anti-phospho-S6K (Thr389) antibody (#9234); rabbit monoclonal anti-S6K antibody (#2708); rabbit monoclonal anti-phospho-S6 (Ser235/236) antibody (#4856); mouse monoclonal anti-S6 antibody (#2317); rabbit monoclonal anti-phosphomTOR (Ser2448) antibody (#5536); rabbit polyclonal anti-mTOR antibody (#2972); rabbit polyclonal anti-plexin A1 antibody (#3813); rabbit monoclonal anti-raptor antibody (#2280); rabbit monoclonal anti-RhoA antibody (#2117); rabbit monoclonal anti-PTEN antibody (#9188) were all purchased from Cell Signaling Technology (Danvers, MA). Goat polyclonal anti-phospho-SGK (S422, sc-16745); mouse monoclonal anti-NRP2 antibody (C-9, sc-13117); goat polyclonal anti-GIPC antibody (N-19, sc-9648) were purchased from Santa Cruz Biotechnology, Inc (Dallas, TX). Rabbit polyclonal anti-rictor antibody (A300-458A) was purchased from Bethyl Laboratories, Inc (Montgomery, TX), and mouse monoclonal anti-β-actin antibody (AC-15) was from Sigma-Aldrich (St. Louis, MO).

The VEGF-A (DVE00) ELISA kit was obtained from R&D Systems (Minneapolis, MN). The PI3-Kinase Activity ELISA (K-1000s) was purchased from Echelon Biosciences (Salt Lake City, UT). The mTOR inhibitors, rapamycin and Torin 1, were purchased from Lc Laboratories (Woburn, MA) and R&D Systems, respectively. Desferrioxamine (DFO) was purchased from Sigma-Aldrich, and the MEK inhibitor (U0126) was purchased from EMD-Millipore (Billerica, MA). pGL4.74 [hRluc/TK] vector (Promega Madison, WI) was used as an internal control in luciferase assay.

Cell culture: U87MG and U251 human glioblastoma cells, kidney 293 cells and 293T cells, and Jurkat T lymphocytes were obtained from American Type Culture Collection (ATCC, Manassas, VA) and cultured in media containing 10% FBS (Denville Scientific, Inc., South Plainfield, NJ) and 1% L-glutamine/penicillin G/streptomycin sulfate (1% GPS, Life Technologies) as recommended. HUVECs were purchased from Lonza (Walkersville, MD) and cultured in EBM2 medium supplemented with EGM2 SingleQuot. Human melanocytes (HEMn-LP, Life Technologies) were maintained with Medium 254 supplemented with Human Melanocyte Growth Supplement (Life Technologies) in a 5% CO2 incubator at 37° C. For all hypoxia experiments, cells were cultured in a hypoxic chamber (Heracell, Thermo Scientific, Hudson, NH) in 1% O2 at 37° C.

Human recombinant SEMA3F: A full-length, His-Myc-tagged human SEMA3F construct was transfected into 293T cells using FuGENE HD Transfection Reagent (Roche, Basel, Switzerland). SEMA3F secreted into culture medium was purified on HiTrap™ HP Chelating columns (GE Healthcare Bio-Sciences Corp., Pittsburgh, PA) (60).

Phospho-kinase array: The Human Phospho-Kinase Array Kit (ARY003) was obtained from R&D Systems. U87MG cells were treated with SEMA3F which was previously found to induce cytoskeletal collapse and inhibit RhoA activity (6). U87MG cells were previously treated with SEMA3F at 320 ng/ml which was found to induce morphological changes and inhibit cell migration in U87MG cell and HUVEC. Consistent with these results, we find that SEMA3F (even at the lowest concentration 200 ng/ml) inhibits pAkt and pS6K signaling (FIG. 34D). However, in other cell types, this concentration was found to be suboptimal to suppress these signals. Thus, a concentration at 640 ng/ml was optimized to analyze SEMA3F signaling pathways. Cell lysates were collected at 30 minutes after SEMA3F treatment and the levels of phosphoproteins were analyzed with this array, according to the manufacturer's instructions.

Western blotting: Proteins within each sample were separated by SDS-PAGE and transferred to nitrocellulose membranes. The membranes were blocked with 4% skimmed milk in TBS-T (0.1% Tween 20 in tris-buffered saline [TBS]) for 30 minutes, followed by incubation with the primary antibody. After washing with TBS-T, membranes were incubated with the appropriate horseradish peroxidase-conjugated secondary antibody, and immunoreactivity was detected by using ECL detection reagents.

Immunoprecipitation: Cell lysates were immunoprecipitated using an appropriate antibody at 4° C. overnight. Protein G-Sepharose 4 Fast Flow beads (GE Healthcare) were added to each sample, followed by mixing for 1 hour at 4° C. The samples were dissolved in SDS sample buffer and boiled for 5 minutes.

F-actin staining: Cells were fixed with 4% paraformaldehyde (PFA) followed by permeabilization with 0.2% Triton X-100 in PBS. F-actin and nuclei were stained with Alexa Fluor 488 phalloidin and Hoechst 33342, respectively. Confocal images from 3-5 areas of each culture were reviewed and stress fibers were counted in representative individual cells (~5/experiment) using standard methodology as described6.

RhoA activity: RhoA activity assays were measured by using the RhoA activation assay kit based on rhotekin pull-down, according to the manufacturer's instructions (Cytoskeleton, Denver, CO).

RNA interference: Transfection of siRNA (20 nM) was performed with siLentFect Lipid Reagent (Bio-Rad, Hercules, CA), according to the manufacturer's protocol. Control siRNA (Silencer Negative Control #2 siRNA) was purchased from Life Technologies. ON-TARGETplus™ Human NRP2 siRNA was purchased from Thermo Scientific (Hudson, NH), Plexin A1 (Hs_PLXNA1_3), rictor (Hs_RICTOR_5), PTEN (Hs_PTEN_6) and GIPC1 (Hs_RGS19IP1_1) siRNA from Qiagen (Valencia, CA), and Raptor siRNA (sc-44069) from Santa Cruz Biotechnology, Inc. (Dallas, TX). In general, siRNA transfection was performed for 48 hours prior to assays.

Transfection and Luciferase assay: U87MG cells were transiently transfected with plasmid constructs (pcDNA3.1, WT mTOR, 2DAkt, VEGF luciferase reporter plasmid or pGL4.74 [hRluc/TK]) as indicated using Lipofectamine 2000 reagent (Life Technologies) according to the manufacturer's instructions. After 18 hours, cells were treated as outlined in each experimental design. VEGF promoter activity was analyzed using a Dual-Luciferase Reporter Assay System (Promega), and luciferase activity was normalized by Renilla luciferase as an internal control.

Adenovirus: Recombinant control (#000047A) and human SEMA3F-His (#129755A) adenovirus were purchased from Applied Biological Materials, Inc. (Richmond, Canada). Each adenovirus was amplified with 293 cells and purified using the Fast Trap Adenovirus Purification and Concentration Kit (EMD-Millipore). The adenovirus titer was determined by Adeno-X™ Rapid Titer Kit (Clontech Laboratories, Inc., Mountain View, CA). Adenovirus was obtained at titers greater than $1 \times 10^{10}$ pfu/ml.

Tumor xenograft model: Parental U87MG cells or human SEMA3F stable U87MG clones ($1 \times 10^6$/injection) were administrated into nude mice (male, 8-10 weeks of age) subcutaneously. In one model, tumor size was measured every 3-4 days using a standard calipers. Mice were sacrificed on day 24 and tumors were removed. In a second model, parental U87MG cells were administrated into nude mice subcutaneously. In pilot studies, adenovirus encoding SEMA3F (Ad-3F) or a control adenovirus (Ad-Cont) was injected intravenously via the tail vein 3 days prior to tumor cell injection ($1 \times 10^6$ U87MG cells/injection); we observed that all tumors in the Ad-3F group failed to grow (data not shown). Thus, we revised our approach, and administration of Ad-3F was delayed until day 2 after the tumor injection, so that tumor growth was initiated prior to peak SEMA3F production in the circulation (~day 8-10 post administration, data not shown). Tumor size was measured every other day using a standard calipers, serum samples were collected from the tail vein at day 5 and 8 and mice were sacrificed on day 14 when the tumor, the liver and serum samples were collected. Production of SEMA3F was confirmed by Western blot analysis of liver with anti-His/anti-SEMA3F antibodies and by analysis of serum level of SEMA3F using the human SEMA3F ELISA kit (MBS454602) from MyBioSource (San Diego, CA).

Immunohistochemistry: Paraffin-embedded sections were deparaffinized and activated with proteinase K (36 µg/ml) in 0.2 M Tris buffer (pH7.2) at 37° C. for 30 minutes and processed for immunohistochemical staining. Immunohistochemistry was performed with anti-mouse CD31 antibody (BD Biosciences, San Jose, CA), the VectaStain Kit (Vector, Burlingame, CA) and the Tyramide Signal Amplification (TSA) Biotin system (NEN Life Science Products, Boston, MA), according to the manufacturer's instructions.

Statistical analysis: All assays were independently performed at least three times. The results are represented as mean±standard deviation (SD). Groups were compared using the Student's t test and p values <0.05 were considered statistically significant.

REFERENCES

1. Klagsbrun M, Eichmann A. A role for axon guidance receptors and ligands in blood vessel development and tumor angiogenesis. *Cytokine & growth factor reviews* 16, 535-548 (2005).
2. Neufeld G, Kessler O. The semaphorins: versatile regulators of tumour progression and tumour angiogenesis. *Nature reviews Cancer* 8, 632-645 (2008).
3. Giger R J, Urquhart E R, Gillespie S K, Levengood D V, Ginty D D, Kolodkin A L. Neuropilin-2 is a receptor for semaphorin IV: insight into the structural basis of receptor function and specificity. *Neuron* 21, 1079-1092 (1998).
4. Takahashi T, Strittmatter S M. Plexin: autoinhibition by the plexin sema domain. *Neuron* 29, 429-439 (2001).
5. Bielenberg D R, et al. Semaphorin 3F, a chemorepulsant for endothelial cells, induces a poorly vascularized, encapsulated, nonmetastatic tumor phenotype. *The Journal of clinical investigation* 114, 1260-1271 (2004).
6. Shimizu A, et al. ABL2/ARG tyrosine kinase mediates SEMA3F-induced RhoA inactivation and cytoskeleton collapse in human glioma cells. *The Journal of biological chemistry* 283, 27230-27238 (2008).
7. Delgoffe G M, et al. Stability and function of regulatory T cells is maintained by a neuropilin-1-semaphorin-4a axis. *Nature* 501, 252-256 (2013).
8. Hansen W, et al. Neuropilin 1 deficiency on CD4+Foxp3+ regulatory T cells impairs mouse melanoma growth. *The Journal of experimental medicine* 209, 2001-2016 (2012).
9. Kumanogoh A, Kikutani H. Immunological functions of the neuropilins and plexins as receptors for semaphorins. *Nature reviews Immunology* 13, 802-814 (2013).

10. Weiss J M, et al. Neuropilin 1 is expressed on thymus-derived natural regulatory T cells, but not mucosa-generated induced Foxp3+ T reg cells. *The Journal of experimental medicine* 209, 1723-1742, s1721 (2012).
11. Bielenberg D R, et al. Increased smooth muscle contractility in mice deficient for neuropilin 2. *The American journal of pathology* 181, 548-559 (2012).
12. Procaccia V, Nakayama H, Shimizu A, Klagsbrun M. Gleevec/imatinib, an ABL2 kinase inhibitor, protects tumor and endothelial cells from semaphorin-induced cytoskeleton collapse and loss of cell motility. *Biochemical and biophysical research communications* 448, 134-138 (2014).
13. Potiron V A, et al. Semaphorin SEMA3F affects multiple signaling pathways in lung cancer cells. *Cancer research* 67, 8708-8715 (2007).
14. Nukazuka A, Tamaki S, Matsumoto K, Oda Y, Fujisawa H, Takagi S. A shift of the TOR adaptor from Rictor towards Raptor by semaphorin in *C. elegans*. *Nature communications* 2, 484 (2011).
15. Kim D H, et al. mTOR interacts with raptor to form a nutrient-sensitive complex that signals to the cell growth machinery. *Cell* 110, 163-175 (2002).
16. Sancak Y, et al. PRAS40 is an insulin-regulated inhibitor of the mTORC1 protein kinase. *Molecular cell* 25, 903-915 (2007).
17. Pearce L R, et al. Identification of Protor as a novel Rictor-binding component of mTOR complex-2. *The Biochemical journal* 405, 513-522 (2007).
18. Sarbassov D D, et al. Rictor, a novel binding partner of mTOR, defines a rapamycin-insensitive and raptor-independent pathway that regulates the cytoskeleton. *Current biology: CB* 14, 1296-1302 (2004).
19. Yang Q, Inoki K, Ikenoue T, Guan KL. Identification of Sin1 as an essential TORC2 component required for complex formation and kinase activity. *Genes & development* 20, 2820-2832 (2006).
20. Sarbassov D D, Ali S M, Sabatini D M. Growing roles for the mTOR pathway. *Current opinion in cell biology* 17, 596-603 (2005).
21. Wullschleger S, Loewith R, Hall MN. TOR signaling in growth and metabolism. *Cell* 124, 471-484 (2006).
22. Sarbassov D D, Guertin D A, Ali S M, Sabatini D M. Phosphorylation and regulation of Akt/PKB by the rictor-mTOR complex. *Science* (New York, NY) 307, 1098-1101 (2005).
23. Garcia-Martinez J M, Alessi D R. mTOR complex 2 (mTORC2) controls hydrophobic motif phosphorylation and activation of serum- and glucocorticoidinduced protein kinase 1 (SGK1). *The Biochemical journal* 416, 375-385 (2008).
24. Dormond O, Dufour M, Seto T, Bruneau S, Briscoe DM. Targeting the intragraft microenvironment and the development of chronic allograft rejection. *Human immunology* 73, 1261-1268 (2012).
25. Gamper C J, Powell J D. All PI3Kinase signaling is not mTOR: dissecting mTORdependent and independent signaling pathways in T cells. *Frontiers in immunology* 3, 312 (2012).
26. Powell J D, Delgoffe G M. The mammalian target of rapamycin: linking T cell differentiation, function, and metabolism. *Immunity* 33, 301-311 (2010).
27. Phung T L, et al. Pathological angiogenesis is induced by sustained Akt signaling and inhibited by rapamycin. *Cancer cell* 10, 159-170 (2006).
28. Mendes-da-Cruz D A, et al. Semaphorin 3F and neuropilin-2 control the migration of human T-cell precursors. *PloS one* 9, e103405 (2014).
29. Flaxenburg J A, Melter M, Lapchak P H, Briscoe D M, Pal S. The CD40-induced signaling pathway in endothelial cells resulting in the overexpression of vascular endothelial growth factor involves Ras and phosphatidylinositol 3-kinase. *Journal of immunology* (Baltimore, Md: 1950) 172, 7503-7509 (2004).
30. Kang S A, et al. mTORC1 phosphorylation sites encode their sensitivity to starvation and rapamycin. *Science* (New York, NY) 341, 1236566 (2013).
31. Pollizzi K N, Powell J D. Integrating canonical and metabolic signaling programmes in the regulation of T cell responses. *Nature reviews Immunology* 14, 435-446 (2014).
32. Bruneau S, Nakayama H, Woda C B, Flynn E A, Briscoe D M. DEPTOR regulates vascular endothelial cell activation and proinflammatory and angiogenic responses. *Blood* 122, 1833-1842 (2013).
33. Dazert E, Hall M N. mTOR signaling in disease. *Current opinion in cell biology* 23, 744-755 (2011).
34. Phung T L, et al. Endothelial Akt signaling is rate-limiting for rapamycin inhibition of mouse mammary tumor progression. *Cancer research* 67, 5070-5075 (2007).
35. Shimobayashi M, Hall M N. Making new contacts: the mTOR network in metabolism and signalling crosstalk. *Nature reviews Molecular cell biology* 15, 155-162 (2014).
36. Dormond O, et al. CD40-induced signaling in human endothelial cells results in mTORC2- and Akt-dependent expression of vascular endothelial growth factor in vitro and in vivo. *Journal of immunology* (Baltimore, Md: 1950) 181, 8088-8095 (2008).
37. Dormond O, Madsen J C, Briscoe D M. The effects of mTOR-Akt interactions on anti-apoptotic signaling in vascular endothelial cells. *The Journal of biological chemistry* 282, 23679-23686 (2007).
38. Zhang H H, Lipovsky A I, Dibble C C, Sahin M, Manning B D. S6K1 regulates GSK3 under conditions of mTOR-dependent feedback inhibition of Akt. *Molecular cell* 24, 185-197 (2006).
39. Burridge K, Wennerberg K. Rho and Rac take center stage. *Cell* 116, 167-179 (2004).
40. Carmeliet P, Jain R K. Principles and mechanisms of vessel normalization for cancer and other angiogenic diseases. *Nature reviews Drug discovery* 10, 417-427 (2011).
41. Ferrara N, Kerbel R S. Angiogenesis as a therapeutic target. *Nature* 438, 967-974 (2005).
42. Karar J, Maity A. PI3K/AKT/mTOR Pathway in Angiogenesis. *Frontiers in molecular neuroscience* 4, 51 (2011).
43. Krock B L, Skuli N, Simon M C. Hypoxia-induced angiogenesis: good and evil. *Genes & cancer* 2, 1117-1133 (2011).
44. Cao Y, et al. Neuropilin-2 promotes extravasation and metastasis by interacting with endothelial alpha5 integrin. *Cancer research* 73, 4579-4590 (2013).
45. Sabag A D, Bode J, Fink D, Kigel B, Kugler W, Neufeld G. Semaphorin-3D and semaphorin-3E inhibit the development of tumors from glioblastoma cells implanted in the cortex of the brain. *PloS one* 7, e42912 (2012).
46. Gan X, Wang J, Su B, Wu D. Evidence for direct activation of mTORC2 kinase activity by phosphatidylinositol 3,4,5-trisphosphate. *The Journal of biological chemistry* 286, 10998-11002 (2011).

47. Zinzalla V, Stracka D, Oppliger W, Hall M N. Activation of mTORC2 by association with the ribosome. *Cell* 144, 757-768 (2011).
48. Levitt R J, Georgescu M M, Pollak M. PTEN-induction in U251 glioma cells decreases the expression of insulin-like growth factor binding protein-2. *Biochemical and biophysical research communications* 336, 1056-1061 (2005).
49. Sakai A, Thieblemont C, Wellmann A, Jaffe E S, Raffeld M. PTEN gene alterations in lymphoid neoplasms. *Blood* 92, 3410-3415 (1998).
50. Wen S, et al. PTEN controls tumor-induced angiogenesis. *Proceedings of the National Academy of Sciences of the United States of America* 98, 4622-4627 (2001).
51. Cai H, Reed R R. Cloning and characterization of neuropilin-1-interacting protein: a PSD-95/Dlg/ZO-1 domain-containing protein that interacts with the cytoplasmic domain of neuropilin-1. *The Journal of neuroscience: the official journal of the Society for Neuroscience* 19, 6519-6527 (1999).
52. Katoh M. Functional proteomics, human genetics and cancer biology of GIPC family members. *Experimental & molecular medicine* 45, e26 (2013).
53. Wang L, Mukhopadhyay D, Xu X. C terminus of RGS-GAIP-interacting protein conveys neuropilin-1-mediated signaling during angiogenesis. *FASEB journal: official publication of the Federation of American Societies for Experimental Biology* 20, 1513-1515 (2006).
54. Peterson T R, et al. DEPTOR is an mTOR inhibitor frequently overexpressed in multiple myeloma cells and required for their survival. *Cell* 137, 873-886 (2009).
55. Jacinto E, et al. Mammalian TOR complex 2 controls the actin cytoskeleton and is rapamycin insensitive. *Nature cell biology* 6, 1122-1128 (2004).
56. Kessler O, et al. Semaphorin-3F is an inhibitor of tumor angiogenesis. *Cancer research* 64, 1008-1015 (2004).
57. Kigel B, Varshavsky A, Kessler O, Neufeld G. Successful inhibition of tumor development by specific class-3 semaphorins is associated with expression of appropriate semaphorin receptors by tumor cells. *PloS one* 3, e3287 (2008).
58. Sekulic A, et al. A direct linkage between the phosphoinositide 3-kinase-AKT signaling pathway and the mammalian target of rapamycin in mitogen-stimulated and transformed cells. *Cancer research* 60, 3504-3513 (2000).
59. Mukhopadhyay D, Knebelmann B, Cohen H T, Ananth S, Sukhatme V P. The von Hippel-Lindau tumor suppressor gene product interacts with Sp1 to repress vascular endothelial growth factor promoter activity. *Molecular and cellular biology* 17, 5629-5639 (1997).
60. Bielenberg D R, Shimizu A, Klagsbrun M. Semaphorin-induced cytoskeletal collapse and repulsion of endothelial cells. *Methods in enzymology* 443, 299-314 (2008).

Example 13

Figure 37:
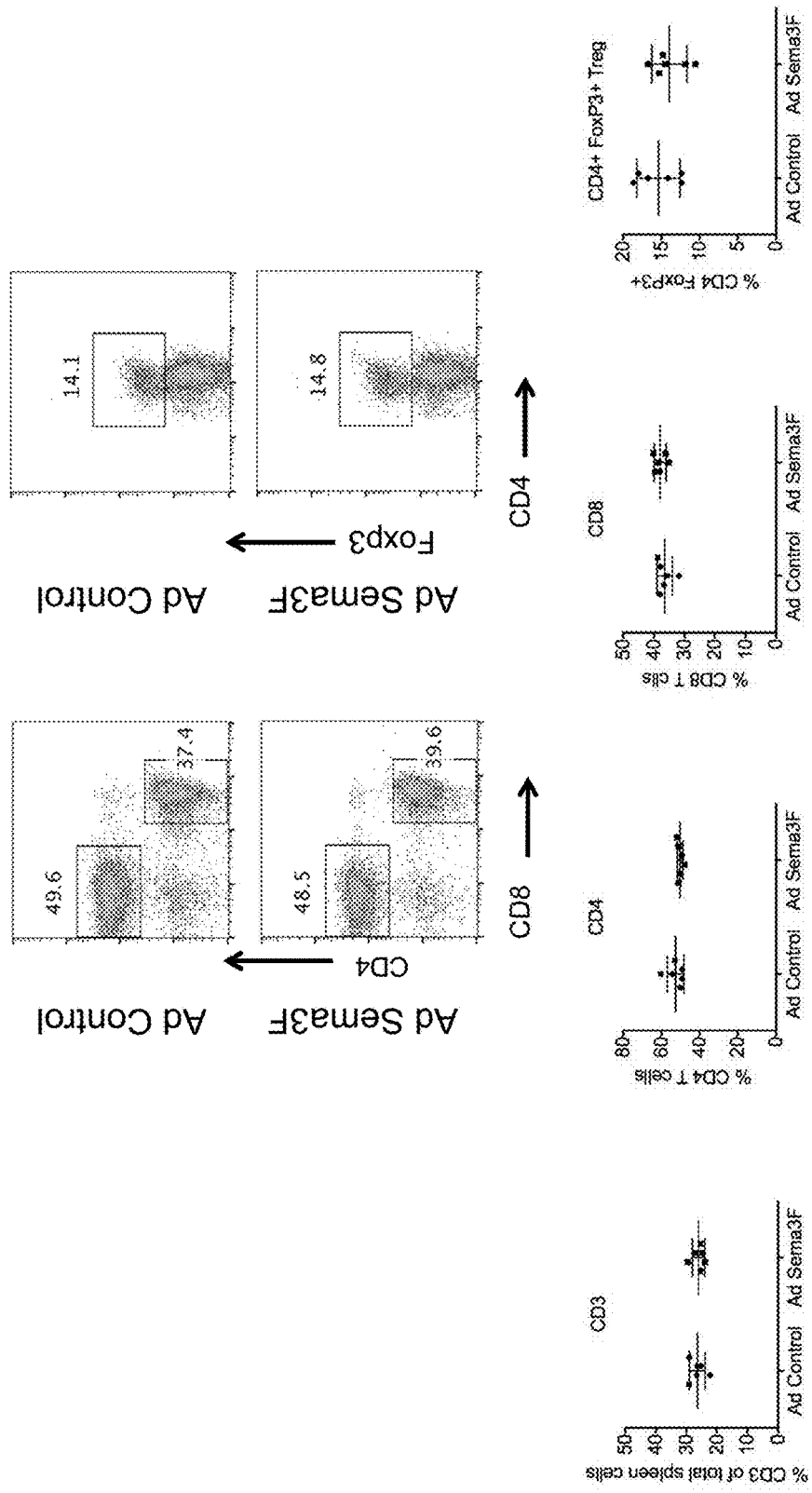
FIG. 37 depicts the phenotype of cells harvested from the mice identified in FIG. 2 on day 5 post transplantation. FACS analysis and graphical summaries demonstrating that no differences are observed in CD3, CD4, CD8 and Treg populations at early times post transplant.
Figure 38:
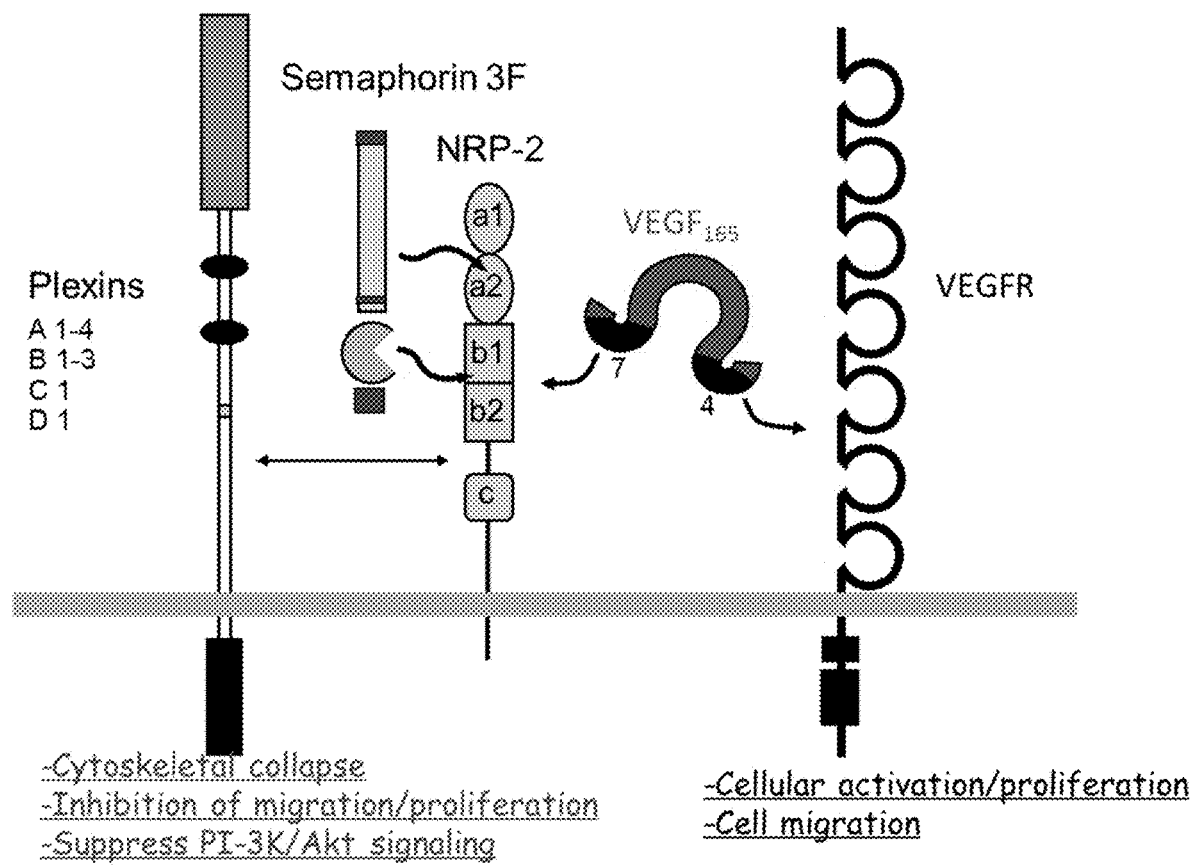
FIG. 38 depicts a schematic model of semaphorin-neuropilin-2 interactions.

The Immunoregulatory Function of Sema3F was Evaluated by Examining the Treg phenotype at early times post transplant, on day 5 shown in FIG. 2. As shown by FACS and in the lower panel in a summary (FIG. 37), no differences are observed in CD3, CD4, CD8 and Tregs.

Example 14

Figure 39:
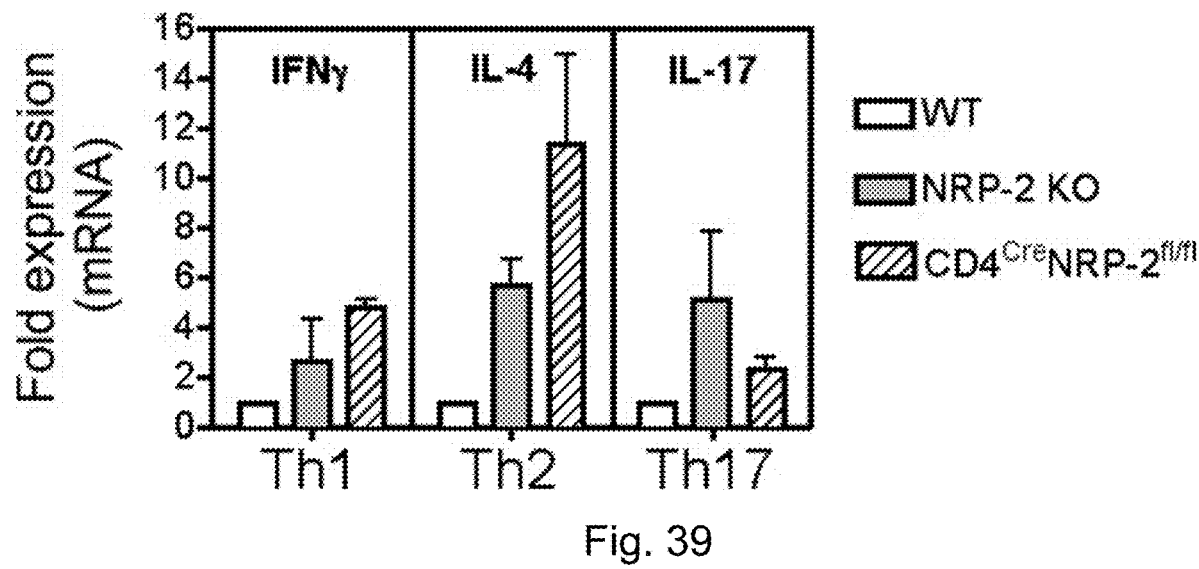
FIG. 39 is a follow up of FIGS. 11-16 and FIG. 23 where knockdown of NRP-2 was found to result in hyperactivity. In this Figure, T cells were mitogen activated in cultures that drive responses into different effector phenotypes. As depicted in the graph CD4+ T effector cell differentiation is enhanced in NRP-2 Knockout CD4+ T cells.

CD4+ T effector cell differentiation was examined in NRP-2 knockouts and conditional knockouts. Differentiation is enhanced in NRP-2 Knockout CD4+ T cells (FIG. 39). The data indicate that NRP-2 inhibits effector T cell expansion.

Example 15

Figure 40:
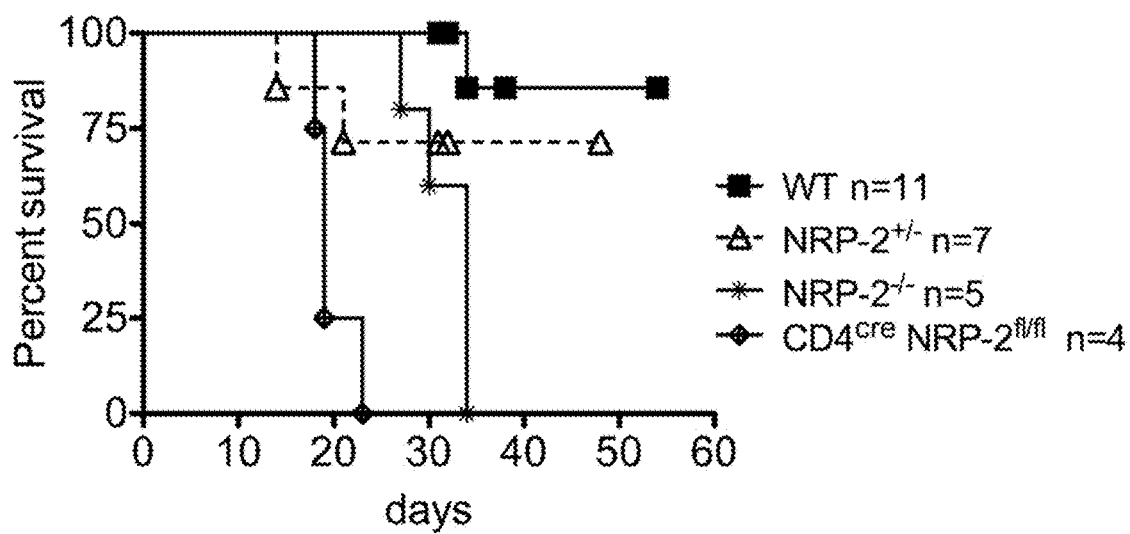
FIG. 40 is the combined data from FIGS. 5 and 25 demonstrating that NRP-2 deficiency led to accelerated cardiac allograft rejection. The figure depicts a graph of survival after minor MHC mismatched B6.C-H2$^{bm12}$ donor heart was transplanted into C57BL6 (WT) or NRP-2 heterozygote, and global or CD4+ T cell KO recipients.

Minor MHC mismatched B6.C-H2$^{bm12}$ donor heart was transplanted into C57BL6 (WT) or NRP-2 KO recipients and survival was determined. NRP-2 deficiency lead to accelerated cardiac allograft rejection (FIG. 40).

Example 16

Figure 41:
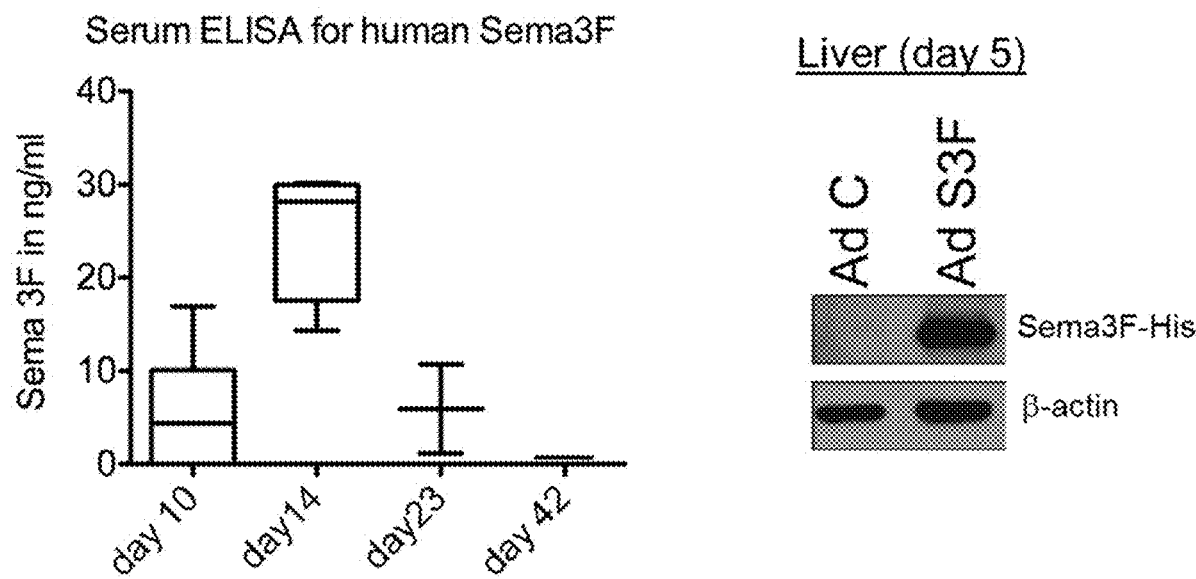
FIG. 41 shows data demonstrating the production of the NRP-2 ligand Sema3F in vivo by adenovirus.

To study the effect of the NRP-2 ligand Sema3F in vivo, an Adenovirus containing Sema3F or an empty control was administered into mice in a heart transplant model. The Sema3F vector increased production of Sema3F in the liver. Sema3F levels peak on day 14 following administration (FIG. 41).

TABLE 1

| Coodinate | Target | Control | SEMA3F | Ratio |
| --- | --- | --- | --- | --- |
| A1, A2 | Positive Control | 0.513 | 0.544 | 106.0 |
| A3, A4 | p38a (T180/Y182) | 0.292 | 0.268 | 91.8 |
| A5, A6 | ERK1/2 (T202/Y204, T185/Y187) | 0.330 | 0.301 | 91.2 |
| A7, A8 | JNK pan (T183/Y185, T221/Y223) | 0.313 | 0.287 | 91.5 |
| A9, A10 | GSK-3a/b (S21/S9) | 0.312 | 0.284 | 91.0 |
| A13, A14 | p53 (S392) | 0.332 | 0.312 | 94.0 |
| A17, A18 | Positive Control | 0.412 | 0.392 | 95.1 |
| B3, B4 | MEK1/2 (S218/S222, S222/S226) | 0.299 | 0.277 | 92.8 |
| B5, B6 | MSK1/2 (S376/S360) | 0.317 | 0.293 | 92.4 |
| B7, B8 | AMPKa1 (T174) | 0.290 | 0.269 | 92.7 |
| B9, B10 | Akt (S473) | 0.512 | 0.396 | 77.4 |
| B11, B12 | Akt (T308) | 0.317 | 0.294 | 92.6 |
| B13, B14 | p53 (S46) | 0.343 | 0.321 | 93.6 |
| C1, C2 | TOR (S2448) | 0.306 | 0.281 | 91.8 |
| C3, C4 | CREB (S133) | 0.323 | 0.295 | 91.3 |
| C5, C6 | HSP27 (S78/S82) | 0.294 | 0.277 | 94.0 |
| C7, C8 | AMPKa2 (T172) | 0.317 | 0.300 | 94.5 |
| C9, C10 | b-Catenin | 0.352 | 0.323 | 91.6 |
| C11, C12 | p70 S6 Kinase (T389) | 0.252 | 0.241 | 95.6 |
| C13, C14 | p53 (S15) | 0.322 | 0.312 | 96.7 |
| C15, C16 | p27 (T198) | 0.257 | 0.242 | 94.0 |
| C17, C18 | Paxillin (Y118) | 0.275 | 0.264 | 95.8 |
| D1, D2 | Src (Y419) | 0.317 | 0.289 | 91.0 |
| D3, D4 | Lyn (Y397) | 0.287 | 0.269 | 93.7 |
| D5, D6 | Lck (Y394) | 0.286 | 0.269 | 94.2 |
| D7, D8 | STAT2 (Y689) | 0.320 | 0.305 | 95.3 |
| D9, D10 | STAT5a (Y694) | 0.297 | 0.281 | 94.8 |
| D11, D12 | p70 S6 Kinase (T421/S424) | 0.307 | 0.299 | 97.4 |
| D13, D14 | RSK1/2/3 (S380/S386/S377) | 0.324 | 0.320 | 98.8 |
| D15, D16 | p27 (T157) | 0.264 | 0.249 | 94.3 |
| D17, D18 | PLCq-1 (Y783) | 0.275 | 0.262 | 95.1 |
| E1, E2 | Fyn (Y420) | 0.297 | 0.276 | 93.1 |
| E3, E4 | Yes (Y426) | 0.305 | 0.289 | 94.6 |
| E5, E6 | Fqr (Y412) | 0.280 | 0.264 | 94.1 |
| E7, E8 | STAT3 (Y705) | 0.289 | 0.270 | 93.4 |
| E9, E10 | STAT5b (Y699) | 0.291 | 0.270 | 92.6 |
| E11, E12 | p70 S6 Kinase (T229) | 0.264 | 0.264 | 100.0 |
| E13, E14 | RSK1/2 (S221/S227) | 0.314 | 0.307 | 97.8 |
| E15, E16 | c-Jun (S63) | 0.279 | 0.263 | 94.3 |
| E17, E18 | Pyk2 (Y402) | 0.269 | 0.251 | 93.1 |
| F1, F2 | Hck (Y411) | 0.295 | 0.270 | 91.4 |
| F3, F4 | Chk-2 (T68) | 0.318 | 0.297 | 93.4 |
| F5, F6 | FAK (Y397) | 0.314 | 0.275 | 87.7 |
| F7, F8 | STAT6 (Y641) | 0.315 | 0.304 | 96.3 |
| F9, F10 | STAT5a/b (Y694/Y699) | 0.345 | 0.311 | 90.1 |
| F11, F12 | STAT1 (Y701) | 0.304 | 0.298 | 98.2 |
| F13, F14 | STAT4 (Y693) | 0.295 | 0.285 | 96.4 |
| F15, F16 | eNOS (S1177) | 0.255 | 0.240 | 93.9 |
| F17 F18 | PBS (Negative Control) | — | — | — |
| G1, G2 | Positive Control | 0.490 | 0.487 | 99.4 |
| G5, G6 | PBS (Negative Control) | — | — | — |

What is claimed herein is:

1. A method of reducing Akt/mTOR signaling in a subject in need of thereof, the method comprising administering a Semaphorin Family III Member F (Sema3F) polypeptide comprising a sequence having at least 95% identity to the sequence of SEQ ID NO: 1 or SEQ ID NO:5 to the subject.

2. The method of claim 1, wherein the Sema3F polypeptide comprises the sequence of SEQ ID NO: 1 or SEQ ID NO: 5.

3. The method of claim 1, wherein the Sema3F polypeptide comprises the sequence of SEQ ID NO: 5.

4. The method of claim 1, wherein the subject is a subject having an autoimmune disease.

5. The method of claim 4, wherein the autoimmune disease is selected from the group consisting of:
Type 1 diabetes; systemic lupus erythematosus; rheumatoid arthritis; psoriasis; inflammatory bowel disease; Crohn's disease; and autoimmune thyroiditis.

6. The method of claim 1, wherein the subject is a subject having a local inflammatory condition.

7. The method of claim 6, wherein the local inflammatory condition is selected from the group consisting of:
a rash and an allergic reaction.

8. The method of claim 1, whereby the immune system of the subject is suppressed.

9. The method of claim 1, wherein the Sema3F polypeptide is administered intravenously.

10. The method of claim 1, wherein the Sema3F polypeptide is administered intramuscularly, subcutaneously, or intradermally.

11. The method of claim 1, wherein the Sema3F polypeptide is administered locally to a site of inflammation.

12. The method of claim 1, further comprising administering an additional anti-inflammatory agent.

13. The method of claim 12, wherein the additional anti-inflammatory agent is selected from the group consisting of:
a steroid; a calcineurin inhibitor; a mTOR inhibitor or an analogue thereof; and an anti-proliferative agent.

\* \* \* \* \*